(12) United States Patent
Chen et al.

(10) Patent No.: US 11,542,535 B2
(45) Date of Patent: Jan. 3, 2023

(54) METHODS FOR MANIPULATING BIOMOLECULES

(71) Applicant: LIFE TECHNOLOGIES CORPORATION, Carlsbad, CA (US)

(72) Inventors: Zhoutao Chen, Carlsbad, CA (US); Xiaoping Duan, Carlsbad, CA (US); Kyusung Park, Vista, CA (US)

(73) Assignee: Life Technologies Corporation, Carlsbad, CA (US)

( * ) Notice: Subject to any disclaimer, the term of this patent is extended or adjusted under 35 U.S.C. 154(b) by 386 days.

(21) Appl. No.: 14/315,140

(22) Filed: Jun. 25, 2014

(65) Prior Publication Data

US 2014/0343265 A1 Nov. 20, 2014

Related U.S. Application Data

(63) Continuation of application No. 13/482,542, filed on May 29, 2012, now abandoned.

(60) Provisional application No. 61/490,982, filed on May 27, 2011, provisional application No. 61/535,281, filed on Sep. 15, 2011, provisional application No. 61/579,109, filed on Dec. 22, 2011, provisional application No. 61/601,148, filed on Feb. 21, 2012.

(51) Int. Cl.
| | | |
|---|---|---|
| *C12Q 1/68* | (2018.01) | |
| *C12P 19/40* | (2006.01) | |
| *C12N 15/10* | (2006.01) | |
| *C12Q 1/6806* | (2018.01) | |

(52) U.S. Cl.
CPC .............. *C12P 19/40* (2013.01); *C12N 15/10* (2013.01); *C12N 15/1093* (2013.01); *C12Q 1/6806* (2013.01)

(58) Field of Classification Search
None
See application file for complete search history.

(56) References Cited

U.S. PATENT DOCUMENTS

| | | | |
|---|---|---|---|
| 4,888,274 A * | 12/1989 | Radding | C12Q 1/6839 435/6.1 |
| 5,173,418 A | 12/1992 | Molin et al. | |
| 6,197,557 B1 * | 3/2001 | Makarov | C12Q 1/6855 435/6.1 |
| 6,607,888 B2 | 8/2003 | Schwartz et al. | |
| 6,762,022 B2 | 7/2004 | Makarov et al. | |
| 6,777,187 B2 | 8/2004 | Makarov et al. | |
| 6,828,098 B2 | 12/2004 | Langmore et al. | |
| 7,270,958 B2 | 9/2007 | Makarov et al. | |
| 7,405,281 B2 | 7/2008 | Xu et al. | |
| 7,435,572 B2 | 10/2008 | Bitinaite | |
| 7,829,314 B2 | 11/2010 | Prudent et al. | |
| 7,851,192 B2 | 12/2010 | Guan et al. | |
| 7,948,015 B2 | 5/2011 | Rothberg et al. | |
| 8,048,664 B2 | 11/2011 | Guan et al. | |
| 8,202,691 B2 | 6/2012 | Steemers et al. | |
| 8,262,900 B2 | 9/2012 | Rothberg et al. | |
| 8,306,757 B2 | 11/2012 | Rothberg et al. | |
| 2002/0187508 A1 * | 12/2002 | Wong | C12Q 1/6825 435/5 |
| 2005/0019793 A1 * | 1/2005 | Kurn | C12Q 1/6844 435/6.1 |
| 2005/0130173 A1 * | 6/2005 | Leamon | B01L 3/502707 506/2 |
| 2006/0194214 A1 * | 8/2006 | Church | C12Q 1/6813 435/6.16 |
| 2007/0042379 A1 * | 2/2007 | Guan | C12N 9/22 435/6.11 |
| 2007/0178491 A1 | 8/2007 | Park et al. | |
| 2007/0219367 A1 * | 9/2007 | Shchepinov | C12Q 1/6869 536/25.32 |
| 2008/0166727 A1 | 7/2008 | Esfandyarpour et al. | |
| 2009/0026082 A1 | 1/2009 | Rothberg et al. | |
| 2009/0127589 A1 | 5/2009 | Rothberg et al. | |

(Continued)

FOREIGN PATENT DOCUMENTS

| | | |
|---|---|---|
| WO | WO-2002/031190 | 4/2002 |
| WO | WO-2002/040631 | 5/2002 |

(Continued)

OTHER PUBLICATIONS

Anderson, E. et al., "A system for multiplexed direct electrical detection of DNA synthesis", *Sensors and Actuators B Chem.*, vol. 129, 2008, 79-86.
Bergveld, P., "Thirty years of ISFETOLOGY What happened in the past 30 years and what may happen in the next 30 years", *Sensors and Actuators B*, vol. 88, 2003, pp. 1-20.
Chan, Siu-Hong et al., "Natural and engineered nicking endonucleases—from cleavage mechanism to engineering of strand-specificity", *Nucleic Acid Research*, 39:1, 2011, 1-18.
Chase, John et al. "Single-Stranded DNA Binding Proteins Required for DNA Replication", 1986, 103-136.
Chedin, F. et al., "Novel homologs of replication protein A in archaea: implications for the evolution of ssDNA-binding proteins", *TIBS*, vol. 23, Aug. 1998, 273-277.

(Continued)

*Primary Examiner* — Suryaprabha Chunduru

(57) ABSTRACT

In some embodiments, the present teachings provide compositions, systems, methods and kits for generating a population of nucleic acid fragments. In some embodiments, nucleic acids can be fragmented enzymatically. For example, methods for generating a population of nucleic acid fragments can include a nucleic acid nicking reaction. In one embodiment, the methods can include a nick translation reaction. A nicking reaction can introduce nicks at random positions on either strand of a double-stranded nucleic acid. A nick translation reaction can move the position of nicks to a new position so that the new positions of two of the nicks are aligned to create a double-stranded break. In some embodiments, methods for generating a population of nucleic acid fragments can include joining at least one end of a fragmented nucleic acid to one or more oligonucleotide adaptors.

12 Claims, 5 Drawing Sheets

Specification includes a Sequence Listing.

(56) References Cited

U.S. PATENT DOCUMENTS

| | | | | |
|---|---|---|---|---|
| 2009/0176234 | A1* | 7/2009 | Drmanac | C12Q 1/6855 435/6.12 |
| 2010/0009411 | A1* | 1/2010 | Nelson | C12N 9/93 435/89 |
| 2010/0028873 | A1 | 2/2010 | Belouchi et al. | |
| 2010/0137143 | A1* | 6/2010 | Rothberg | C12Q 1/6874 506/2 |
| 2010/0197507 | A1 | 8/2010 | Rothberg et al. | |
| 2010/0282617 | A1 | 11/2010 | Rothberg et al. | |
| 2010/0300559 | A1 | 12/2010 | Schultz et al. | |
| 2010/0300895 | A1 | 12/2010 | Nobile et al. | |
| 2010/0301398 | A1 | 12/2010 | Rothberg et al. | |
| 2011/0281736 | A1 | 11/2011 | Drmanac et al. | |

FOREIGN PATENT DOCUMENTS

| | | | |
|---|---|---|---|
| WO | WO-2006/084131 | 8/2006 | |
| WO | WO 2007056173 A1 * | 5/2007 | C12Q 1/6846 |
| WO | WO-201 2/050920 | 4/2012 | |
| WO | WO-2012/044847 | 4/2012 | |

OTHER PUBLICATIONS

Dodd, Helen et al., "The gene encoding a periplasmic deoxyribonuclease from Aeromonas hydrophila", *FEMS Microbiology Letters*, 173, 1999, 41-46.

Focareta, Tony et al., "Extracellular proteins of Vibrio cholerae: molecular cloning, nucleotide sequence and characterization of the deoxyribonuclease (DNase) together with its periplasmic localization in Escherichia coli K-12", *Gene*, 53, 1987, 31-40.

Haseltine, C. et al., "A distinctive single-stranded DNA-binding protein from the Archaeon Sulfolobus solfataricus", *Molecular Microbiology*, vol. 43, No. 6, 2002, 1505-1515.

Henegariu, Octavian et al., "Custom fluorescent-nucleotide synthesis as an alternative method for nucleic acid labeling", *Nature Biotechnology*, vol. 18, Mar. 2000, 345-348.

Iftode, Cristina et al., "Replication Protein A (RPA): The Eukaryotic SSB", *Critical Reviews in Biochemistry and Molecular Biology*, 34(3), 1999, 141-180.

Jekel, Manfred et al., "The periplasmic endonuclease I of Escherichia coli has amino-acid sequence homology to the extracellular DNases of Vibrio cholerae and A eromonas hydrophila", *Gene*, 154, 1995, 55-59.

Kelly, Thomas J. et al., "Identification and Characterization of a Single-Stranded DNA-Binding Protein From the Archaeon Methanococcus Jannaschii", *Proceedings of the National Academy of Sciences (PNAS)*, vol. 95, National Academy of Sciences of the USA, Dec. 1998, 14634-14639.

Klenk, H. P. et al., "The complete genome sequence of the hyperthermophilic, sulphate-reducing archaeon Archaeoglobus fulgidus", *Nature*, vol. 390, 1997, 364-370.

Kolodkin, Alex et al., "F sex factor of Escherichia coli K-12 codes for a single-stranded DNA binding protein", *Proc. Natl Acad. Sci. USA*, vol. 80, Jul. 1983, 4422-4426.

Kowalczykowski, Stephen et al., "Homologous Pairing and DNA Strand-Exchange Proteins", *Annu. Rev. Biochem.*, 63:, 1994, 991-1043.

Kuzminov, Andrei, "Recombinational Repair of DNA Damage in Escherichia coli and Bacteriophage I", *Microbiology and Molecular Biology Reviews*, vol. 63, No. 4, Dec. 1999, 751-813.

Leng, Xuefei et al., "Agarose droplet microfluidics for highly parallel and efficient single molecule emulsion PCR", *Lab Chip*, 10, 2010, 2841-2843.

Lohman, T. M. et al., "Escherichia coli Single-stranded DNA-Binding protein: Multiple DNA-Binding Modes and Cooperativities", *Annu. Rev. Biochem.*, vol. 63, 1994, 527-570.

Mathew, C.G.P., "Radiolabeling of DNA by Nick Translation", *Methods in Molecular Biology*, vol. 2, 1984, 257-261.

Moulard, M. et al., "Characterization of the nucM gene coding for a nuclease of the phytopathogenic bacteria Erwinia chrysanthemi", *Molecular Microbiology*, 8(4), 1993, 685-695.

Murzin, A. G., "OB-Fold: Common Structural and Functional Solution for Non-Homologous Sequences", *EMBO J.*, 12, 1993, 861-867.

PCT/US2012/039691, International Search Report and Written Opinion dated Aug. 20, 2012.

Philipova, D. et al., "A hierarchy of SSB protomers in replication protein A", *Genes Dev.*, vol. 10, 1996, 2222-2233.

Pourmand, N et al., "Direct electrical detection of DNA synthesis", *PNAS*, vol. 103(17), 2006, pp. 6466-6470.

Purushothaman, S. et al., "Towards Fast Solid State DNA Sequencing", *IEEE ISCAS 2002 Proceedings*, Circuits and Systems, vol. 4, 2002, pp IV-169-IV-172.

Rigby, Peter et al., "Labeling Deoxyribonucleic Acid to High Specific Activity in Vitro by Nick Translation with DNA Polymerase I", *J. Mol. Biol.*, vol. 113, 1977, pp. 237-251.

Rothwell, Paul J. et al., "Structure and Mechanism of DNA Polymerases", *Advances in Protein Chemistry*, vol. 71, 2005, 401-440.

Sakata, T. et al., "DNA Sequencing Based on Intrinsic Molecular Charges", *Angewandte Chemie International Edition 2006*, vol. 118, 2006, pp. 2283-2286.

Sakurai, T. et al., "Real-Time Monitoring of DNA Polymerase Reactions by a Micro ISFET pH Sensor", *Anal Chem*, vol. 64(17), 1992, pp. 1996-1997.

Sigal, Nolan et al., "A DNA-Unwinding Protein Isolated from Escherichia coli: Its Interaction with DNA and with DNA Polymerases", *Proc. Nat. Acad. Sci. USA*, vol. 69, No. 12, Dec. 1972, 3537-3541.

Skyberg, Jerod et al., "Acquisition of Avian Pathogenic Escherichia coli Plasmids by a Commensal E. coli Isolate Enhances Its Abilities To Kill Chicken Embryos, Grow in Human Urine, and Colonize the Murine Kidney", *Infection and Immunity*, vol. 74, No. 11, Nov. 2006, 6287-6292.

Smith, D. R. et al., "Complete genome sequence of Methanobacterium thermoautotrophicum deltaH: functional analysis and comparative genomics", *J. Bacterial*, vol. 179, No. 22, 1997, 7135-7155.

Topal, Michael et al., "Products of Bacteriophage T4 Genes 32 and 45 Improve the Accuracy of DNA Replication in Vitro", *J. Biol. Chem.*, vol. 258, No. 20, 1983, 12274-12279.

Wadsworth, R. et al., "Identification and properties of the crenarchaeal single-stranded DNA binding protein from Sulfolobus solfataricus", *Nucleic Acids Research*, vol. 29, No. 4, 2001, 914-920.

Wang, Yi-Ting et al., "Structural basis for sequence-dependent DNA cleavage by nonspecific endonucleases", *Nucleic Acids Research*, vol. 35, No. 2, 2007, 584-594.

Weiner, Joel et al., "The Deoxyribonucleic Acid Unwinding Protein of Escherichia coli", *The Journal of Biological Chemistry*, vol. 250, No. 6, 1975, 1972-1980.

Williams, Kenneth et al., "Primary Structure of the Bacteriophage T4 DNA Helix-destabilizing Protein", *J. Biol. Chem.*, vol. 256, No. 4, 1981, 1754-1762.

Wold, M. S. et al., "Replication Protein A: A Heterotrimeric, Single-Stranded DNA-Binding Protein Required for Eukaryotic DNA Metabolism", *Annu. Rev. Biochem.* 66:, Annual Reviews, Inc., 1997, 61-92.

XP002681382, "Ion Torrent: Ion Torrent Amplicon Sequencing", Retrieved from the Internet: URL:http://www.iontorrent.com/lib/images/PDFs/amplicon application note 040411.pdf, Apr. 4, 2011, 1-5.

XP002681383, "Ion Torrent: Ion Xpress Plus gDNA and Amplicon Library Preparation", Retrieved from the Internet:URL:http://fgcz-intranet.unizh.ch/publish/Next Gen Sequencing/PGM/4471989B.pdf, Oct. 7, 2011, 1-58.

XP002681387, "Invitrogen: Nick translation system", Retrieved from the Internet: URL:http://194.167.139.26/cgrunau/methods/NickTransKit. pdf, Oct. 2, 2003, 1-2.

Zhumabayeva, Bakhyt et al. "RecA—Mediated Affinity Capture: A Method for Full-Length cDNA Cloning", *BioTechniques*, 27:, Oct. 1999, 834-845.

Campbell V.W., et al., "The Effect of Divalent Cations on the Mode of Action of DNase I, The Initial Reaction Products Produced From

(56) References Cited

OTHER PUBLICATIONS

Covalently Closed Circular DNA", The Journal of Biological Chemistry, vol. 255, No. 8, Apr. 25, 1980, pp. 3726-3735.
European Search Report for Application No. EP17182518, dated Sep. 22, 2017, 5 pages.
Melgar E., et al., "Deoxyribonucleic acid Nucleases II. The Effects of Metals on the Mechanism of Action of Deoxyribonuclease I," The Journal of Biological Chemistry, vol. 243, No. 17, Sep. 10, 1968, pp. 4409-4416.

* cited by examiner

MFKRKSTAEL AAQMAKLNGN KGFSSEDKGE WKLKLDNAGN GQAVIRFLPS KNDEQAPFAI
LVNHGFKKNG KWYIETCSST HGDYDSCPVC QYISKNDLYN TDNKEYSLVK RKTSYWANIL
VVKDPAAPEN EGKVFKYRFG KKIWDKINAM IAVDVEMGET PVDVTCPWEG ANFVLKVKQV
SGFSNYDESK FLNQSAIPNI DDESFQKELF EQMVDLSEMT SKDKFKSFEE LNTKFGQVMG
TAVMGGAAAT AAKKADKVAD DLDAFNVDDF NTKTEDDFMS SSSGSSSSAD DTDLDDLLND
L

FIG. 4

MEEKVGNLKP NMESVNVTVR VLEASEARQI QTKNGVRTIS EAIVGDETGR VKLTLWGKHA
GSIKEGQVVK IENAWTTAFK GQVQLNAGSK TKIAEASEDG FPESSQIPEN TPTAPQQMRG
GGRGFRGGGR RYGRRGGRRQ ENEEGEEE

FIG. 5

MANLQVATSE TWRDKQTGEM REQTEWHRVV LFGKLAEVAG EYLRKGVQVY IEGQLRTRSW
EDNGITRYVH PKFLLRPQGT NARCWDVPQV LRLKLERGAN SFKTAQPFKP GNPTRPGGPG
LRKKRVAPKR KAVDVRPRSR SLSCNRRRVT ITGFQTISRS ERADCDNRPA PVLCGASPER

FIG. 6

```
MIGDYERFKQ LKKKVAEALN ISEEELDRMI DKKIEENGGI ILKDAALMMI AKEHGVYGEE
KNDEEFLISD IEEGQIGVEI TGVITDISEI KTFKRRDGSL GKYKRITIAD KSGTIRMTLW
DDLAELDVKV GDVIKIERAR ARKWRNNLEL SSTSETKIKK LENYEGELPE IKDTYNIGEL
SPGMTATFEG EVISALPIKE FKRADGSIGK LKSFIVRDET GSIRVTLWDN LTDIDVGRGD
YVRVRGYIRE GYYGGLECTA NYVEILKKGE KIESEEVNIE DLTKYEDGEL VSVKGRVIAI
SNKKSVDLDG EIAKVQDIIL DNGTGRVRVS FWRGKTALLE NIKEGDLVRI TNCRVKTFYD
REGNKRTDLV ATLETEVIKD ENIEAPEYEL KYCKIEDIYN RDVDWNDINL IAQVVEDYGV
NEIEFEDKVR KVRNLLLEDG TGRIRLSLWD DLAEIEIKEG DIVEILHAYA KERGDYIDLV
IGKYGRIIIN PEGVEIKTNR KFIADIEDGE TVEVRGAVVK ILSDTLFLYL CPNCRKRVVE
IDGIYNCPIC GDVEPEEILR LNFVVDDGTG TLLCRAYDRR VEKMLKMNRE ELKNLTIEMV
EDEILGEEFV LYGNVRVEND ELIMVVRRVN DVDVEKEIRI LEEME
```

FIG. 7

SEQUENCE LISTING

```
<160> NUMBER OF SEQ ID NOS: 4

<210> SEQ ID NO 1
<211> LENGTH: 301
<212> TYPE: PRT
<213> ORGANISM: phage T4
<220> FEATURE:
<221> NAME/KEY: MISC_FEATURE
<223> OTHER INFORMATION: gp 32 protein

<400> SEQUENCE: 1
```

Met Phe Lys Arg Lys Ser Thr Ala Glu Leu Ala Ala Gln Met Ala Lys
1               5                   10                  15

Leu Asn Gly Asn Lys Gly Phe Ser Ser Glu Asp Lys Gly Glu Trp Lys
            20                  25                  30

Leu Lys Leu Asp Asn Ala Gly Asn Gly Gln Ala Val Ile Arg Phe Leu
        35                  40                  45

Pro Ser Lys Asn Asp Glu Gln Ala Pro Phe Ala Ile Leu Val Asn His
    50                  55                  60

Gly Phe Lys Lys Asn Gly Lys Trp Tyr Ile Glu Thr Cys Ser Ser Thr
65                  70                  75                  80

His Gly Asp Tyr Asp Ser Cys Pro Val Cys Gln Tyr Ile Ser Lys Asn
                85                  90                  95

Asp Leu Tyr Asn Thr Asp Asn Lys Glu Tyr Ser Leu Val Lys Arg Lys
            100                 105                 110

Thr Ser Tyr Trp Ala Asn Ile Leu Val Val Lys Asp Pro Ala Ala Pro
        115                 120                 125

Glu Asn Glu Gly Lys Val Phe Lys Tyr Arg Phe Gly Lys Lys Ile Trp
    130                 135                 140

Asp Lys Ile Asn Ala Met Ile Ala Val Asp Val Glu Met Gly Glu Thr
145                 150                 155                 160

```
Pro Val Asp Val Thr Cys Pro Trp Glu Gly Ala Asn Phe Val Leu Lys
            165                 170                 175

Val Lys Gln Val Ser Gly Phe Ser Asn Tyr Asp Glu Ser Lys Phe Leu
        180                 185                 190

Asn Gln Ser Ala Ile Pro Asn Ile Asp Asp Glu Ser Phe Gln Lys Glu
        195                 200                 205

Leu Phe Glu Gln Met Val Asp Leu Ser Glu Met Thr Ser Lys Asp Lys
210                 215                 220

Phe Lys Ser Phe Glu Glu Leu Asn Thr Lys Phe Gly Gln Val Met Gly
225                 230                 235                 240

Thr Ala Val Met Gly Ala Ala Ala Thr Ala Ala Lys Lys Ala Asp
                245                 250                 255

Lys Val Ala Asp Asp Leu Asp Ala Phe Asn Val Asp Asp Phe Asn Thr
                260                 265                 270

Lys Thr Glu Asp Asp Phe Met Ser Ser Ser Gly Ser Ser Ser Ser
                275                 280                 285

Ala Asp Asp Thr Asp Leu Asp Leu Leu Asn Asp Leu
        290                 295                 300

<210> SEQ ID NO 2
<211> LENGTH: 148
<212> TYPE: PRT
<213> ORGANISM: Sulfolobus solfataricus

<400> SEQUENCE: 2

Met Glu Glu Lys Val Gly Asn Leu Lys Pro Asn Met Glu Ser Val Asn
1               5                   10                  15

Val Thr Val Arg Val Leu Glu Ala Ser Glu Ala Arg Gln Ile Gln Thr
            20                  25                  30

Lys Asn Gly Val Arg Thr Ile Ser Glu Ala Ile Val Gly Asp Glu Thr
        35                  40                  45

Gly Arg Val Lys Leu Thr Leu Trp Gly Lys His Ala Gly Ser Ile Lys
    50                  55                  60

Glu Gly Gln Val Val Lys Ile Glu Asn Ala Trp Thr Thr Ala Phe Lys
65                  70                  75                  80

Gly Gln Val Gln Leu Asn Ala Gly Ser Lys Thr Lys Ile Ala Glu Ala
                85                  90                  95

Ser Glu Asp Gly Phe Pro Glu Ser Ser Gln Ile Pro Glu Asn Thr Pro
            100                 105                 110

Thr Ala Pro Gln Gln Met Arg Gly Gly Arg Gly Phe Arg Gly Gly
        115                 120                 125

Gly Arg Arg Tyr Gly Arg Arg Gly Gly Arg Gln Glu Asn Glu Glu
    130                 135                 140

Gly Glu Glu Glu
145

<210> SEQ ID NO 3
<211> LENGTH: 180
<212> TYPE: PRT
<213> ORGANISM: Escherichia coli

<400> SEQUENCE: 3

Met Ala Asn Leu Gln Val Ala Thr Ser Glu Thr Trp Arg Asp Lys Gln
1               5                   10                  15

Thr Gly Glu Met Arg Glu Gln Thr Glu Trp His Arg Val Val Leu Phe
            20                  25                  30
```

Gly Lys Leu Ala Glu Val Ala Gly Glu Tyr Leu Arg Lys Gly Val Gln
            35                  40                  45

Val Tyr Ile Glu Gly Gln Leu Arg Thr Arg Ser Trp Glu Asp Asn Gly
 50                  55                  60

Ile Thr Arg Tyr Val His Pro Lys Phe Leu Leu Arg Pro Gln Gly Thr
 65                  70                  75                  80

Asn Ala Arg Cys Trp Asp Val Pro Gln Val Leu Arg Leu Lys Leu Glu
                85                  90                  95

Arg Gly Ala Asn Ser Phe Lys Thr Ala Gln Pro Phe Lys Pro Gly Asn
            100                 105                 110

Pro Thr Arg Pro Gly Gly Pro Gly Leu Arg Lys Arg Val Ala Pro
            115                 120                 125

Lys Arg Lys Ala Val Asp Val Arg Pro Arg Ser Arg Ser Leu Ser Cys
130                 135                 140

Asn Arg Arg Arg Val Thr Ile Thr Gly Phe Gln Thr Ile Ser Arg Ser
145                 150                 155                 160

Glu Arg Ala Asp Cys Asp Asn Arg Pro Ala Pro Val Leu Cys Gly Ala
                165                 170                 175

Ser Pro Glu Arg
            180

<210> SEQ ID NO 4
<211> LENGTH: 645
<212> TYPE: PRT
<213> ORGANISM: Methanococcus jannaschii

<400> SEQUENCE: 4

Met Ile Gly Asp Tyr Glu Arg Phe Lys Gln Leu Lys Lys Lys Val Ala
 1               5                  10                  15

Glu Ala Leu Asn Ile Ser Glu Glu Leu Asp Arg Met Ile Asp Lys
            20                  25                  30

Lys Ile Glu Glu Asn Gly Gly Ile Ile Leu Lys Asp Ala Ala Leu Met
            35                  40                  45

Met Ile Ala Lys Glu His Gly Val Tyr Gly Glu Glu Lys Asn Asp Glu
 50                  55                  60

Glu Phe Leu Ile Ser Asp Ile Glu Gly Gln Ile Gly Val Glu Ile
 65                  70                  75                  80

Thr Gly Val Ile Thr Asp Ile Ser Glu Ile Lys Thr Phe Lys Arg Arg
                85                  90                  95

Asp Gly Ser Leu Gly Lys Tyr Lys Arg Ile Thr Ile Ala Asp Lys Ser
            100                 105                 110

Gly Thr Ile Arg Met Thr Leu Trp Asp Asp Leu Ala Glu Leu Asp Val
            115                 120                 125

Lys Val Gly Asp Val Ile Lys Ile Glu Arg Ala Arg Ala Lys Trp
130                 135                 140

Arg Asn Asn Leu Glu Leu Ser Thr Ser Glu Thr Lys Ile Lys Lys
145                 150                 155                 160

Leu Glu Asn Tyr Glu Gly Glu Leu Pro Glu Ile Lys Asp Thr Tyr Asn
                165                 170                 175

Ile Gly Glu Leu Ser Pro Gly Met Thr Ala Thr Phe Glu Gly Glu Val
            180                 185                 190

Ile Ser Ala Leu Pro Ile Lys Glu Phe Lys Arg Ala Asp Gly Ser Ile
            195                 200                 205

Gly Lys Leu Lys Ser Phe Ile Val Arg Asp Glu Thr Gly Ser Ile Arg

-continued

```
            210                 215                 220
Val Thr Leu Trp Asp Asn Leu Thr Asp Ile Asp Val Gly Arg Gly Asp
225                 230                 235                 240

Tyr Val Arg Val Arg Gly Tyr Ile Arg Glu Gly Tyr Tyr Gly Gly Leu
                245                 250                 255

Glu Cys Thr Ala Asn Tyr Val Glu Ile Leu Lys Lys Gly Glu Lys Ile
                    260                 265                 270

Glu Ser Glu Glu Val Asn Ile Glu Asp Leu Thr Lys Tyr Glu Asp Gly
                275                 280                 285

Glu Leu Val Ser Val Lys Gly Arg Val Ile Ala Ile Ser Asn Lys Lys
                290                 295                 300

Ser Val Asp Leu Asp Gly Glu Ile Ala Lys Val Gln Asp Ile Ile Leu
305                 310                 315                 320

Asp Asn Gly Thr Gly Arg Val Arg Val Ser Phe Trp Arg Gly Lys Thr
                    325                 330                 335

Ala Leu Leu Glu Asn Ile Lys Glu Gly Asp Leu Val Arg Ile Thr Asn
                340                 345                 350

Cys Arg Val Lys Thr Phe Tyr Asp Arg Glu Gly Asn Lys Arg Thr Asp
                355                 360                 365

Leu Val Ala Thr Leu Glu Thr Glu Val Ile Lys Asp Glu Asn Ile Glu
                370                 375                 380

Ala Pro Glu Tyr Glu Leu Lys Tyr Cys Lys Ile Glu Asp Ile Tyr Asn
385                 390                 395                 400

Arg Asp Val Asp Trp Asn Asp Ile Asn Leu Ile Ala Gln Val Val Glu
                    405                 410                 415

Asp Tyr Gly Val Asn Glu Ile Glu Phe Glu Asp Lys Val Arg Lys Val
                420                 425                 430

Arg Asn Leu Leu Leu Glu Asp Gly Thr Gly Arg Ile Arg Leu Ser Leu
                435                 440                 445

Trp Asp Asp Leu Ala Glu Ile Glu Ile Lys Glu Gly Asp Ile Val Glu
                450                 455                 460

Ile Leu His Ala Tyr Ala Lys Glu Arg Gly Asp Tyr Ile Asp Leu Val
465                 470                 475                 480

Ile Gly Lys Tyr Gly Arg Ile Ile Asn Pro Glu Gly Val Glu Ile
                    485                 490                 495

Lys Thr Asn Arg Lys Phe Ile Ala Asp Ile Glu Asp Gly Glu Thr Val
                500                 505                 510

Glu Val Arg Gly Ala Val Val Lys Ile Leu Ser Asp Thr Leu Phe Leu
                515                 520                 525

Tyr Leu Cys Pro Asn Cys Arg Lys Arg Val Val Glu Ile Asp Gly Ile
                530                 535                 540

Tyr Asn Cys Pro Ile Cys Gly Asp Val Glu Pro Glu Glu Ile Leu Arg
545                 550                 555                 560

Leu Asn Phe Val Val Asp Asp Gly Thr Gly Thr Leu Leu Cys Arg Ala
                    565                 570                 575

Tyr Asp Arg Arg Val Glu Lys Met Leu Lys Met Asn Arg Glu Glu Leu
                580                 585                 590

Lys Asn Leu Thr Ile Glu Met Val Glu Asp Glu Ile Leu Gly Glu Glu
                595                 600                 605

Phe Val Leu Tyr Gly Asn Val Arg Val Glu Asn Asp Glu Leu Ile Met
                610                 615                 620
```

-continued

```
Val Val Arg Arg Val Asn Asp Val Asp Val Glu Lys Glu Ile Arg Ile
625                 630             635                 640

Leu Glu Glu Met Glu
                645
```

METHODS FOR MANIPULATING BIOMOLECULES

This application is a continuation of U.S. Non-Provisional application Ser. No. 13/482,542, filed on May 29, 2012, which claims the filing date benefit of U.S. Provisional Application Nos. 61/490,982, filed on May 27, 2011, and 61/535,281, filed on Sep. 15, 2011, and 61/579,109, filed on Dec. 22, 2011, and 61/601,148, filed Feb. 21, 2012.

Throughout this application various publications, patents, and/or patent applications are referenced. The disclosures of these publications, patents, and/or patent applications in their entireties are hereby incorporated by reference into this application in order to more fully describe the state of the art to which this invention pertains.

FIELD

In some embodiments, the present teachings provide methods for manipulating double-stranded nucleic acids to produce a population of nucleic acid fragments.

INTRODUCTION

Nucleic acid manipulations can often involve a fragmenting step. Nucleic acid fragments can be used in a variety of processes and methods, including in the preparation of nucleic acids for sequencing. Sequencing of fragments of nucleic acids is common in capillary electrophoretic, hybridization-based, ligation-based and sequence-by-synthesis-bases sequencing processes. Fragmenting sample nucleic acids can be useful for next-generation sequencing processes, in which large numbers of relatively small nucleic acid fragments can be sequenced at the same time in parallel. Many sample and library preparation process for next-generation sequencing include a fragmentation step as part of the workflow.

SUMMARY

In some embodiments, the present teachings provide compositions, systems, methods and kits for generating a population of nucleic acid fragments.

In some embodiments, the present teachings provide compositions, systems, methods and kits for introducing at least one double stranded break into a sample nucleic acid.

In some embodiments, the present teachings provide compositions, systems, methods and kits for generating a double stranded break, resulting in the formation of at least two nucleic acid fragments derived from an original double stranded sample nucleic acid.

In some embodiments, a sample nucleic acid can include single stranded or double stranded nucleic acids.

Optionally, the methods comprise subjecting the sample nucleic acid to nicking conditions. In some embodiments, the nicking conditions comprise introducing one or more nicks into a sample nucleic acid. In some embodiments, the nicking conditions comprise introducing at least one nick on each strand of a double stranded sample nucleic acid. In some embodiments, the nicks are introduced at random positions in the sample nucleic acid.

Optionally, the methods comprise subjecting the sample nucleic acid to nick translating conditions. In some embodiments, the methods comprise translating at least one nick. In some embodiments, the nick translating conditions comprise translating at least one nick on each strand of a double stranded sample nucleic acid. In some embodiments, the nick translating conditions include translating at least two nicks located on opposing nucleic acid strands towards each other. In some embodiments, the nick translating conditions include translating the position of a first nick on one strand to a new position that can be aligned with a second nick, break, or other gap in the opposing strand. In some embodiments, alignment of nicks, breaks, or gaps can result in double-stranded breaks or fragmentation points in the sample nucleic acid.

In some embodiments, methods for generating a population of nucleic acid fragments comprise: nicking a nucleic acid; and nick translating the nicks.

Optionally, the nick translating conditions can include labeled or unlabeled nucleotides, or a mixture of both. In some embodiments, the nick translating conditions conducted with unlabeled nucleotides generate a population of unlabeled nucleic acid fragments.

In some embodiments, methods for generating a population of nucleic acid fragments comprise introducing at least one double stranded break into a sample nucleic acid to generate a population of unlabeled nucleic acid fragments.

In some embodiments, methods for generating a population of nucleic acid fragments comprise: nicking a nucleic acid at least once on each strand; and nick translating the nicks thereby generating a double-stranded break to produce nucleic acid fragments.

In some embodiments, methods for generating a population of nucleic acid fragments comprise: introducing a double stranded break (cleave) in a sample nucleic acid by: nicking the sample nucleic acid at least once on each strand; and nick translating the nicks thereby generating a double-stranded break to produce nucleic acid fragments.

In some embodiments, methods for generating a population of nucleic acid fragments comprise: providing a double-stranded nucleic acid having a first and a second strand; and nicking the first and second strand. Optionally the first strand can be nicked at least once to produce a first nick and the second strand can be nicked at least once to produce a second nick. Optionally, the methods further comprise nick translating the first nick and the second nick towards each other, thereby generating a double-stranded break to produce nucleic acid fragments.

In some embodiments, methods for generating a population of nucleic acid fragments comprise: introducing one or more nicks on each strand of a double-stranded nucleic acid. Optionally, the methods include generating at least one double-stranded break by moving the positions of at least two of the nicks along their respective strands, thereby cleaving the double stranded nucleic acid into at least two nucleic acid fragments.

In some embodiments, methods for generating a population of nucleic acid fragments comprise: subjecting two or more different double stranded nucleic acids to nicking conditions, thereby forming at least two different nicked double stranded nucleic acids. In some embodiments, each of at least two different nicked double stranded nucleic acids includes at least one nick in each strand. Optionally, the methods comprise translating the at least one nick in each strand so as to align the nicks on opposing strands. In some embodiments, the translating includes subjecting the at least two different nicked double stranded nucleic acids to nick translating conditions.

In some embodiments, methods for generating a population of nucleic acid fragments comprise: subjecting two or more different double stranded nucleic acids to a nicking conditions, thereby forming at least two different nicked double stranded nucleic acids. In some embodiments, each of the two or more different double stranded nucleic acids includes at least one nick in each strand. Optionally, the methods comprise cleaving the at least two different nicked double stranded nucleic acids, wherein the cleaving includes creating at least one double stranded break in each of the at least two different nicked double stranded nucleic acids. In some embodiments, the creating includes nick translating the least one nick in each strand, thereby generating a population of nucleic acid fragments.

In some embodiments, methods for generating a population of nucleic acid fragments comprise: cleaving at least two different double stranded nucleic acid molecules into nucleic acid fragments. In some embodiments, the cleaving includes introducing at least one nick into each strand of the at least two different double stranded nucleic acid molecules by subjecting the at least two different double stranded nucleic acid molecules to nicking conditions, thereby forming nicked double stranded nucleic acid molecules. Optionally, the method comprises generating one or more double stranded breaks in the nicked double stranded nucleic acid molecules by nick translating one or more nicks in a first strand and one or more nicks in a second strand of the nicked double stranded nucleic acid molecule until at least two nicks on opposing strands are aligned.

In some embodiments, methods for generating a population of nucleic acid fragments comprise: subjecting two or more different double stranded nucleic acids to nicking conditions, thereby forming at least two different nicked double stranded nucleic acids, each including at least one nick in each strand; cleaving the at least two different nicked double stranded nucleic acids, wherein the cleaving includes creating at least one double stranded break in each of the at least two different nicked double stranded nucleic acids, wherein the creating includes nick translating the least one nick in each strand, thereby generating a population of nucleic acid fragments.

In some embodiments, methods for generating a population of nucleic acid fragments comprise: cleaving at least two different double stranded nucleic acid molecules into nucleic acid fragments, wherein the cleaving includes introducing at least one nick into each strand of the at least two different double stranded nucleic acid molecules by subjecting the at least two different double stranded nucleic acid molecules to nicking conditions, thereby forming nicked double stranded nucleic acid molecules; and generating one or more double stranded breaks in the nicked double stranded nucleic acid molecules by nick translating one or more nicks in a first strand and one or more nicks in the second strand of the nicked double stranded nucleic acid molecule until at least two nicks on opposing strands are aligned.

In some embodiments, the method comprises modulating the nicking conditions so as to adjust the average size of the nucleic acid fragments.

In some embodiments, the translating includes polymerizing one or more nucleotides onto the 3' end of at least one nick. In some embodiments, labeled or unlabeled nucleotides can be polymerized onto the 3' end of at least one nick.

In some embodiments, at least one of the nucleic acid fragments is not labeled.

In some embodiments, substantially all of the nucleic acid fragments are not labeled.

In some embodiments, the method generates a population of unlabeled nucleic acid fragments.

Optionally, the methods further comprise: ligating at least one oligonucleotide adapter to at least one end of one or more nucleic acid fragments in the population of nucleic acid fragments.

Optionally, the methods further comprise: cloning one or more of the nucleic acid fragments.

In some embodiments, the population of nucleic acid fragments includes substantially similar-sized fragments.

In some embodiments, the population of nucleic acid fragments includes substantially dissimilar-sized nucleic acid fragments.

In some embodiments, in a population of nucleic acids, substantially similar-sized fragments can differ from each other on average by about less than 50 bp, or can differ from each other on average by about 50-100 bp, or by about 100-200 bp, or by about 200-300 bp, or by about 300-400 bp, or by about 400-500 bp, or by about 500-600 bp, or by about 600-700 bp.

In some embodiments, a population of nucleic acids comprises an average size range of about 50-150 bp, or about 150-250 bp, or about 250-500 bp, or about 500-750 bp, or about 750-1000 bp, or about 1-2 kb, or about 2-5 kb, or about 5-8 kb, or about 8-10 kb, or about 10-20 kb, or about 20-40 kb, or about 40-60 kb, or longer.

In some embodiments, at least one end of a fragment in the population comprises a blunt end.

In some embodiments, at least one end of a fragment in the population comprises an overhang end.

In some embodiments, at least one end of a fragment in the population comprises or lacks a 5' phosphate group.

In some embodiments, at least one end of a fragment in the population comprises or lacks a 3' OH group.

In some embodiments, the nicking comprises enzymatic nicking.

In some embodiments, the nick translating comprises a 5' to 3' DNA polymerization/degradation reaction or a 5' to 3' DNA polymerization/strand displacement reaction.

Optionally, the methods comprise joining at least one oligonucleotide adaptor to at least one end of a fragment of the population o nucleic acid fragments.

In some embodiments, one strand of at least one end of a fragment of the population can be joined to one strand of a double-stranded oligonucleotide adaptor to generate a fragment-adaptor molecule having a break or nick between the adaptor and the fragment.

In some embodiments, both strands of at least one end of a fragment of the population can be joined to both strands of a double-stranded oligonucleotide adaptor.

Optionally, the nicking step comprises at least one nucleic acid binding protein. Optionally, nick translating step comprises at least one nucleic acid binding protein.

In some embodiments, the nucleic acid binding protein comprises a single-stranded binding protein.

In some embodiments, the single-stranded binding protein comprises a phage T4 gp 32 protein, a *Sulfolobus solfataricus* single-stranded binding protein, a *Methanococcus jannaschii* single-stranded binding protein, or an *E. coli* single-stranded binding protein.

In some embodiments, the nucleic acid binding protein comprises an amino acid sequence according to any one of SEQ ID NOS:1, 2, 3 or 4.

A population of nucleic acid fragments generated by the teachings provided herein.

DRAWINGS

FIG. 4 shows a non-limiting embodiment of an amino acid sequence of a phage T4 gp 32 protein (SEQ ID NO:1).

FIG. 5 shows a non-limiting embodiment of an amino acid sequence of a single-stranded binding protein from *Sulfolobus solfataricus* (SEQ ID NO:2)

FIG. 6 shows a non-limiting embodiment of an amino acid sequence of a single-stranded binding protein from *E. coli* (SEQ ID NO:3).

FIG. 7 shows a non-limiting embodiment of an amino acid sequence of a single-stranded binding protein from *Methanococcus jannaschii* (SEQ ID NO:4).

Figure 1:
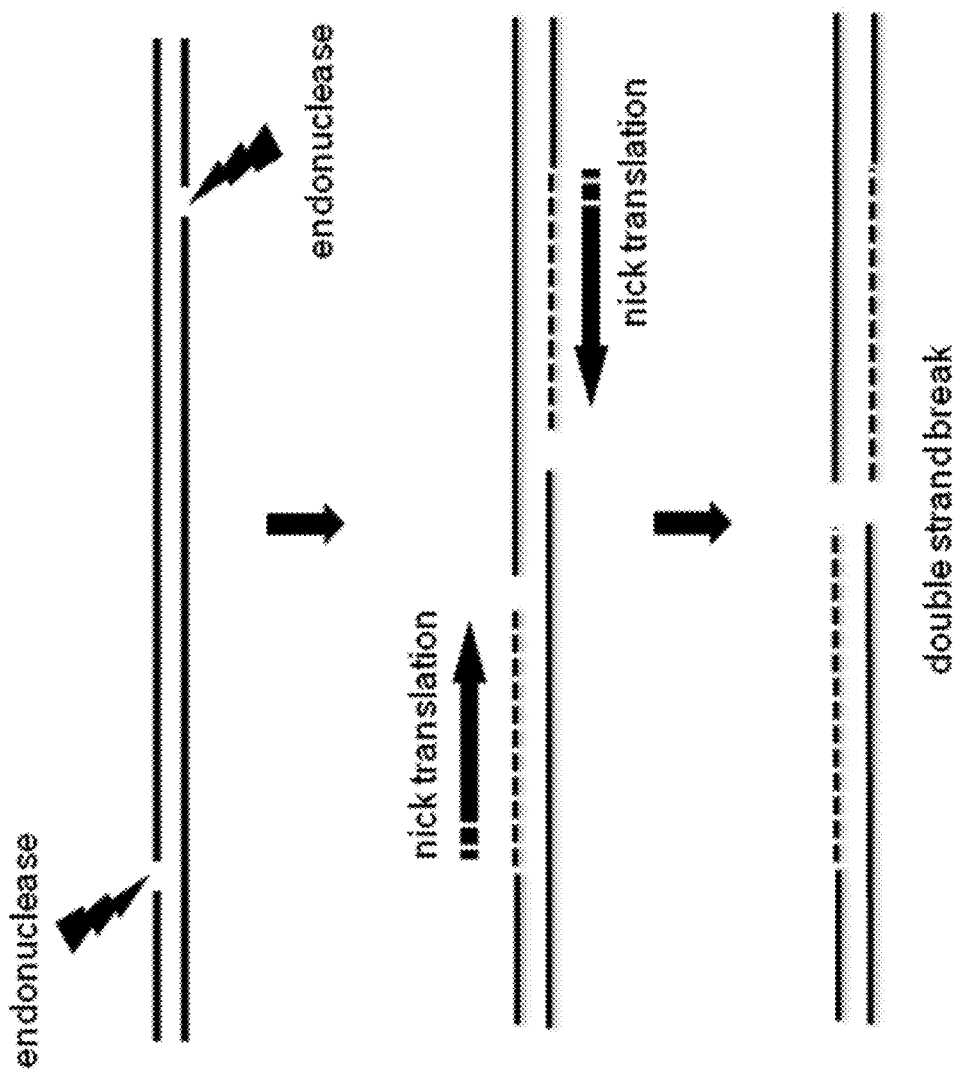
FIG. 1 is a schematic depicting non-limiting embodiments of a nucleic acid fragmenting method.

The section headings used herein are for organizational purposes only and are not to be construed as limiting the described subject matter in any way. All literature and similar materials cited in this application, including but not limited to, patents, patent applications, articles, books, treatises, and internet web pages are expressly incorporated by reference in their entirety for any purpose. When definitions of terms in incorporated references appear to differ from the definitions provided in the present teachings, the definition provided in the present teachings shall control. Unless defined otherwise, all technical and scientific terms used herein have the same meaning as is commonly understood by one of ordinary skill in the art to which these inventions belong. All patents, patent applications, published applications, treatises and other publications referred to herein, both supra and infra, are incorporated by reference in their entirety. If a definition and/or description is set forth herein that is contrary to or otherwise inconsistent with any definition set forth in the patents, patent applications, published applications, and other publications that are herein incorporated by reference, the definition and/or description set forth herein prevails over the definition that is incorporated by reference. It will be appreciated that there is an implied "about" prior to the temperatures, concentrations, times, etc discussed in the present teachings, such that slight and insubstantial deviations are within the scope of the present teachings herein. In this application, the use of the singular includes the plural unless specifically stated otherwise. Also, the use of "comprise", "comprises", "comprising", "contain", "contains", "containing", "include", "includes", and "including" are not intended to be limiting. As used herein, the terms "comprises," "comprising," "includes," "including," "has," "having" or any other variation thereof, are intended to cover a non-exclusive inclusion. For example, a process, method, article, or apparatus that comprises a list of features is not necessarily limited only to those features but may include other features not expressly listed or inherent to such process, method, article, or apparatus. Further, unless expressly stated to the contrary, "or" refers to an inclusive-or and not to an exclusive- or. For example, a condition A or B is satisfied by any one of the following: A is true (or present) and B is false (or not present), A is false (or not present) and B is true (or present), and both A and B are true (or present). It is to be understood that both the foregoing general description and the following detailed description are exemplary and explanatory only and are not restrictive of the invention.

Definitions

Unless otherwise defined, scientific and technical terms used in connection with the present teachings described herein shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used, for example, for nucleic acid purification and preparation, chemical analysis, recombinant nucleic acid, and oligonucleotide synthesis. Enzymatic reactions and purification techniques are performed according to manufacturer's specifications or as commonly accomplished in the art or as described herein. The techniques and procedures described herein are generally performed according to conventional methods well known in the art and as described in various general and more specific references that are cited and discussed throughout the instant specification. See, e.g., Sambrook et al., *Molecular Cloning: A Laboratory Manual* (Third ed., Cold Spring Harbor Laboratory Press, Cold Spring Harbor, N.Y. 2000). The nomenclatures utilized in connection with, and the laboratory procedures and techniques described herein are those well known and commonly used in the art.

As utilized in accordance with exemplary embodiments provided herein, the following terms, unless otherwise indicated, shall be understood to have the following meanings:

As used herein, when used in reference to a nucleic acid, the term "double stranded" does not necessarily require that the nucleic acid molecule be double stranded across its entire length; instead, some single stranded regions (or unhybridized regions) may still be present in the double stranded nucleic acid. Typically, at least 50% of the nucleotides within a double stranded nucleic acid undergo base pairing according to the Watson Crick paradigm; in another typical example, at least some of the nucleotides will undergo base pairing according to a different (i.e., non Watson-Crick) model. In some embodiments, a double stranded nucleic acid includes a pair of single stranded nucleic acids that interact with each other so that at least a portion of one of the single stranded molecules hybridizes with a corresponding portion of the other single stranded nucleic acid.

As used herein, when used in reference to a nucleic acid, the term "fragmenting", includes any process or operation whereby a nucleic acid is physically separated to form at least two nucleic acid fragments. In some embodiments, the nucleic acid to be fragmented can be single stranded or double stranded. In some embodiments, the nucleic acid fragments that are formed are single stranded or double stranded. In some embodiments, a nucleic acid fragment includes a segment or portion of a single-stranded or double-stranded deoxyribonucleic acid or ribonucleic acid. The nucleic acid fragments derived from fragmentation of a given nucleic acid need not include, either singly or collectively, all of the sequence of the given nucleic acid. In some embodiments, fragmentation can include cleavage of a nucleic acid through formation of a double stranded break.

A "double stranded break" in a nucleic acid molecule includes any examples of double stranded nucleic acid having a first nick in a first strand and a second nick in a second strand, where the first and second nicks are either in complete alignment or in sufficiently close proximity to allow the physical separation of the double stranded nucleic acid into two double stranded nucleic acid fragments. Introducing a break into a double stranded nucleic acid results in the formation of two new terminal ends (e.g., upstream and downstream terminal ends) at the break site. In some embodiments, the upstream and downstream terminal ends of a break can include any combination of blunt ends, 5' overhang ends and/or 3' overhang ends. In some embodiments, one strand of a double stranded nucleic acid can lack a phosphodiester bond between adjacent nucleotides, while the other strand can also lack a phosphodiester bond between adjacent nucleotides at that same location or at nearly the same location, so as to create a double stranded break. In some embodiments, a single stranded nucleic acid can lack a phosphodiester bond between adjacent nucleotides, so as to create a single stranded break. In some embodiments, a phosphodiester bond includes analog linkages that join adjacent nucleotides (or join nucleotide analogs).

As used herein, the term "nicking" includes any suitable process or treatment whereby the linkage between two adjacent or contiguous nucleotides in one nucleic acid strand of a double stranded nucleic acid is broken or disrupted, while the two corresponding nucleotides opposite the nick in the opposing strand remain linked. In some embodiments, the double stranded nucleic acid includes two strands, each having a 5' end and a 3' end (or equivalent thereof) that are substantially complementary across at least some portion of their respective lengths. Introducing a nick into one strand (referred to herein as the "nicked" strand) results in the formation of a new 5' end and a new 3' end at the position of the nick and the formation of two new strands derived from the nicked strand. These two new strands typically remain aligned and attached to the opposing strand through base pairing interactions (the opposing strand can be free of any nicks, or may include one or more nicks at other positions). In some embodiments, in a double stranded nucleic acid, nicking can include breaking a phosphodiester bond between adjacent nucleotides of one of the nucleic acid strands, while the other strand has adjacent nucleotides joined by a phosphodiester bond at the position opposite the break. In some embodiments, a nicking agent can break a phosphodiester bond (or any other equivalent bond in the case of nucleic acid molecules incorporating nucleotide analogs) at a random or at a site-specific position on at least one strand of a double stranded molecule. In some embodiments, a phosphodiester bond includes analog linkages that join adjacent nucleotides (or join nucleotide analogs). In some embodiments, double stranded nucleic acids can be enzymatically or chemically nicked.

As used herein, the term "nicking conditions" can include any condition that is suitable for generating a nick in a nucleic acid. In some embodiments, nicking conditions include enzymatic or chemical reaction conditions, where the resulting reaction breaks or disrupts at least one covalent bond between any two or more contiguous nucleotides in the nucleic acid strand. In some typical embodiments, the nicking reaction can be performed on a double stranded nucleic acid substrate having two strands that are substantially complementary to each other over at least some portion of their length, at least one strand including two contiguous nucleotides linked to each other through a phosphodiester bond that is disrupted or broken during the nicking process. Typically, the two corresponding nucleotides in the opposing or complementary strand remain linked to each other. For example, the nick can be generated between adjacent nucleotides on one strand of a double stranded nucleic acid, while the other strand has adjacent nucleotides joined by a phosphodiester bond at the position opposite the break. In some embodiments, the nucleic acid substrate can include synthetic nucleotides that are not linked to each other by phosphodiester bonds but instead by at least one other type of bond that is disrupted or broken as a result of the nicking process. In some embodiments, nicking conditions can include nicking both strands of a double stranded nucleic acid, where at least some of the nicks are located opposite corresponding nucleotides in the opposing or complementary strand that remain joined. In a nick translation reaction, if one or more nicks are translated towards each other, a double-stranded break can be formed when the two nicks come into close proximity or into complete alignment. In some embodiments, nicking conditions include contact or mixture with a nicking enzyme, which can optionally have endonuclease activity. In some embodiments, a nicking enzyme can be wild-type or mutant form. In some embodiments, nicking conditions can include contact, treatment or mixture with a compound that nicks nucleic acids, including: 1,2,4-benzenetriol, gallic acid, caffeic acid or gossypol in the presence of copper; or chromium (VI) with hydrogen peroxide.

As used herein, the term "nick translation", "nick translating" and its variants, can include any process or treatment whereby the position of a nick within a nucleic acid strand is effectively moved to a new position in a nucleic acid strand. Nick translation typically includes extension of one new strand accompanied by digestion or erosion of the other new strand. In some embodiments, nick translation includes polymerization of nucleotides or nucleotide analogs onto the new 3' end as well as digestion or erosion of nucleosides from the new 5' end. With each successive nucleotide polymerization onto the new 3' end, the position of the nick is effectively moved by one nucleotide position along the nicked strand. Nick translation can optionally continue until the nick is translated to the end of the nicked strand, or until the translated nick comes into either complete alignment or into sufficiently close proximity to another nick in the opposing strand as to form a double stranded break, resulting in the generation of two nucleic acid fragments derived from the original double stranded nucleic acid. The double stranded break may generate two new blunt ends or two new overhang ends (e.g., "sticky" ends) in the resulting nucleic acid fragments.

As used herein, the term "nick translation conditions", and its variants, can include any suitable condition for moving the position of a nick in one strand of a double stranded nucleic acid to a new position within the strand. In some embodiments, conventional nick translation conditions employ two enzymes that couple nucleic acid nicking and nick translating activities in the presence of nucleotides labeled with a detectable moiety (e.g., radioactively labeled nucleotides) to produce end-labeled nucleic acids. Of particular interest are nick translation reactions including nicking and nick translating activities in the presence of unlabeled nucleotides, resulting in the production of unlabeled nucleic acid fragments, where a sample of nucleic acids are subjected to such nick translation within the same reaction vessel. In some embodiments, methods for generating a population of nucleic acid fragments conducted according to the present teachings comprise nick translation conditions employing one or more enzymes that couple nucleic acid nicking and nick translating activities in the presence of nucleotides that lack a detectable moiety, or in the presence of labeled nucleotides. In some embodiments, nick translation conditions conducted according to the present teachings produce unlabeled nucleic acid fragments. For example, the present teachings can include nick translation conditions comprising a nicking enzyme (e.g., DNase I) and a polymerase having 5'→3' degradation/polymerization activity, or can include a nicking enzyme (e.g., DNase I) and a polymerase having 5'→3' strand displacing activity (e.g., Taq polymerase). A nick translation reaction according to the present teachings can further include one or more unlabeled nucleotides (e.g., dATP, dTTP, dCTP, dGTP, dUTP, or analogs thereof). A nick translation reaction can include a cation, such as magnesium, manganese or calcium.

DESCRIPTION OF VARIOUS EMBODIMENTS

In some embodiments, the present teachings provide compositions, systems, methods and kits for generating a population of nucleic acid fragments. Fragmentation can be at random locations in a nucleic acid. Fragmentation can be catalyzed by one or more enzymes. In some embodiments, the present teachings provide fragmenting nucleic acids comprising two or more enzymatic reactions. In some embodiments, methods for generating a population of nucleic acid fragments can include a nucleic acid nicking reaction, a nick translation reaction, or both. A nicking reaction can introduce nicks at one or more positions on either strand of a double-stranded nucleic acid. A nick translation reaction can move the position of a first nick on one strand to a new position that can be aligned with a second nick, break, or other gap in the other strand. Alignment of nicks, breaks, or gaps can result in double-stranded breaks or fragmentation points. A nicking and/or nick translating reaction can be conducted on nucleic acids in solution.

In some embodiments the disclosed methods for generating a population of nucleic acid fragments can be practiced on any suitable nucleic acid sample, including a sample comprising DNA, cDNA, RNA, RNA/DNA hybrids, and nucleic acid analogs.

Methods for generating a population of nucleic acid fragments can be conducted with unlabeled nucleotides.

Compositions, systems, methods and kits disclosed herein for generating a population of nucleic acid fragments for use in preparing nucleic acids for sequencing. Nucleic acid sequencing techniques, platforms, and systems for which this disclosure is useful include, among others, sequencing-by-synthesis, chemical degradation sequencing, ligation-based sequencing, hybridization sequencing, pyrophosphate detection sequencing, capillary electrophoresis, gel electrophoresis, next-generation, massively parallel sequencing platforms, sequencing platforms that detect hydrogen ions or other sequencing by-products, and single molecule sequencing platforms. DNA fragments can be generated to have any desired size or size range, including sizes useful for preparing the nucleic acid for sequencing with any of the aforementioned sequencing techniques, platforms, and/or systems.

Many next-generation or massively parallel sequencing systems involve the generation of nucleic acid libraries, which often comprise numerous fragments of larger nucleic acids that are to be sequenced. For example, many next-generation sequencing systems use fragment libraries, which comprise a collection of nucleic acid fragments which can be used as sequencing templates. Other types of libraries used in or for next-generation sequencing include mate pair libraries, RNA libraries (e.g., mRNA libraries, RNA-Seq libraries, whole transcriptome libraries, cell-specific RNA libraries), chromatin immunoprecipitation (ChIP) libraries, exome libraries and methylated DNA libraries.

The compositions, systems, methods, and kits disclosed herein can be useful for preparing nucleic acid libraries for use with any next-generation sequencing system, including: sequencing by oligonucleotide probe ligation and detection (e.g., SOLiD™ from Life Technologies, WO 2006/084131), probe-anchor ligation sequencing (e.g., Complete GeGenomics™ or Polonator™), sequencing-by-synthesis (e.g., Genetic Analyzer and HiSeq™, from Illumina), pyrophosphate sequencing (e.g., Genome Sequencer FLX from 454 Life Sciences), ion-sensitive sequencing (e.g., Personal Genome Machine and Proton from Ion Torrent Systems, Inc.), and single molecule sequencing platforms (e.g., HeliScope™ from Helicos™). The size or size range of DNA fragments can be selected for use in preparing the nucleic acid for sequencing on any of the aforementioned sequencing techniques and systems.

In some embodiments, compositions, systems, methods and kits disclosed herein can be used in a workflow for constructing a nucleic acid library for sequencing in an oligonucleotide probe ligation and detection system (e.g., SOLiD™ from Life Technologies) or for ion-sensitive sequencing (e.g., Personal Genome Machine and Proton from Ion Torrent Systems, Inc.). Nucleic acid starting material can be any nucleic acid (for example, DNA, cDNA, RNA, RNA/DNA hybrids, etc.), can be chromosomal, genomic, transcriptomic, organellar, methylated, chromatin-linked, cloned, unamplified or amplified, natural or synthetic, and can be isolated from any source (for example, from an organism, normal or diseased cells or tissues, body fluids, archived tissue (e.g., tissue archived in formalin and/or in paraffin), Nucleic acid starting material can be randomly fragmented according the methods disclosed herein to generate fragmented DNA useful for preparing sequencing libraries.

Compositions, systems, methods and kits disclosed herein can be used to generate a population of nucleic acid fragments that are selected to have any desired size or size range, including, for example, from about 100 to about 250 bp in length for use in preparing a SOLiD™ fragment library, from about 100 to about 300 bp in length for use in preparing an Ion Torrent PGM™ fragment library, or from about 0.8 kb to about 1.4 kb in length for preparing a SOLiD™ mate pair library. Nucleic acid fragments can also be generated with sizes or size ranges appropriate for RNA libraries (e.g., mRNA libraries, RNA-Seq libraries, whole transcriptome libraries, cell-specific RNA libraries), chromatin immunoprecipitation (ChIP) libraries, and methylated DNA libraries.

At least one molecule in a population of nucleic acid fragments can be joined to an oligonucleotide adaptor. For example, a fragmented DNA can be joined to an adaptor to conduct a primer extension reaction, amplification of the fragment, or for attachment to particles (e.g., beads), or any combination thereof. An adaptor that is joined to a fragmented DNA can anneal to an oligonucleotide capture primer which is attached to a particle, and a primer extension reaction can be conducted to generate a complementary copy of the fragmented nucleic acid attached to the particle or surface, thereby attaching a fragmented nucleic acid to a surface or particle. Adaptors can have one or more amplification primer hybridization sites, sequencing primer hybridization sites, barcode sequences, or any combinations thereof. In some embodiments, DNA fragments can be joined to one or more SOLiD™-compatible or Ion Torrent PGM™-compatible or Ion Torrent Proton™-compatible adaptors to construct a fragment library.

Figure 3:
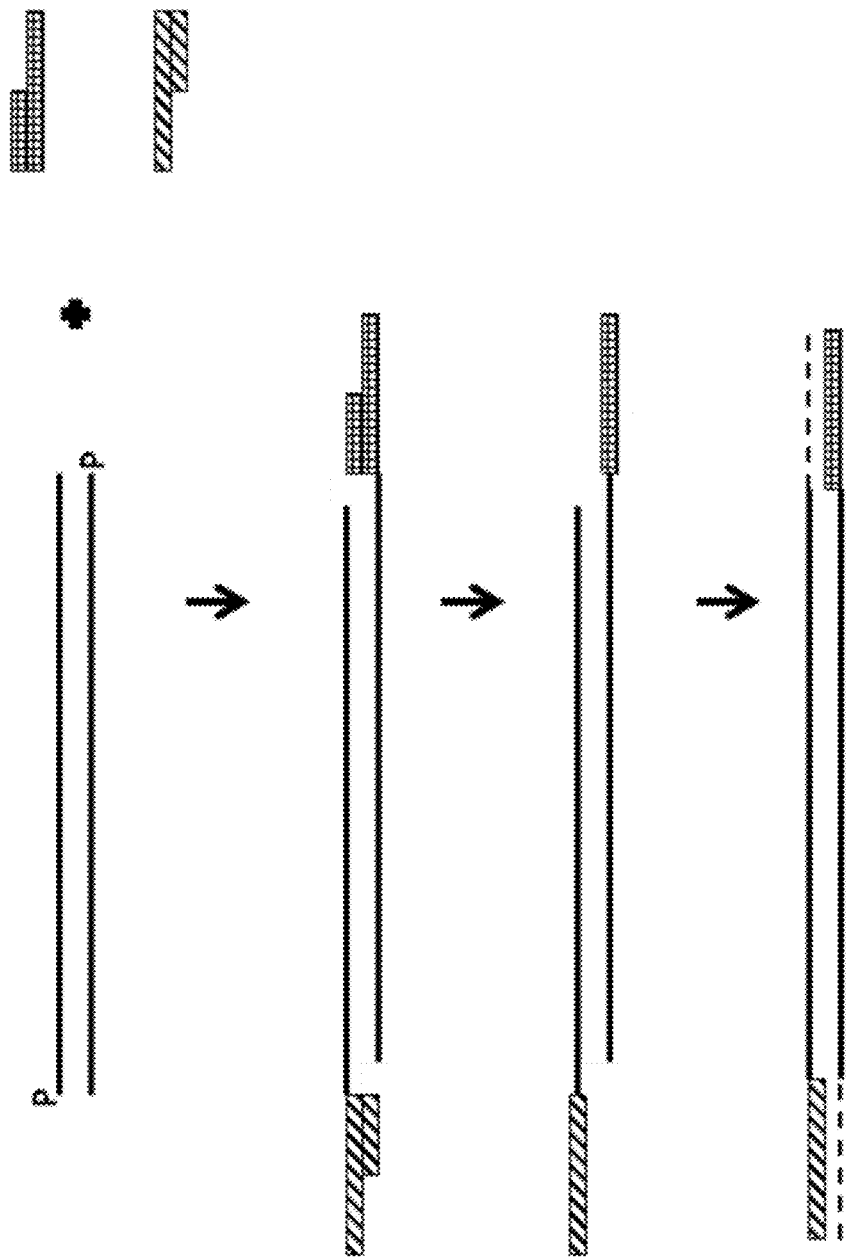
FIG. 3 is a schematic depicting non-limiting embodiments of a nucleic acid adaptor-ligation method.

Double-stranded nucleic acids can be fragmented by enzymatically nicking either strand at one or more positions and nick translating one or more of the nicks to move the position of the nick to align with a nick, break or gap on the opposite strand. Alignment of a nick on one strand with a nick, break, or gap on the other strand can generate a double-stranded nick, break or gap, which can release a double-stranded fragment from the source nucleic acid. Placement of multiple nicks into either or both strands of a nucleic acid, followed by translation of the nicks to positions in alignment with nicks, breaks, or gaps in the opposing strand can yield multiple fragments (e.g., a population of fragments) from the source nucleic acid. In some embodiments, double-stranded nucleic acids can be fragmented by enzymatically nicking either strand at one or more positions to produce blunt-ended nucleic acids fragments. The blunt-ended fragments can possess a terminal 5' phosphate and at least one end can be ligated to an adaptor to form adaptor-double stranded nucleic acid molecules. The adaptor-double stranded nucleic acid molecules can include a nick in each nucleic acid strand opposite the ligated 5' phosphate. Denaturing the adaptor-double stranded nucleic acid molecules can remove the unligated portion of the adaptor and a nick repair enzyme, such as a nick repair polymerase, can be used to fill-in the overhang thereby generating double stranded fragments from a nucleic acid source (FIG. 3).

In some embodiments, a method according to this disclosure can comprise: (a) nicking the nucleic acids; and (b) nick translating the nicks. In some embodiments, a method according to this disclosure can comprise (a) enzymatically nicking double-stranded nucleic acids on either strand at random positions; and (b) nick translating the nicks so as to move the position of the nicks on opposite strands into alignment, thereby generating a double-stranded break. In some embodiments, enzymatic nicking can be conducted with an enzyme having endonuclease activity. In some embodiments, nick translating can be a reaction that couples a 5' to 3' DNA polymerization/degradation reaction, or a reaction that couples a 5' to 3' DNA polymerization/strand displacement reaction. In some embodiments, the method can further comprise contacting the fragmented nucleic acid with a non-template-dependent terminal transferase enzyme (e.g., tailing reaction). In some embodiments, the method can further comprise contacting the nucleic acid with a phosphotransferase enzyme. In some embodiments, any combination of reactions, including nicking, nick translating, tailing and/or phosphotransferase reactions, can be conducted on nucleic acids in solution. In some embodiments, the method can further comprise contacting the double stranded gap nucleic acids with adaptors. In some embodiments, the method can further comprise contacting the double stranded gap nucleic acids with one or more nick repair enzymes. In some embodiments, a double stranded nucleic acid can be double stranded DNA, double stranded RNA or double stranded DNA/RNA hybrid.

In some embodiments, the present teachings provide methods for randomly fragmenting double-stranded nucleic acids to generate a population of nucleic acid fragments, comprising the steps: (a) enzymatically nicking either strand at random positions; and (b) nick translating the nicks so as to move the position of the nicks on opposite strands into alignment, thereby generating a double-stranded break. In some embodiments, the enzymatic nicking can be conducted with an enzyme having endonuclease activity. In some embodiments, the nick translating can be a reaction that couples a 5' to 3' DNA polymerization/degradation reaction, or a reaction that couples a 5' to 3' DNA polymerization/strand displacement reaction. In some embodiments, the method can further comprise contacting the fragmented nucleic acid with a non-template-dependent terminal transferase enzyme. In some embodiments, the method can further comprise contacting the nucleic acid with a phosphotransferase enzyme. In some embodiments, any combination of reactions, including nicking, nick translating, tailing and/or phosphotransferase reactions, can be conducted on nucleic acids in solution. In some embodiments, the method can further comprise contacting the double stranded nucleic acid fragments with oligonucleotide adaptors. In some embodiments, the method can further comprise contacting the double stranded nucleic acid fragments with one or more nick repair enzymes. In some embodiments, a double stranded nucleic acid can be double stranded DNA, double stranded RNA or double stranded DNA/RNA hybrid.

In some embodiments, the present teachings provide methods for to generate a population of nucleic acid fragments comprising the steps: (a) providing a double-stranded nucleic acid having a first and second nucleic acid strand; (b) nicking the first nucleic acid strand at a first position and nicking the second nucleic acid strand at a second position, wherein the first and second positions are at different locations on the double-stranded nucleic acid; and (c) moving the position of the first nick and the position of the second nick into alignment along the double-stranded nucleic acid, thereby generating a double-stranded break. In some embodiments, the nicking can be conducted with an enzyme having endonuclease activity. In some embodiments, the moving the position of the first nick and the position of the second nick can be conducted with a nick translation reaction. In some embodiments, the nick translation reaction can be a reaction that couples a 5' to 3' DNA polymerization/degradation reaction, or a reaction that couples a 5' to 3' DNA polymerization/strand displacement reaction. In some embodiments, the method can further comprise contacting the fragmented nucleic acid with a non-template-dependent terminal transferase enzyme. In some embodiments, the method can further comprise contacting the nucleic acid with a phosphotransferase enzyme. In some embodiments, any combination of reactions, including nicking, nick translating, tailing and/or phosphotransferase reactions, can be conducted on nucleic acids in solution. In some embodiments, the method can further comprise contacting the double stranded nucleic acid fragments with oligonucleotide adaptors. In some embodiments, the method can further comprise contacting the double stranded nucleic acid fragments with one or more nick repair enzymes. In some embodiments, a double stranded nucleic acid can be double stranded DNA, double stranded RNA or double stranded DNA/RNA hybrid.

Methods for randomly fragmenting nucleic acids can be used to generate nucleic acid fragments which can be used as part of a workflow for preparing nucleic acid libraries for sequencing (e.g., next generation sequencing). Workflows can include fragmenting, adaptor joining, size selection, purification, amplification and/or attaching to a surface. It will be readily apparent to one of skill in the art that the workflow can repeat or omit any one or more of the above steps. It will also be apparent to one of skill in the art that the order and combination of steps may be modified to generate the required double-stranded nucleic acid fragments, and is not therefore limited to the exemplary workflow provided.

For example, methods for randomly fragmenting nucleic acids can generally include reacting a nucleic acid with a nicking enzyme, nick translation enzymes and co-factors. In some embodiments, randomly fragmenting nucleic acids can also include reacting nucleic acids with a non-template-dependent terminal transferase enzyme and/or a phosphotransferase enzyme. In some embodiments, randomly fragmenting nucleic acids can also include reacting nucleic acids with adaptors and a nick repair enzyme. A reaction for randomly fragmenting nucleic acids can be practiced in a reaction vessel. A reaction for randomly fragmenting nucleic acids can be practiced using a thermal-control apparatus.

Nucleic acid fragments generated by such methods can be joined to one or more oligonucleotide adaptors for library construction to be compatible with a next generation sequencing platform. An oligonucleotide adaptor can be used to attach a fragmented nucleic acid to a surface for sequencing.

In some embodiments, a reaction for randomly fragmenting nucleic acids can be practiced on a nucleic acid which can be isolated from any source, including: an organism; normal or diseased cells or tissues; body fluids; or archived tissue (e.g., tissue archived in formalin and/or in paraffin). Nucleic acids can be in any form, including chromosomal, genomic, organellar, methylated, cloned, amplified, DNA, cDNA, RNA, RNA/DNA or synthesized.

In some embodiments, a reaction for randomly fragmenting nucleic acids can include one or more nicking enzymes that catalyze nicking one strand of a double-stranded nucleic acid. For example, a nicking enzyme can have endonuclease activity. In some embodiments, a nicking enzyme can be a DNase I enzyme (FIGS. 1 and 2).

In some embodiments, a reaction for randomly fragmenting nucleic acids can include one or more enzymes that can perform a nick translation reaction that couples a 5'→3' polymerization/degradation reaction, such as *E. coli* DNA Pol I (FIG. 1). In some embodiments, a reaction for randomly fragmenting nucleic acids can include one or more enzymes that can perform a nick translation reaction that couples a 5'→3' polymerization/strand displacement reaction, such as a Taq polymerase, Tfi polymerase, or phi29 polymerase.

Figure 2:
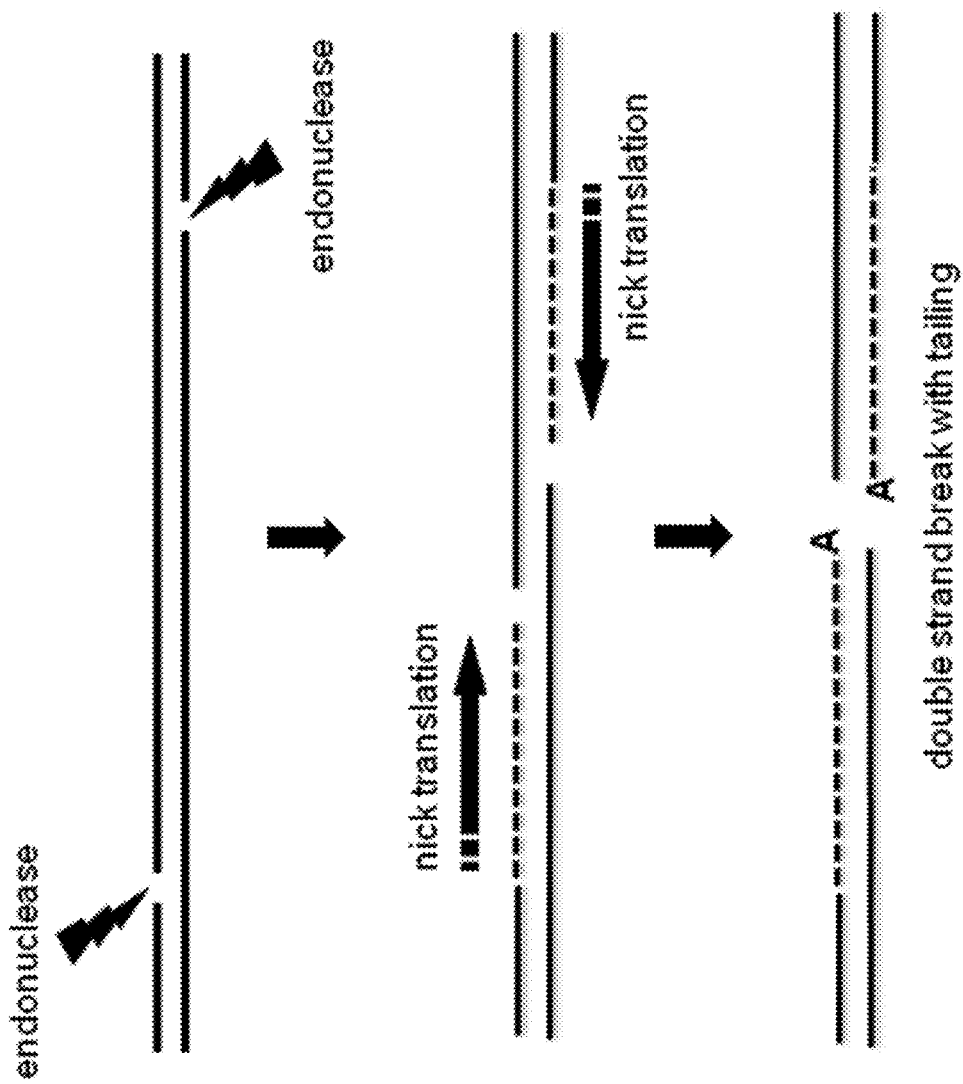
FIG. 2 is a schematic depicting non-limiting embodiments of a nucleic acid fragmenting method.

In some embodiments, a non-template-dependent terminal transferase reaction can be catalyzed by one or more enzymes in the presence of a plurality of nucleotides (FIG. 2). In some embodiments, a non-template-dependent terminal transferase reaction can be catalyzed by a Taq polymerase, Tfi DNA polymerase, 3' exonuclease minus-large (Klenow) fragment, or 3' exonuclease minus-T4 polymerase.

In some embodiments, one enzyme can catalyze a nick translation reaction and a non-template-dependent terminal transferase reaction (FIG. 2).

In some embodiments, one or more oligonucleotide adaptors can be ligated to the fragmented nucleic acids to form adaptor-double stranded nucleic acid molecules (FIG. 3).

In some embodiments, an adaptor-double stranded nucleic acid molecule can be denatured such that the non-ligated portion of the adaptor is removed and one or more nick repair enzymes, such as a nick repair polymerase, for example Taq DNA polymerase, Bst DNA polymerase, Platinum® Pfx DNA polymerase (Invitrogen), Tfi Exo(−) DNA polymerase (Invitrogen) or Phusion® Hot Start High-Fidelity DNA polymerase (New England Biolabs) perform a fill-in reaction (FIG. 3) to generate a double-stranded nucleic acid molecule.

In some embodiments, methods for generating a population of nucleic acid fragments can further comprise an enzyme reaction that adds a phosphate to a 5' end and/or removes a phosphate from a 3' end of nicked nucleic acids. These reactions can be conducted with one or more enzymes that catalyze addition of a phosphate group to a 5' terminus of a single-stranded or double-stranded nucleic acid (e.g., 5' side of a nick lacking a phosphate group) and/or that catalyze removal of 3' phosphoryl groups from a nucleic acid (e.g., 3' side of a nick having a phosphate group). In some embodiments, addition or removal of a phosphate group can be catalyzed by a polynucleotide kinase. A polynucleotide kinase can be a T4 polynucleotide kinase, or can be isolated from other sources (e.g., human). A polynucleotide kinase reaction can be conducted in the presence of ATP.

In some embodiments, methods for generating a population of nucleic acid fragments can be conducted in the presence of one or more co-factors. For example, a nucleic acid nicking reaction can be conducted in the presence of a cation. A cation can be magnesium, manganese or calcium.

In some embodiments, methods for generating a population of nucleic acid fragments can be conducted in any type of reaction vessel. For example, a reaction vessel includes any type of tube or well (e.g., 96-well plate).

In some embodiments, methods for generating a population of nucleic acid fragments can be practiced in any type of thermal-control apparatus. In some embodiments, a thermal-control apparatus can maintain a desired temperature, or can elevate and decrease the temperature, or can elevate and decrease the temperature for multiple cycles. In some embodiments, a thermal-control apparatus can maintain a temperature range of about 0° C.-100° C., or can cycle between different temperature ranges of about 0° C.-100° C. Examples of thermal-control apparatus include: a water bath and thermal cycler machine. Many thermal cycler machines are commercially-available, including (but not limited to) Applied Biosystems, Agilent, Eppendorf, Bio-Rad and Bibby Scientific.

In some embodiments, one or both ends of nucleic acid fragments can be joined to at least one oligonucleotide adaptor to construct a nucleic acid library. Oligonucleotide adaptors can include amplification primer sequences, sequencing primer sites and/or barcodes. Oligonucleotide adaptors can have any structure, including linear, hairpin, forked, or stem-loop. Fragmented nucleic acids can be joined to an oligonucleotide adaptor to permit attachment to particles (e.g., beads) or to a surface. For example, an oligonucleotide adaptor can include a nucleotide sequence that is complementary to an oligonucleotide capture primer that is attached to a particle or surface. An oligonucleotide capture primer can anneal to an adaptor that is joined to a fragmented nucleic acid, and a primer extension reaction can be conducted to generate a complementary copy of the fragmented nucleic acid attached to the particle or surface, thereby attaching a fragmented nucleic acid to a surface or particle. In some embodiments, fragmented nucleic acids can be joined at both ends to oligonucleotide adaptors that are complementary to different oligonucleotide capture primers which are attached to a surface for bridge amplification. Attachment of a fragmented nucleic acid to a particle or surface can be achieved by conducting a primer extension reaction or an amplification reaction in an aqueous condition. Primer extension and amplification reactions can be conducted under isothermal or thermocyclic conditions, or can be reacted in a tube, a well, an oil-and-water emulsion droplet or an agarose droplet (Yang 2010 Lab Chip 10(21): 2841-2843).

In some embodiments, one or both ends of nucleic acid fragments can be modified for attachment to a surface or particles. For example, a 5' or 3' end can be modified to include an amino group that can bind to a carboxylic acid compound on a surface or particles. A 5' end can include a phosphate group for reacting with an amine-coated surface (or particles) in the presence of a carbodiimide (e.g., water soluble carbodiimide). A nucleic acid can be biotinylated at one end to bind with an avidin-like compound (e.g. streptavidin) attached to a surface.

In some embodiments, a surface can be planar, convex, concave, or any combination thereof. A surface can be porous, semi-porous or non-porous. A surface can comprise an inorganic material, natural polymers, synthetic polymers, or non-polymeric material. A surface includes a flowcell, well, groove, channel, reservoir, filter, gel or inner walls of a capillary. A surface can be coated with an acrylamide compound. Nucleic acid fragments can be immobilized to an acrylamide compound coating on a surface.

In some embodiments, particles can have a shape that is spherical, hemispherical, cylindrical, barrel-shaped, toroidal, rod-like, disc-like, conical, triangular, cubical, polygonal, tubular, wire-like or irregular. Particles can have an iron core, or comprise a hydrogel or agarose (e.g., Sepharose™). Particles can be paramagnetic. Particles can be spherical or irregular shape. Particles can have cavitation or pores, or can include three-dimensional scaffolds. Particles can be coated with a carboxylic acid compound or an amine compound for attaching nucleic acid fragments. Particles can be coated with an avidin-like compound (e.g., streptavidin) for binding biotinylated nucleic acid fragments. In some embodiments, particles can be Ion Sphere™ particles. Particles can be deposited to a surface of a sequencing instrument. Sequencing reagents can be delivered to the deposited particles to conduct sequencing reactions.

Composition

In some embodiments, the present teachings provide a population of nucleic acid fragments prepared by nucleic acid fragmentation methods. In some embodiments, a population of nucleic acid fragments can include substantially similar-sized fragments or substantially dissimilar-sized fragments. In some embodiments, a population of nucleic acid fragments can be single-stranded or double-stranded. In some embodiments, a population of nucleic acid fragments can be DNA, RNA or chimeric DNA/RNA. In some embodiments, a population of nucleic acid fragments can have a first end and a second end. In some embodiments, a population of nucleic acid fragments can have one or more blunt ends or overhang ends. In some embodiments, a population of nucleic acid fragments can have one or more tailed ends. In some embodiments, a population of nucleic acid fragments can be chemically-modified, or joined to one or more oligonucleotide adaptors. In some embodiments, a population of nucleic acid fragments can be immobilized to a surface or particles, or can be in solution.

Methods for Generating a Population of Nucleic Acid Fragments

In some embodiments, the present teachings provide methods for randomly fragmenting nucleic acids to generate a population of nucleic acid fragments. In some embodiments, methods for randomly fragmenting nucleic acids can generate a population of unlabeled nucleic acid fragments.

Methods for generating a population of nucleic acids offer advantages over conventional fragmentation methods. For example, the methods provided by the present teachings employ enzymatic reactions which produce less oxidative damage compared to conventional shearing methods. The methods provided by the present teachings exhibit an increase in yield of fragments that are useful for further manipulations (e.g., nucleic acid ligation reactions). Other advantages include, nucleic acids can be randomly fragmented, showing little or no sequence preference, such as little or no preference for GC-rich or GC-poor sequences. Methods for generating a population of nucleic acids can be conducted in one or more reaction vessels, can be performed on very small amounts of starting material, can be performed in small reaction volume, and/or can produce tunable size ranges. These methods can also be performed manually or adapted for automated performance.

In some embodiments, the disclosure relates generally to methods (and associated compositions, kits, systems and apparatuses) for generating a population of nucleic acid fragments, comprising: introducing at least one double stranded break into a nucleic acid.

In some embodiments, the disclosure relates generally to methods (and associated compositions, kits, systems and apparatuses) for generating a population of nucleic acid fragments, comprising: subjecting a first double stranded nucleic acid to nicking conditions and to nick translating conditions.

In some embodiments, the disclosure relates generally to methods (and associated compositions, kits, systems and apparatuses) for generating a population of nucleic acid fragments, comprising: subjecting a first double stranded nucleic acid to nicking conditions, thereby generating a first nicked double stranded nucleic acid having at least one nick in each strand; nick translating at least one nick in each strand of the first nicked double stranded nucleic acid; and generating at least one double stranded break in the first nicked double stranded nucleic acid, thereby forming at least two nucleic acid fragments derived from the first double stranded nucleic acid.

In some embodiments, the disclosure relates generally to methods (and associated compositions, kits, systems and apparatuses) for generating a population of nucleic acid fragments, comprising: (a) nicking the nucleic acids; and (b) nick translating the nicks.

In some embodiments, the disclosure relates generally to methods (and associated compositions, kits, systems and apparatuses) for generating a population of nucleic acid fragments, comprising: (a) nicking a nucleic acid at least once on each strand; and (b) nick translating the nicks thereby generating a double-stranded break to produce at least one nucleic acid fragment.

In some embodiments, the disclosure relates generally to methods (and associated compositions, kits, systems and apparatuses) for generating a population of nucleic acid fragments, comprising: (a) nicking a plurality of nucleic acids at least once on each strand; and (b) nick translating the nicks thereby generating double-stranded breaks in the plurality of nucleic acids to produce a population of nucleic acid fragments.

In some embodiments, the disclosure relates generally to methods (and associated compositions, kits, systems and apparatuses) for generating a population of nucleic acid fragments, comprising: cleaving a nucleic acid by (i) nicking the nucleic acid at least once on each strand and (ii) nick translating the nicks thereby generating a double-stranded break to produce at least one nucleic acid fragment.

In some embodiments, the disclosure relates generally to methods (and associated compositions, kits, systems and apparatuses) for generating a population of nucleic acid fragments, comprising: (a) providing a double-stranded nucleic acid having a first and a second strand; (b) nicking the first strand at least once to produce a first nick and nicking the second strand at least once to produce a second nick; and (c) nick translating the first nick and the second nick thereby generating a double-stranded break to produce one or more nucleic acid fragments.

In some embodiments, the disclosure relates generally to methods (and associated compositions, kits, systems and apparatuses) for generating a population of nucleic acid fragments, comprising: (a) introducing at least one nick into each strand of a first and a second double stranded nucleic acid; (b) translating one or more nicks in each strand of the first and the second double stranded nucleic acid; and (c) generating at least one double stranded break in the first and second double stranded nucleic acid molecule, thereby forming a plurality (population) of nucleic acid fragments. The first and second double stranded nucleic acids can be subjected to the same fragmenting reaction in the same reaction vessel. Typically, the first and second nucleic acids include different nucleic acid sequences. In some embodiments, many different nucleic acid molecules in a sample are fragmented to form a population of nucleic acid fragments.

In some embodiments, one or more nicks can be introduced at random positions on either strand of a double-stranded nucleic acid.

In some embodiments, nick translating conditions can be conducted with labeled or unlabeled nucleotides. In some embodiments, at least one resulting nucleic acid fragment is unlabeled. In some embodiments, at least one resulting nucleic acid fragment is labeled.

In some embodiments, one, some, most or substantially all of the nucleic acid fragments are substantially similarly sized. The average size of the resulting nucleic acid fragments can be about 100 bp, about 200 bp, about 300 bp, about 500 bp, about 1000 bp, about 2500 bp, about 5000 bp, about 10000 bp, about 50000 bp, about 100000 bp, about 1 Mb, about 5 Mb, about 10 Mb or greater in length.

In some embodiments, a population of nucleic acid fragments can include substantially similar-sized or substantially dissimilar-sized nucleic acid fragments. For example, substantially similar-sized fragments can differ from each other by an average of about less than 50 bp, or differ from each other by an average of about 50-75 bp, or by an average of about 75-100 bp, or by an average of about 100-125 bp, or by an average of about 125-150 bp, or by an average of about 150-175 bp or more.

In some embodiments, methods for generating a population of nucleic acid fragments comprise the steps: (a) introducing one or more nicks on either strand of a double-stranded nucleic acid; and (b) moving the positions of the nicks to a new position along the double-stranded nucleic acid, under conditions suitable for introducing one or more nicks on either strand of a double-stranded nucleic acid and/or suitable for moving the positions of the nicks to a new position along the double-stranded nucleic acid.

In some embodiments, methods for generating a population of nucleic acid fragments comprise: introducing one or more nicks into a nucleic acid by subjecting a sample including a plurality of nucleic acids to nicking conditions; and generating at least one double stranded break in at least one of the nucleic acids.

In some embodiments, methods for generating a population of nucleic acid fragments comprise: (a) introducing at least one nick into a double stranded nucleic acid; and (b) forming a double stranded break in the nucleic acid by translating at least one nick. In some embodiments, the introducing includes introducing at least one nick into each strand of the double stranded nucleic acid. Optionally, the translating includes translating at least two nicks located on opposing nucleic acid strands towards each other. In some embodiments, the method can include generating a double stranded break, resulting in the formation of at least two nucleic acid fragments derived from the original double stranded nucleic acid.

In some embodiments, methods for generating a population of nucleic acid fragments comprise: (a) nicking a nucleic acid at least once on each strand; and (b) nick translating the nicks thereby generating a double-stranded break to produce nucleic acid fragments.

In some embodiments, methods for generating a population of nucleic acid fragments comprise: cleaving a nucleic acid by (i) nicking the nucleic acid at least once on each strand and (ii) nick translating the nicks thereby generating a double-stranded break to produce nucleic acid fragments.

In some embodiments, methods for generating a population of nucleic acid fragments comprise: (a) providing a double-stranded nucleic acid having a first and a second strand; (b) nicking the first strand at least once to produce a first nick and nicking the second strand at least once to produce a second nick; and (c) nick translating the first nick and the second nick towards each other, thereby generating a double-stranded break to produce nucleic acid fragments.

In some embodiments, methods for generating a population of nucleic acid fragments comprise: (a) introducing one or more nicks on each strand of a double-stranded nucleic acid; and (b) generating at least one double-stranded break by moving the positions of at least two of the nicks along their respective strands, thereby cleaving the double stranded nucleic acid into at least two nucleic acid fragments.

In some embodiments, methods for generating a population of nucleic acid fragments comprise: subjecting two or more different double stranded nucleic acids to nicking conditions, thereby forming at least two different nicked double stranded nucleic acids each including at least one nick in each strand; and translating the at least one nick in each strand so as to align the nicks on opposing strands, wherein the translating includes subjecting the at least two different nicked double stranded nucleic acids to nick translating conditions.

In some embodiments, methods for generating a population of nucleic acid fragments comprise: subjecting two or more different double stranded nucleic acids to nicking conditions, thereby forming at least two different nicked double stranded nucleic acids each including at least one nick in each strand; and cleaving the at least two different nicked double stranded nucleic acids, wherein the cleaving includes creating at least one double stranded break in each of the at least two different nicked double stranded nucleic acids, wherein the creating includes nick translating the least one nick in each strand, thereby generating a population of nucleic acid fragments.

In some embodiments, methods for generating a population of nucleic acid fragments comprise: cleaving at least two different double stranded nucleic acid molecules into nucleic acid fragments, wherein the cleaving includes introducing at least one nick into each strand of the at least two different double stranded nucleic acid molecules by subjecting the at least two different double stranded nucleic acid molecules to nicking conditions, thereby forming nicked double stranded nucleic acid molecules; and generating one or more double stranded breaks in the nicked double stranded nucleic acid molecules by nick translating one or more nicks in a first strand and one or more nicks in a second strand of the nicked double stranded nucleic acid molecule until at least two nicks on opposing strands are aligned.

In some embodiments, methods for generating a population of nucleic acid fragments comprise: subjecting two or more different double stranded nucleic acids to nicking conditions, thereby forming at least two different nicked double stranded nucleic acids, each including at least one nick in each strand; cleaving the at least two different nicked double stranded nucleic acids, wherein the cleaving includes creating at least one double stranded break in each of the at least two different nicked double stranded nucleic acids, wherein the creating includes nick translating the least one nick in each strand, thereby generating a population of nucleic acid fragments.

In some embodiments, methods for generating a population of nucleic acid fragments comprise: cleaving at least two different double stranded nucleic acid molecules into nucleic acid fragments, wherein the cleaving includes introducing at least one nick into each strand of the at least two different double stranded nucleic acid molecules by subjecting the at least two different double stranded nucleic acid molecules to nicking conditions, thereby forming nicked double stranded nucleic acid molecules; and generating one or more double stranded breaks in the nicked double stranded nucleic acid molecules by nick translating one or more nicks in a first strand and one or more nicks in the second strand of the nicked double stranded nucleic acid molecule until at least two nicks on opposing strands are aligned.

In some embodiments, a nick refers to a location on a double-stranded nucleic acid that lacks a phosphodiester bond between adjacent nucleotides of one of the nucleic acid strands, while the other strand has adjacent nucleotides joined by a phosphodiester bond at that same location. In some embodiments, a phosphodiester bond includes analog linkages that join adjacent nucleotides (or nucleotide analogs). In some embodiments, methods for generating a population of nucleic acid fragments can generate a plurality of fragments having at least one blunt-end or overhang end. In some embodiments, one or both ends of a double stranded nucleic acid fragment can be blunt ended comprising ends that are flush with each other. The terminal nucleosides at the blunt end can have base pairing or can lack base pairing. In some embodiments, one or both ends of a double stranded nucleic acid fragment can include a 5' or 3' overhang end which comprises a double stranded portion and a terminal single stranded portion.

In some embodiments, introducing one or more nicks can be catalyzed by one or more enzymes. In some embodiments, an enzyme that catalyzes nucleic acid nicking includes an enzyme having endonuclease activity. In some embodiments, introducing one or more nicks can be catalyzed by one or more enzymes in the presence of a cation. In some embodiments, a cation can include magnesium, manganese or calcium.

In some embodiments, the methods for generating a population of nucleic acid fragments can further comprise one or more nick repair enzymes, such as a nick repair polymerase. In some embodiments, the nick repair polymerase can be Taq DNA polymerase, Bst DNA polymerase, Platinum® Pfx DNA polymerase (Invitrogen), Tfi Exo(−) DNA polymerase (Invitrogen) or Phusion® Hot Start High-Fidelity DNA polymerase (New England Biolabs). For example, a nick repair reaction can be conducted in the presence of a cation. A cation can be magnesium, manganese or calcium.

In some embodiments, moving the position of the nicks can be catalyzed by one or more enzymes in the presence of a plurality of nucleotides. In some embodiments, moving the position of the nicks can be catalyzed by one or more nick translation enzymes in the presence of a plurality of nucleotides. In some embodiments, an enzyme that catalyzes nick translation includes an enzyme that couples a 5'→3' polymerization/degradation reaction, or an enzyme that couples a 5'→3' polymerization/strand displacement reaction.

In some embodiments, nicking and/or nick translating reactions can be conducted on nucleic acids in solution or on nucleic acids attached to a solid surface.

In some embodiments, methods for generating a population of nucleic acid fragments can include contacting a nucleic acid with one or more nucleic acid binding proteins at any step, or can lack a nucleic acid binding protein. In some embodiments, methods for generating a population of nucleic acid fragments can include contacting a nucleic acid with one or more of nucleic acid binding proteins in any combination with an enzyme that nicks at least one nucleic acid strand and/or with a nick translating enzyme. In some embodiments, a nicking and/or a nick translating reaction can comprise at least one nucleic acid binding protein. In some embodiments, methods for generating a population of nucleic acid fragments can include contacting a nucleic acid with one or more of nucleic acid binding proteins serially or simultaneously (or essentially simultaneously) with any combination of an enzyme that nicks at least one nucleic acid strand and/or with a nick translating enzyme. In some embodiments, the nicking step and/or the nick translating step can be conducted in the presence of at least one nucleic acid binding protein. In some embodiments, a nicking step and/or a nick translating step can be conducted in the presence of at least one nucleic acid binding protein in solution. Inclusion of a nucleic acid binding protein can improve the yield of fragmented nucleic acids and/or can reduce formation of nucleic acid fragments having rearranged portions. In some embodiments, a nucleic acid binding protein can be a single-stranded nucleic acid binding protein.

In some embodiments, a nucleic acid binding protein can be a single-stranded nucleic acid binding protein. For example, a single-stranded nucleic acid binding protein can be a phage T4 gp 32 protein, or can be from *Sulfolobus solfataricus* (e.g., Sso SSB) or from *Methanococcus jannaschii* (Mja SSB) or *E. coli* SSB protein.

In some embodiments, methods for generating a population of nucleic acid fragments can comprise a non-template-dependent terminal transferase reaction (e.g., tailing reaction). In some embodiments, a non-template-dependent terminal transferase reaction can be catalyzed by one or more enzymes in the presence of a plurality of nucleotides. In some embodiments, a non-template-dependent terminal transferase reaction can be catalyzed by one or more enzymes in the presence of one or more types of nucleotides (e.g., A, G, C, or T/U).

In some embodiments, methods for generating a population of nucleic acid fragments can further comprise an enzyme reaction that adds a phosphate to a 5' end and/or removes a phosphate from a 3' end. These reactions can be conducted with one or more enzymes that catalyze addition of a phosphate group to a 5' terminus of a single-stranded or double-stranded nucleic acid and/or that catalyze removal of 3' phosphoryl groups from a nucleic acid. In some embodiments, addition or removal of a phosphate group can be catalyzed by a polynucleotide kinase. A polynucleotide kinase can be a T4 polynucleotide kinase, or can be isolated from other sources (e.g., human). A polynucleotide kinase reaction can be conducted in the presence of ATP. In some embodiments, the method can further comprise contacting the double stranded gap nucleic acids with adaptors. In some embodiments, the method can further comprise contacting the double stranded gap nucleic acids with one or more nick repair enzymes.

In some embodiments, multiple reactions can be conducted in one reaction vessel, such as a nicking reaction and nick translation reaction, or such as a nicking reaction and nick translation reaction and a tailing reaction, or such as a nicking reaction and nick translation reaction and a tailing reaction and a polynucleotide kinase reaction, or such as a nicking reaction and ligation reaction and nick translation reaction and a nick repair reaction. In some embodiments, different reactions (e.g., nicking reaction, ligation reaction, nick translation reaction, tailing reaction, nick repair reaction and/or polynucleotide kinase reaction) can be conducted in separate reaction vessels or these different reactions can be conducted at different times in the same reaction vessel. A nucleic acid binding protein can be present in any reaction vessel during a nicking and/or nick translating step. In some embodiments, a reaction vessel can be any type of tube or well (e.g., 96-well plate). In some embodiments, different reactions (e.g., nicking reaction, ligation reaction, nick translation reaction, tailing reaction, nick repair reaction and/or polynucleotide kinase reaction) can be conducted in an oil-and-water emulsion droplet or an agarose droplet (Yang 2010 Lab Chip 10(21):2841-2843).

In some embodiments, the size range of fragments resulting from conducting a nucleic acid fragmentation reaction can be about 50-150 bp, or about 150-250 bp, or about 250-500 bp, or about 500-750 bp, or about 750-1000 bp, or about 1-2 kb, or about 2-5 kb, or about 5-8 kb, or about 8-10 kb, or about 10-20 kb, or about 20-40 kb, or about 40-60 kb, or longer. In some embodiments, the resulting average fragment size (or average size range of nucleic acid fragments) can be modulated by: adjusting the nicking conditions and/or the nick translating conditions. For example, the nicking conditions and/or the nick translating conditions can be adjusted by increasing or decreasing an enzyme concentration (e.g., nicking or nick translating enzyme); by increasing or decreasing the cation concentration; by increasing or decreasing the nucleotide concentration; by increasing or decreasing a reaction temperature, time and/or pH.

In some embodiments, the resulting average fragment size (or average size range) can be modulated by: increasing or decreasing an enzyme concentration (e.g., nicking or nick translating enzyme); by increasing or decreasing the cation concentration; by increasing or decreasing the nucleotide concentration; by increasing or decreasing a reaction temperature, time and/or pH.

In some embodiments, the number of nicks introduced on either strand of a double-stranded nucleic acid can be modulated by: increasing or decreasing an enzyme concentration; by increasing or decreasing the cation concentration; by increasing or decreasing the nucleotide concentration; by increasing or decreasing a reaction temperature, time and/or pH. In some embodiments, the nick translation reaction can be modulated by: increasing or decreasing the enzyme concentration; by increasing or decreasing the nucleotide concentration; by increasing or decreasing the cation concentration; by increasing or decreasing a reaction temperature, time and/or pH.

In some embodiments, the average number of nicks introduced into nucleic acid molecules within a mixed population of different nucleic acid molecules on either strand of a double-stranded nucleic acid can be modulated by: increasing or decreasing an enzyme concentration (e.g., DNase I); by increasing or decreasing the cation concentration (e.g., magnesium); by increasing or decreasing the nucleotide concentration; by increasing or decreasing a reaction temperature, time and/or pH.

In some embodiments, the nick repair reaction can be modulated by: increasing or decreasing the nick repair enzyme concentration; by increasing or decreasing the nucleotide concentration; by increasing or decreasing the cation concentration; by increasing or decreasing a reaction temperature, time and/or pH.

In some embodiments, methods for generating a population of nucleic acid fragments, can include the steps: (a) providing a double-stranded nucleic acid having a first and second nucleic acid strand; (b) nicking the first nucleic acid strand at a first position and nicking the second nucleic acid strand at a second position; and (c) moving the position of the first nick and the position of the second nick to a new position, under conditions suitable for nicking the first nucleic acid strand, suitable for nicking the second nucleic acid strand, suitable for moving the position of first nick, and/or suitable for moving the position of the second nick.

In some embodiments, methods for generating a population of nucleic acid fragments, can include the steps: (a) providing a double-stranded nucleic acid having a first and second nucleic acid strand; (b) nicking the first nucleic acid strand at a first position and nicking the second nucleic acid strand at a second position, wherein the first and second positions are at different locations on the double-stranded nucleic acid; and (c) moving the position of the first nick and the position of the second nick in a direction towards each other until the position of the first nick and the second nick are aligned so as to generate a double-stranded gap, thereby fragmenting the nucleic acid, under conditions suitable for nicking the first nucleic acid strand, suitable for nicking the second nucleic acid strand, suitable for moving the position of first nick, and/or suitable for moving the position of the second nick. In some embodiments, the positions of the first and second nick can be proximal to each other to cause fragmentation of the nucleic acids.

In some embodiments, methods for generating a population of nucleic acid fragments can include additional enzyme steps to improve the yield of fragments useful for further manipulations. For example, a 5' end of a nicked nucleic acid can lack a phosphate group which can inhibit ligation to another nucleic acid fragment. In another example, a 3' end of a nicked nucleic acid can have a phosphate group which can inhibit nick translation. In some embodiments, the methods can include an enzyme reaction that adds a phosphate to a 5' end and/or removes a phosphate from a 3' end of nicked nucleic acids. These reactions can be conducted with one or more enzymes that catalyze addition of a phosphate group to a 5' terminus of a single-stranded or double-stranded nucleic acid and/or that catalyze removal of 3' phosphoryl groups from a nucleic acid. In some embodiments, addition or removal of a phosphate group can be catalyzed by a polynucleotide kinase. A polynucleotide kinase can be a T4 polynucleotide kinase, or can be isolated from other sources (e.g., human). A polynucleotide kinase reaction can be conducted in the presence of ATP. In some embodiments, the can further comprise contacting the double stranded gap nucleic acids with adaptors. In some embodiments, the method can further comprise contacting the double stranded gap nucleic acids with one or more nick repair enzymes. In some embodiments, the methods can include the steps: (a) providing a double-stranded nucleic acid having a first and second nucleic acid strand; (b) nicking the first nucleic acid strand at a first position to generate a first nick and nicking the second nucleic acid strand at a second position to generate a second nick, wherein the first and second positions are at different locations on the double-stranded nucleic acid; (c) moving the position of the first nick and the position of the second nick in a direction towards each other until the position of the first nick and the second nick are aligned to generate a double-stranded gap, thereby fragmenting the nucleic acid; and (d) adding a phosphate group to a 5' terminus of the first or second nick or removing a phosphate group from a 3' end of the first or second nick, under conditions suitable for nicking the first nucleic acid strand, suitable for nicking the second nucleic acid strand, suitable for moving the position of first nick, suitable for moving the position of the second nick and/or suitable for adding a phosphate group to a 5' terminus of the first or second nick or removing a phosphate group from a 3' end of the first or second nick. In some embodiments, the positions of the first and second nick can be proximal to each other to cause fragmentation of the nucleic acids.

In some embodiments, methods for generating a population of nucleic acid fragments can generate fragments having at least one blunt-end, or can generate fragments having both ends blunt-ended. In some embodiments, nicking the first nucleic acid strand can be catalyzed by one or more enzymes.

In some embodiments, an enzyme that catalyzes nucleic acid nicking includes an enzyme having endonuclease activity. In some embodiments, nicking the first nucleic acid strand can be catalyzed by one or more enzymes in the presence of a cation. In some embodiments, nicking the second nucleic acid strand can be catalyzed by one or more enzymes. In some embodiments, nicking the second nucleic acid strand can be catalyzed by one or more enzymes in the presence of a cation. In some embodiments, a cation can include magnesium, manganese or calcium. In some embodiments, the position of the first nick and the position of the second nick can be at the same or different location on the double-stranded nucleic acid.

In some embodiments, moving the position of the first nick can be catalyzed by one or more enzymes in the presence of a plurality of nucleotides (labeled and/or unlabeled). For example, a nucleotide can be joined to a label such as a fluorescent, luminescent or radioactive moiety. In some embodiments, moving the position of the second nick can be catalyzed by one or more enzymes in the presence of a plurality of nucleotides (labeled and/or unlabeled). In some embodiments, an enzyme that catalyzes nick translation includes an enzyme that couples a 5'→3' polymerization/degradation reaction, or an enzyme that couples a 5'→3' polymerization/strand displacement reaction.

In some embodiments, methods for generating a population of nucleic acid fragments further comprise a non-template-dependent terminal transferase reaction (e.g., tailing reaction). In some embodiments, a non-template-dependent terminal transferase reaction can be catalyzed by one or more enzymes in the presence of a plurality of nucleotides (labeled or unlabeled). In some embodiments, a non-template-dependent terminal transferase reaction can be catalyzed by one or more enzymes in the presence of one or more types of nucleotides (e.g., A, G, C, T, U or analogs thereof).

In some embodiments, methods for generating a population of nucleic acid fragments can further include joining an oligonucleotide adaptor to at least one end of a fragment. For example, method for generating a population of nucleic acid fragments can include the steps: (a) generating a population of nucleic acid fragments by (i) nicking the nucleic acid at least once on each strand and (ii) nick translating the nicks thereby generating a double-stranded break to produce a population of nucleic acid fragments; and (b) joining at least one end of each of the fragments in the population to an oligonucleotide adaptor, thereby generating a nucleic acid library.

In some embodiments, the method comprises: (a) providing a double-stranded nucleic acid having a first and second nucleic acid strand; (b) nicking the first nucleic acid strand at a first position to generate a first nick and nicking the second nucleic acid strand at a second position to generate a second nick, wherein the first and second positions are at different locations on the double-stranded nucleic acid; (c) moving the position of the first nick and the position of the second nick in a direction towards each other until the position of the first nick and the second nick are aligned to generate a double-stranded gap, thereby fragmenting the nucleic acid; (d) joining an oligonucleotide adaptor to the fragmented nucleic acid; denaturing the adaptor-nucleic acid fragment; and nick repairing the nucleic acid strand opposite the site of ligation, under conditions suitable for nicking the first nucleic acid strand, suitable for nicking the second nucleic acid strand, suitable for moving the position of first nick, suitable for moving the position of the second nick, suitable for ligating the adaptor to the nucleic acid fragment and/or suitable for nick repairing the nucleic acid strand opposite the site of ligation.

In some embodiments, multiple reactions can be conducted (with or without binding to nucleic acid binding proteins) in one reaction vessel, such as a nicking reaction and nick translation reaction, or a nicking reaction and a ligation reaction, or a nicking reaction and a ligation reaction and a nick repair reaction, or such as a nicking reaction and nick translation reaction and a tailing reaction. In some embodiments, different reactions (e.g., nicking reaction, nick translation reaction, ligation reaction, nick repair reaction and/or tailing reaction) can be conducted (with or without binding to nucleic acid binding proteins) in separate reaction vessels or these different reactions can be conducted at different times in the same reaction vessel.

Additional Steps

In some embodiments, additional nucleic acid manipulations can be conducted following a fragmentation reaction(s). In some embodiments, any combination of additional reactions can be conducted in any order, and can include: chemical modification, size-selection, end repairing, tailing, adaptor-joining, ligation, nick repairing, purification, nick translation, amplification, surface attachment and/or sequencing. In some embodiments, any of these reactions can be omitted or can be repeated.

In some embodiments, nucleic acid fragmentation reactions and additional reactions can be conducted to prepare nucleic acid fragments to be used for insertion into a vector, as probes, as a source of double-stranded and single-stranded fragments, as amplification templates, or for preparing nucleic acid libraries.

In some embodiments, a population of nucleic acid fragments can be modified to attach to a surface. For example, a population of nucleic acid fragments can be amino-modified for attachment to a surface (e.g., particles or a planar surface). In some embodiments, an amino-modified nucleic acid fragment can be attached to a surface that is coated with a carboxylic acid. In some embodiments, an amino-modified nucleic acid can be reacted with EDC (or EDAC) for attachment to a carboxylic acid coated surface (with or without NHS). In some embodiments, nucleic acid fragments can be attached to particles, such as Ion Sphere™ particles (Life Technologies).

In some embodiments, a surface can be an outer or top-most layer or boundary of an object. In some embodiments, a surface can be a solid surface or semi-solid surface. In some embodiments, a surface can be porous or non-porous. In some embodiments, a surface can be a planar surface, as well as concave, convex, or any combination thereof. In some embodiments, a surface can be a bead, particle, sphere, filter, flowcell, or gel. In some embodiments, a surface includes the inner walls of a capillary, a channel, a well, groove, channel, reservoir. In some embodiments, a surface can include texture (e.g., etched, cavitated, pores, three-dimensional scaffolds or bumps). In some embodiments, a surface can be made from materials such as glass, borosilicate glass, silica, quartz, fused quartz, mica, polyacrylamide, plastic polystyrene, polycarbonate, polymethacrylate (PMA), polymethyl methacrylate (PMMA), polydimethylsiloxane (PDMS), silicon, germanium, graphite, ceramics, silicon, semiconductor, high refractive index dielectrics, crystals, gels, polymers, or films (e.g., films of gold, silver, aluminum, or diamond). In some embodiments, nucleic acid fragments can be arranged on a surface in a random pattern, organized pattern, rectilinear pattern, hexagonal pattern, or addressable array pattern.

In some embodiments, a population of nucleic acid fragments can be modified to attach to one member of a binding partner (e.g., biotin). In some embodiments, a biotinylated nucleic acid fragment can be attached to another member of a binding partner (e.g., avidin-like, such as streptavidin) which is attached to a surface.

In some embodiments, molecules that function as binding partners include: biotin (and its derivatives) and their binding partners avidin, streptavidin (and their derivatives); His-tags which bind with nickel, cobalt or copper; cysteine, histidine, or histidine patch which bind Ni-NTA; maltose which binds with maltose binding protein (MBP); lectin-carbohydrate binding partners; calcium-calcium binding protein (CBP); acetylcholine and receptor-acetylcholine; protein A and binding partner anti-FLAG antibody; GST and binding partner glutathione; uracil DNA glycosylase (UDG) and ugi (uracil-DNA glycosylase inhibitor) protein; antigen or epitope tags which bind to antibody or antibody fragments, particularly antigens such as digoxigenin, fluorescein, dinitrophenol or bromodeoxyuridine and their respective antibodies; mouse immunoglobulin and goat anti-mouse immunoglobulin; IgG bound and protein A; receptor-receptor agonist or receptor antagonist; enzyme-enzyme cofactors; enzyme-enzyme inhibitors; and thyroxine-cortisol. Another binding partner for biotin can be a biotin-binding protein from chicken (Hytonen, et al., BMC Structural Biology 7:8).

In some embodiments, a population of nucleic acid fragments can be used to generate DNA fragments that are selected to have any desired size or size range, including, for example, from about 100 to about 250 bp in length for use in preparing a SOLiD™ fragment library, from about 100 to about 300 bp in length for use in preparing an Ion Torrent PGM™ fragment library, or from about 0.8 kb to about 1.4 kb in length for preparing a SOLiD™ mate pair library, or about 100 to about 60 kb in length for any type of nucleic acid library. DNA fragments can also be generated with sizes or size ranges appropriate for RNA libraries (e.g., mRNA libraries, RNA-Seq libraries, whole transcriptome libraries, cell-specific RNA libraries), chromatin immunoprecipitation (ChIP) libraries, and methylated DNA libraries.

Library Preparation Methods

In some embodiments, a population of nucleic acid fragments produced by the present teachings can be used to prepare any type of nucleic acid library that is compatible with any type of sequencing platform including chemical degradation, chain-termination, sequence-by-synthesis, pyrophosphate, massively parallel, ion-sensitive, and single molecule platforms. For example, a sequencing platform can include any type of sequencing reaction, including: Maxam Gilbert, Sanger, capillary electrophoresis (e.g., Applied Biosystems, now part of Life Technologies), or any type of next generation sequence platform, including oligonucleotide probe ligation sequencing (e.g., SOLiD), probe-anchor ligation sequencing (e.g., Complete Genomics or Polonator), sequence by synthesis (e.g., Illumina, Helicos), pyrophosphate sequencing (e.g., 454/Roche), and ion-sensitive sequencing (e.g., Ion Personal Genome Machine™, produced by Ion Torrent Systems, Inc., a subsidiary of Life Technologies Corp, Carlsbad, Calif.).

In some embodiments, additional nucleic acid manipulations can be conducted following a fragmentation reaction(s), including any combination of additional reactions can be conducted in any order, and can include: chemical modification, size-selection, end repairing, tailing, ligation, nick repairing, adaptor-joining, purification, nick translation, amplification surface attachment and/or sequencing. In some embodiments, any of these reactions can be omitted or can be repeated.

In some embodiments, a nucleic acid fragmentation reaction can include: size-selection, adaptor-joining, and nick translation. In some embodiments, a nucleic acid fragmentation reaction can include: size-selection, adaptor-joining, nick translation and amplification. In some embodiments, a nucleic acid fragmentation reaction can include: ligation, nick repair reaction and size selection. In some embodiments, a nucleic acid fragmentation reaction can include: ligation, nick repair reaction, size selection and amplification. In some embodiments, a nucleic acid fragmentation reaction can include: purification, ligation, nick repair reaction, purification and size selection. In some embodiments, a nucleic acid fragmentation reaction can include: size selection, ligation, nick repair reaction, purification and size selection.

In some embodiments, amplification can include thermocycling amplification or isothermal amplification reactions. In some embodiments, amplification can be conducted with polymerase that are thermo-stable or thermo-labile. In some embodiments, amplification can be conducted as a PCR reaction.

In some embodiments, nucleic acid fragments produced by the present teachings can result in advantages over the teachings of the prior art. For example, nucleic acid fragments produced by the present teachings can result in increased yield. In some embodiments, the nucleic acid fragments produced by the present teachings are generated in a more efficient manner and therefore decrease the amount of time required to produce the fragmented nucleic acid library. In some embodiments, the nucleic acid fragments produced by the teachings of the present disclosure are sufficient in yield to be used in a downstream application without an amplification step. For example, nucleic acid fragments produced by the present teachings can be directly incorporated into a downstream template preparation step, such as the Ion Xpress™ Template Kit using an Ion Torrent™ PGM system (e.g., PCR-mediated addition of the nucleic acid fragment library onto Ion Sphere™ Particles) (Life Technologies, Part No. 4467389). For example, instructions to prepare a template library from the nucleic acid fragment library can be found in the Ion Xpress Template Kit User Guide (Life Technologies, Part No. 4465884), hereby incorporated by reference in its entirety. Instructions for loading the template library onto the Ion Torrent™ Chip for sequencing are described in the Ion Sequencing User Guide (Part No. 4467391), hereby incorporated by reference in its entirety.

Size-Selection:

In some embodiments, a population of nucleic acid fragments can be subjected to any size-selection procedure to obtain any desired size range. In some embodiments, a population of nucleic acid fragments is not size-selected. In some embodiments, nucleic acid fragments generated by practicing the present teachings can be size-selected to produce a population of nucleic acid fragments.

In some embodiments, nucleic acid size selection method includes without limitation: solid phase adherence or immobilization; electrophoresis, such as gel electrophoresis; and chromatography, such as HPLC and size exclusion chromatography. In some embodiments, a solid phase adherence/immobilization methods involves paramagnetic beads coated with a chemical functional group that interacts with nucleic acids under certain ionic strength conditions with or without polyethylene glycol or polyalkylene glycol.

Examples of solid phase adherence/immobilization methods include but are not limited to: SPRI (Solid Phase Reversible Immobilization) beads from Agencourt (see Hawkins 1995 Nucleic Acids Research 23:22) which are carboxylate-modified paramagnetic beads; MAGNA PURE magnetic glass particles (Roche Diagnostics, Hoffmann-La Roche Ltd.); MAGNESIL magnetic bead kit from Promega; BILATEST magnetic bead kit from Bilatec AG; MAGTRATION paramagnetic system from Precision System Science, Inc.; MAG BIND from Omega Bio-Tek; MAGPREP silica from Merck/Estapor; SNARe DNA purification system from Bangs; CHEMAGEN M-PVA beads from CHEMAGEN; and magnetic beads from Aline Bioscience (DNA Purification Kit).

In some embodiments, size-selected nucleic acid fragments can be about 50-250 bp, or about 250-500 bp, or about 500-750 bp, or about 750-1000 bp, or about 1-5 kb, or about 5-10 kb, or about 10-25 kb, or about 25-50 kb, or about 50-60 kb or longer.

Repairing Nucleic Acid Fragments:

In some embodiments, repairing a population of nucleic acid fragments may be desirable. In some embodiments, a nucleic acid fragment from a population can have a first end, a second end, or an internal portion, having undesirable features, such as nicks, overhang ends, ends lacking a phosphorylated end, ends having a phosphorylated end, or nucleic acid fragments having apurinic or apyrimidinic residues. In some embodiments, enzymatic reactions can be conducted to repair one or more ends or internal portions. In some embodiments, nucleic acid fragments can be subjected to enzymatic reactions to convert overhang ends to blunt ends, or to phosphorylate or de-phosphorylate the 5' end of a strand, or to close nicks, to repair oxidized purines or pyrimidines, to repair deaminated cytosines, or to hydrolyze the apurinic or apyrimidinic residues. In some embodiments, repairing or end-repairing nucleic acid fragments includes contacting nucleic acid fragments with: an enzyme to close single-stranded nicks in duplex DNA (e.g., T4 DNA ligase); an enzyme to phosphorylate the 5' end of at least one strand of a duplex DNA (e.g., T4 polynucleotide kinase); an enzyme to remove a 5' or 3' phosphate (e.g., any phosphatase enzyme, such as calf intestinal alkaline phosphatase, bacterial alkaline phosphatase, shrimp alkaline phosphatase, Antarctic phosphatase, and placental alkaline phosphatase); an enzyme to remove 3' overhang ends (e.g., DNA polymerase I, Large (Klenow) fragment, T4 DNA polymerase, mung bean nuclease); an enzyme to fill-in 5' overhang ends (e.g., T4 DNA polymerase, Tfi DNA polymerase, Tli DNA polymerase, Taq DNA polymerase, Large (Klenow) fragment, phi29 DNA polymerase, Mako DNA polymerase (Enyzmatics, Beverly, Mass.), or any heat-stable or heat-labile DNA polymerase); an enzyme to remove 5' overhang ends (e.g., S1 nuclease); an enzyme to remove 5' or 3' overhang ends (e.g., mung bean nuclease); an enzyme to hydrolyze single-stranded DNA (e.g., nuclease P1); an enzyme to remove both strands of double-stranded DNA (e.g., nuclease Bal-31); and/or an enzyme to remove an apurinic or apyrimidinic residue (e.g., endonuclease IV). In some embodiments, the polymerases can have exonuclease activity, or have a reduced or lack exonuclease activity.

In some embodiments, a repairing or end-repairing reaction can be supplemented with additional repairing enzymes in any combination and in any amount, including: endonuclease IV (apurinic-apyrimidinic removal), Bst DNA polymerase (5'>3' exonuclease for nick translation), formamidopyrimidine DNA glycosylase (FPG) (e.g., base excision repair for oxidize purines), uracil DNA glycosylase (uracil removal), T4 endonuclease V (pyrimidine removal) and/or endonuclease VIII (removes oxidized pyrimidines). In some embodiments, a repairing or end-repairing reaction can be conducted in the presence of appropriate co-factors, including dNTPs, NAD, $(NH_4)_2SO_4$, KCl, and/or $MgSO_4$.

Adaptor-Joining

In some embodiments, a population of nucleic acid fragments (e.g., generated by any method disclosed herein) can be joined to at least one type of nucleic acid adaptor (e.g., oligonucleotide adaptor). In some embodiments, at least one end of nucleic acid fragments in a population, so generated by the disclosed methods, can be joined to one or more oligonucleotide adaptors to generate a nucleic acid library.

In some embodiments, methods for generating a population of nucleic acid fragments comprise: introducing at least one double stranded break into a sample nucleic acid so as to generate at least one nucleic acid fragment; and joining at least one end of the at least one nucleic acid fragment to one or more oligonucleotide adaptors, thereby generating a fragment-adaptor construct. In some embodiments, a fragment-adaptor construct can be part of a nucleic acid library.

In some embodiments, methods for generating a population of nucleic acid fragments comprise: subjecting a sample nucleic acid to nicking conditions; subjecting the sample nucleic acid to nick translation conditions so as to generate nucleic acid fragments; and joining at least one end of the nucleic acid fragments to one or more oligonucleotide adaptors, thereby generating fragment-adaptor constructs. In some embodiments, the fragment-adaptor constructs can be part of a nucleic acid library.

In some embodiments, methods for generating a population of nucleic acid fragments comprise: nicking a nucleic acid; nick translating the nicks so as to generate a nucleic acid fragment; and joining at least one end of the nucleic acid fragment to one or more oligonucleotide adaptors, thereby generating a fragment-adaptor construct. In some embodiments, a fragment-adaptor construct can be part of a nucleic acid library.

In some embodiments, methods for generating a population of nucleic acid fragments comprise: (a) generating a population of nucleic acid fragments by (i) nicking the nucleic acid at least once on each strand and (ii) nick translating the nicks thereby generating a double-stranded break to produce a population of nucleic acid fragments; and (b) joining at least one end of each of the fragments in the population to an oligonucleotide adaptor, thereby generating a nucleic acid library.

In some embodiments, nucleic acid fragments can be joined at one or both ends to at least one nucleic acid adaptor. In some embodiments, methods for generating nucleic acid library constructs comprise the steps: (a) cleaving a nucleic acid by (i) nicking the nucleic acid at least once on each strand and (ii) nick translating the nicks thereby generating a double-stranded break to produce at least one nucleic acid fragment, wherein the nicking and/or the nick translating steps comprise a nucleic acid binding protein; and (b) joining at least one end of the at least one nucleic acid fragment to a oligonucleotide adaptor, thereby generating a fragment-adaptor molecule.

In some embodiments, methods for generating a nucleic acid library construct comprises the steps: (a) nicking a nucleic acid at least once on each strand; (b) nick translating the nicks thereby generating a double-stranded break to produce at least one nucleic acid fragment; (c) joining at least one end of the at least one nucleic acid fragment to an oligonucleotide adaptor, thereby generating a fragment-adaptor molecule.

In some embodiments, methods for generating a nucleic acid library construct comprises the steps: (a) providing a double-stranded nucleic acid having a first and a second nucleic acid strand; (b) nicking the first nucleic acid strand at least once to produce a first nick and nicking the second nucleic acid strand at least once to produce a second nick; (c) nick translating the first nick and the second nick thereby generating a double-stranded break to produce at least one nucleic acid fragment; and (d) joining at least one end of the nucleic acid fragment to an oligonucleotide adaptor, thereby generating a fragment-adaptor molecule. In some embodiments, fragment-adaptor molecules can be generated for preparing nucleic acid library constructs.

In some embodiments, any step of a method for generating a nucleic acid library construct can include a nucleic acid binding protein or can lack a nucleic acid binding protein.

In some embodiments, a nucleic acid fragment in a population comprises a first end and a second end. In some embodiments, a nucleic acid fragment can be joined at its first end to a first oligonucleotide adaptor. In some embodiments, a nucleic acid fragment can be joined at its second end to a second oligonucleotide adaptor. In some embodiments, on at least one end of a double-stranded nucleic acid fragment, one strand of the nucleic acid fragment can be joined to one strand of a double-stranded oligonucleotide adaptor to generate a fragment-adaptor molecule having a break (e.g., a nick or gap). In some embodiments, on at least one end of a double-stranded nucleic acid fragment, both strands of the nucleic acid fragment can be joined to both strand of a double-stranded oligonucleotide adaptor to generate a fragment-adaptor molecule. In some embodiments, the first and second oligonucleotide adaptors can be the same or different adaptors. In some embodiments, a nucleic acid fragment can be circularized by joining one or more oligonucleotide adaptors to both ends of a nucleic acid fragment. In some embodiments, nucleic acid fragments can be joined to at least one adaptor with a ligase enzyme, PCR amplification, nucleotide polymerization or any combination thereof. In some embodiments, one or both ends of a nucleic acid fragment can be joined to one or more adaptors, and the joining reaction can be conducted in solution. In some embodiments, one end or both ends of nucleic acid fragments can be joined to at least one type of oligonucleotide adaptor. In some embodiments, nucleic acid fragments and adaptors can be joined by ligation or annealing.

In some embodiments, an oligonucleotide adaptor can be DNA, RNA or chimeric RNA/DNA molecules. In some embodiments, an adaptor can include one or more ribonucleoside residues. In some embodiments, an adaptor can be single-stranded or double-stranded nucleic acids, or can include single-stranded or double-stranded portions. In some embodiments, an adaptor can have any structure, including linear, hairpin, forked, or stem-loop.

In some embodiments, an oligonucleotide adaptor can be a blocking oligonucleotide adaptor which comprises a double-stranded oligonucleotide adaptor (duplex) having an overhang cohesive portion that anneals with a blocking oligonucleotide which is a separate single-stranded oligonucleotide (PCT/US2011/054053, filed Sep. 29, 2011).

In some embodiments, an oligonucleotide adaptor can have any length, including fewer than 10 bases in length, or about 10-20 bases in length, or about 20-50 bases in length, or about 50-100 bases in length, or longer.

In some embodiments, an oligonucleotide adaptor can have any combination of blunt end(s) and/or sticky end(s). In some embodiments, at least one end of an adaptor can be compatible with at least one end of a nucleic acid fragment. In some embodiments, a compatible end of an adaptor can be joined to a compatible end of a nucleic acid fragment. In some embodiments, an adaptor can have a 5' or 3' overhang end.

In some embodiments, an oligonucleotide adaptor can include a monomeric sequence (e.g., AAA, TTT, CCC, or GGG) of any length, or an adaptor can include a complex sequence (e.g., non-monomeric sequence), or can include both monomeric and complex sequences.

In some embodiments, an oligonucleotide adaptor can have a 5' or 3' tail. In some embodiments, the tail can be one, two, three, or more nucleotides in length. In some embodiments, an adaptor can have a tail comprising A, T, C, G and/or U. In some embodiments, an adaptor can have a monomeric tail sequence of any length. In some embodiments, at least one end of an adaptor can have a tail that is compatible with a tail on one end of a nucleic acid fragment.

In some embodiments, an oligonucleotide adaptor can include an internal nick. In some embodiments, an adaptor can have at least one strand that lacks a terminal 5' phosphate residue. In some embodiments, an adaptor lacking a terminal 5' phosphate residue or lacking a terminal 3' OH can be joined to a nucleic acid fragment to introduce a nick at the junction between the adaptor and the nucleic acid fragment. In some embodiments, an adaptor can be ligated to a fragmented nucleic acid. In some embodiments, ligation of the adaptor to a fragmented nucleic acid results in the formation of a nick in the nucleic acid strand opposite the site of ligation. In some embodiments, the nick opposite the site of ligation can be repaired by denaturing the adaptor (thereby releasing the nucleotides of the adaptor adjacent to the nick to the termini of the adaptor), and extending the nucleic acid strand from the site of the nick to the termini of the adaptor using a nick repair enzyme. In some embodiments, the nick repair enzyme used to repair the nucleic acid strand can be Taq DNA polymerase, Bst DNA polymerase, Platinum® Pfx DNA polymerase (Invitrogen), Tfi Exo(−) DNA polymerase (Invitrogen) or Phusion® Hot Start High-Fidelity DNA polymerase (New England Biolabs).

In some embodiments, an oligonucleotide adaptor can include nucleotide sequences that are complementary to sequencing primers or amplification primers. In some embodiments, an adaptor can include a universal sequence that includes a nucleotide sequence that is part of, or is complementary to, a universal adaptor, a P1 adaptor, P2 adaptor, A (Ion-compatible adaptor), IA (internal adaptor), barcode sequence, amplification primer, or sequencing primer.

In some embodiments, an oligonucleotide adaptor can include degenerate sequences. In some embodiments, an adaptor can include one or more inosine residues.

In some embodiments, an oligonucleotide adaptor can include at least one scissile linkage. In some embodiments, a scissile linkage can be susceptible to cleavage or degradation by an enzyme or chemical compound. In some embodiments, an adaptor can include at least one phosphorothiolate, phosphorothioate, and/or phosphoramidate linkage.

In some embodiments, an oligonucleotide adaptor can include identification sequences. In some embodiments, an identification sequences can be used for sorting or tracking. In some embodiments, an identification sequences can be a unique sequence (e.g., barcode sequence). In some embodiments, a barcode sequence can allow identification of a particular adaptor among a mixture of different adaptors having different barcodes sequences. For example, a mixture can include 2, 3, 4, 5, 6, 7-10, 10-50, 50-100, 100-200, 200-500, 500-1000, or more different adaptors having unique barcode sequences.

In some embodiments, an oligonucleotide adaptor can include any type of restriction enzyme recognition sequence, including type I, type II, type IIs, type IIB, type III or type IV restriction enzyme recognition sequences.

In some embodiments, an oligonucleotide adaptor can include a cell regulation sequences, including a promoter (inducible or constitutive), enhancers, transcription or translation initiation sequence, transcription or translation termination sequence, secretion signals, Kozak sequence, cellular protein binding sequence, and the like.

Purification Steps:

In some embodiments, a population of nucleic acid fragments can be subjected to any purification procedure to remove non-desirable materials (buffers, salts, enzymes, primer-dimers, or excess adaptors or primers). In some embodiments, a purification procedure can be conducted between any two steps to remove buffers, salts, enzymes, adaptors, non-reacted nucleic acid fragments, and the like. Purification procedures include without limitation: bead purification, column purification, gel electrophoresis, dialysis, alcohol precipitation, and size-selective PEG precipitation.

Nucleic Acids

In some embodiments, a suitable nucleic acid sample to be fragmented can include single-stranded and double-stranded nucleic acids. In some embodiments, nucleic acids can include polymers of deoxyribonucleotides, ribonucleotides, and/or analogs thereof. In some embodiments, nucleic acids can include naturally-occurring and synthetic forms. In some embodiments, nucleic acids include single-stranded and double-stranded molecules. In some embodiments, nucleic acids can include DNA, cDNA RNA or chimeric RNA/DNA.

In some embodiments, a sample of nucleic acids to be fragmented can include single- or double-stranded DNA. In some embodiments, nucleic acids to be fragmented can be isolated in any form including chromosomal, genomic, organellar (e.g., mitochondrial, chloroplast or ribosomal), recombinant molecules, cloned, amplified (e.g., PCR amplified), cDNA, RNA such as precursor mRNA or mRNA, oligonucleotide, or any type of nucleic acid library such as an amplicon library. In some embodiments, nucleic acids to be fragmented can be isolated from any source including from organisms such as prokaryotes, eukaryotes (e.g., humans, plants and animals), fungus, and viruses; cells; tissues; normal or diseased cells or tissues or organs, body fluids including blood, urine, serum, lymph, tumor, saliva, anal and vaginal secretions, amniotic samples, perspiration, and semen; environmental samples; culture samples; or synthesized nucleic acid molecules prepared using recombinant molecular biology or chemical synthesis methods. In some embodiments, nucleic acids to be fragmented can be chemically synthesized to include any type of nucleic acid analog. In some embodiments, nucleic acids to be fragmented can be isolated from a formalin-fixed tissue, or from a paraffin-embedded tissue, or from a formalin-fix paraffin-embedded (FFPE) tissue.

In some embodiments, nucleic acids to be fragmented can be about 100 bp-1000 bp, or about 1 kb-50 kb, or about 50 kb-100 kb, or longer.

In some embodiments, nucleic acids to be fragmented can include a GC % content of about 0-10%, or about 10-25%, or about 25-40%, or about 40-55%, or about 55-70%, or about 70-85%, or about 85-100%.

In some embodiments, nucleic acid fragmentation reaction can be conducted with about 0.01-0.1 ng, or about 0.1-1 ng, or about 1-5 ng, or about 5-10 ng, or about 10-50 ng, or about 50-100 ng, or about 100-500 ng, or about 500-1000 ng, or about 1-2 ug, or about 2-5 ug, or about 5-10 ug, or about 10-50 ug, or about 50-100 ug, or about 100-500 ug, or about 500-1000 ug, or more.

Polymerases

In some embodiments, methods for generating a population of nucleic acid fragments can include one or more different polymerases. In some embodiments, a polymerase includes any enzyme, or fragment or subunit of thereof, that can catalyze polymerization of nucleotides and/or nucleotide analogs. In some embodiments, a polymerase requires the terminal 3' OH of a nucleic acid primer to initiate nucleotide polymerization. In some embodiments, a linker nucleic acid provides a terminal 3'OH for the polymerase to polymerize the nucleotides.

A polymerase comprises any enzyme that can catalyze the polymerization of nucleotides (including analogs thereof) into a nucleic acid strand. Typically but not necessarily such nucleotide polymerization can occur in a template-dependent fashion. In some embodiments, a polymerase can be a high fidelity polymerase. Such polymerases can include without limitation naturally occurring polymerases and any subunits and truncations thereof, mutant polymerases, variant polymerases, recombinant, fusion or otherwise engineered polymerases, chemically modified polymerases, synthetic molecules or assemblies, and any analogs, derivatives or fragments thereof that retain the ability to catalyze such polymerization. Optionally, the polymerase can be a mutant polymerase comprising one or more mutations involving the replacement of one or more amino acids with other amino acids, the insertion or deletion of one or more amino acids from the polymerase, or the linkage of parts of two or more polymerases. The term "polymerase" and its variants, as used herein, also refers to fusion proteins comprising at least two portions linked to each other, where the first portion comprises a peptide that can catalyze the polymerization of nucleotides into a nucleic acid strand and is linked to a second portion that comprises a second polypeptide, such as, for example, a reporter enzyme or a processivity-enhancing domain. Typically, the polymerase comprises one or more active sites at which nucleotide binding and/or catalysis of nucleotide polymerization can occur. In some embodiments, a polymerase includes other enzymatic activities, such as for example, 3' to 5' exonuclease activity or 5' to 3' exonuclease activity. In some embodiments, a polymerase can be isolated from a cell, or generated using recombinant DNA technology or chemical synthesis methods. In some embodiments, a polymerase can be expressed in prokaryote, eukaryote, viral, or phage organisms. In some embodiments, a polymerase can be post-translationally modified proteins or fragments thereof.

In some embodiments, a polymerase can be a DNA polymerase and include without limitation bacterial DNA polymerases, eukaryotic DNA polymerases, archaeal DNA polymerases, viral DNA polymerases and phage DNA polymerases.

In some embodiments, a polymerase can be a replicase, DNA-dependent polymerase, primases, RNA-dependent polymerase (including RNA-dependent DNA polymerases such as, for example, reverse transcriptases), a strand-displacement polymerase, a thermo-labile polymerase, or a thermo-stable polymerase. In some embodiments, a polymerase can be any Family A or B type polymerase. Many types of Family A (e.g., *E. coli* Pol I), B (e.g., *E. coli* Pol II), C (e.g., *E. coli* Pol III), D (e.g., Euryarchaeotic Pol II), X (e.g., human Pol beta), and Y (e.g., *E. coli* UmuC/DinB and eukaryotic RAD30/xeroderma pigmentosum variants) polymerases are described in Rothwell and Watsman 2005 Advances in Protein Chemistry 71:401-440. In some embodiments, a polymerase can be a T3, T5, T7, or SP6 RNA polymerase.

Some exemplary polymerases include without limitation DNA polymerases (such as for example Phi-29 DNA polymerase, reverse transcriptases and *E. coli* DNA polymerase) and RNA polymerases.

In some embodiments, an archaeal DNA polymerase can be, without limitation, a thermostable or thermophilic DNA polymerase such as, for example: a *Thermus aquaticus* (Taq) DNA polymerase; *Thermus filiformis* (Tfi) DNA polymerase; *Thermococcus zilligi* (Tzi) DNA polymerase; *Thermus thermophilus* (Tth) DNA polymerase; *Thermus flavus* (Tfl) DNA polymerase; *Pyrococcus* woesei (Pwo) DNA polymerase; *Pyrococcus furiosus* (Pfu) DNA polymerase as well as Turbo Pfu DNA polymerase; *Thermococcus litoralis* (Tli) DNA polymerase or Vent DNA polymerase; *Pyrococcus* sp. GB-D polymerase; "Deep Vent" DNA polymerase (New England Biolabs); *Thermotoga maritima*(Tma) DNA polymerase; *Bacillus stearothermophilus* (Bst) DNA polymerase; *Pyrococcus* Kodakaraensis (KOD) DNA polymerase; Pfx DNA polymerase; *Thermococcus* sp. JDF-3 (JDF-3) DNA polymerase; *Thermococcus gorgonarius* (Tgo) DNA polymerase; *Thermococcus acidophilium* DNA polymerase; *Sulfolobus acidocaldarius* DNA polymerase; *Thermococcus* sp. 9° N-7 DNA polymerase; *Thermococcus* sp. NA1; *Pyrodictium occultum* DNA polymerase; *Methanococcus voltae* DNA polymerase; *Methanococcus thermoautotrophicum* DNA polymerase; *Methanococcus jannaschii* DNA polymerase; Desulfurococcus strain TOK DNA polymerase (D. Tok Pol); *Pyrococcus abyssi* DNA polymerase; *Pyrococcus horikoshii* DNA polymerase; *Pyrococcus islandicum* DNA polymerase; *Thermococcus fumicolans* DNA polymerase; *Aeropyrum pernix* DNA polymerase; or heterodimeric DNA polymerase DP1/DP2. In some embodiments, a polymerase can be a commercially-available polymerase, such as AmpliTaq™ or AmpliTaq Gold™ (both from Applied Biosystems).

These and other polymerases are described by Rothwell and Watsman (2005 Advances in Protein Chemistry 71:401-440). One skilled in the art will know which polymerase(s) to select to conduct a cleaving, nick translating, and/or tailing reaction.

Nicking Reaction

In some embodiments, methods for generating a population of nucleic acid fragments can include nicking a nucleic acid with an enzyme. In some embodiments, nucleic acid nicking enzymes include any enzyme having endonuclease activity, with or without exonuclease activity. In some embodiments, nucleic acid nicking enzymes include any enzyme that can catalyze nicking one or both strands of a double-stranded nucleic acid. In some embodiments, nucleic acid nicking enzymes include any enzyme that can catalyze introducing a nick at random positions in one or both strands of a double-stranded nucleic acid. In some embodiments, nucleic acid nicking enzymes include any enzyme that can introduce one or more nicks at random (or nearly random) positions in either strand of a double-stranded nucleic acid. In some embodiments, nucleic acid nicking enzymes include any enzyme that can introduce one or more nicks in a non-specific sequence manner at any position in either strand of a double-stranded nucleic acid. In some embodiments, nucleic acid nicking enzymes include any wild-type or mutant deoxyribonucleases I (DNase I) enzyme isolated from any organism or tissue, or isolated as a recombinant enzyme. In some embodiments, a DNase I can be isolated from bovine. In some embodiments, a DNase I can be isolated from pancreas.

In some embodiments, a nucleic acid nicking enzyme can be a DNase from a family Virionaceae, such as genus *Vibrio*, which includes *Vibrio vulnificus*. In some embodiments, a nucleic acid nicking enzyme can be a Vvn nuclease. In some embodiments, a nucleic acid nicking enzyme can be a nuclease from *Vibrio cholera* (Focareta and Manning 1987 Gene 53(1):31-400, or an NucM polymerase from *Erwinia chrysanthemi* (Moulard 1993 Mol. Microbiol. 8)4):685-695, or an Endo I nuclease from *E. coli* (Jekel 1995 Gene 154(1):55-59, or a Dns or DnsH nuclease from *Aeromonas hydrophila* (Chang 1992 Gene 122(1):175-180, Dodd 1999 FEMS Microbiol. Lett. 173:41-46, and Wang 2007 Nucleic Acids Research 35:584-594). In some embodiments, a nucleic acid nicking enzyme can be a DNase from a family Enterobacteriaceae, such as a genus *Serratia*, which includes *Serratia marcescens* (Benzonase™, U.S. Pat. No. 5,173, 418).

In some embodiments, a nucleic acid nicking enzyme exhibits little or no preference for nicking nucleic acids at sequences having a high or low GC % content, including nucleic acids having about 0-10%, or about 10-25%, or about 25-40%, or about 40-55%, or about 55-70%, or about 70-85%, or about 85-100% GC % content.

Nick Translating

In some embodiments, methods for generating a population of nucleic acid fragments can include a nick translation reaction. A nick translation can include any process or treatment whereby the position of a nick within a nucleic acid strand is effectively moved to a new position in a nucleic acid strand. Nick translation typically includes extension of one new strand accompanied by digestion or erosion of the other new strand. In some embodiments, nick translation includes polymerization of nucleotides or nucleotide analogs onto the new 3' end as well as digestion or erosion of nucleosides from the new 5' end. With each successive nucleotide polymerization onto the new 3' end, the position of the nick is effectively moved by one nucleotide position along the nicked strand. Nick translation can optionally continue until the nick is translated to the end of the nicked strand, or until the translated nick comes into either complete alignment or into sufficiently close proximity to another nick in the opposing strand as to form a double stranded break, resulting in the generation of two nucleic acid fragments derived from the original double stranded nucleic acid. The double stranded break may generate two new blunt ends or two new "sticky" ends in the resulting nucleic acid fragments.

In some embodiments, nick translating can include two or more enzymatic activities that act on double stranded nucleic acids to: (1) nick a double stranded nucleic acid and (2) translate the nick. For example, a nicking enzyme can introduce a nick on at least one nucleic acid strand, and a polymerase can act at the nick to remove nucleotides in a 5'→3' direction (exonuclease activity) while incorporating nucleotides in a 5'→3' direction (polymerization activity). Alternatively, a nicking enzyme can introduce a nick on at least one nucleic acid strand, and a polymerase can move in a 5'→3' direction to displace one strand (strand displacing activity) while incorporating nucleotides in a 5'→3' direction (polymerization activity).

In some embodiments, the position of a nick can be moved to a new position by reacting a nick on a double stranded nucleic acid with an polymerase that moves in a 5'→3' direction to degrade nucleotides or nucleosides (exonuclease activity) while polymerizing nucleotides onto the free 3' end of the nick in a 5'→3' direction (polymerization activity).

In some embodiments, a nick on a double stranded nucleic acid can be reacted with a polymerase that moves in a 5'→3' direction to displace one strand (strand displacing activity) while polymerizing nucleotides onto the free 3' end of the nick in a 5'→3' direction (polymerization activity).

In some embodiments, a nick translation reaction can be catalyzed by one or more enzymes that couples a 5'→3' nucleic acid polymerization and degradation reaction. In some embodiments, a nick translation reaction can be catalyzed by any nucleic acid polymerase having a 5'→3' nucleotide polymerization activity and a 5'→3' exonuclease activity. In some embodiments, a nick translation reaction can be catalyzed by any nucleic acid polymerase lacking a 3'→5' exonuclease activity. In some embodiments, a nick translation reaction can be catalyzed by any DNA polymerase. In some embodiments, a nick translation reaction can be catalyzed by any Family A DNA polymerase (also known as pol I family). In some embodiments, a nick translation reaction can be catalyzed by Klenow fragment.

In some embodiments, a nick translation reaction can be catalyzed by *E. coli* DNA Pol I. In some embodiments, a nick translation reaction can be catalyzed by one or more thermostable enzymes having 5'→3' nucleotide polymerization activity and a 5'→3' exonuclease activity. In some embodiments, a thermostable enzyme includes Taq polymerase (from *Thermus aquaticus*), Tfi polymerase (from *Thermus filiformis*), Pfu polymerase (from *Pyrococcus furiosus*), Tth (from *Thermus thermophilus*), Pow polymerase (from *Pyrococcus woesei*), Tli polymerase (from *Thermococcus litoralis*), Pol I and II polymerases (from *Pyrococcus abyssi*), and Pab (from *Pyrococcus abyssi*).

In some embodiments, a nick translation reaction can be catalyzed by one or more enzymes that couples a 5' to 3' DNA polymerization and strand displacement reaction. In some embodiments, a strand displacing polymerase includes Taq polymerase, Tfi polymerase, Bst polymerase (from *Bacillus stearothermophilus*), Tli polymerase, 9° N polymerase, and phi29 polymerase.

In some embodiments, a nick translation reaction can be catalyzed by a combination of a helicase and a DNA polymerase.

In some embodiments, a nick translation reaction includes a nick translation enzyme and at least one type of nucleotide. In some embodiments, the nick translation enzyme catalyzes polymerization of one or more nucleotides onto the new 3' end at the nick site. In some embodiments, the nucleotides that are polymerized onto the new 3' end can be unlabeled to or labeled with a detectable moiety, or a combination of unlabeled and labeled nucleotides. In some embodiments, a nick translation reaction can generate unlabeled or labeled ends.

Tailing

In some embodiments, methods for generating a population of nucleic acid fragments can include a non-template-dependent terminal transferase reaction (e.g., tailing reaction). In some embodiments, a non-template-dependent terminal transferase reaction can be catalyzed by a Taq polymerase, Tfi DNA polymerase, 3' exonuclease minus-large (Klenow) fragment, or 3' exonuclease minus-T4 polymerase.

Nick Repair

In some embodiments, methods for generating a population of nucleic acid fragments can include a nick repair enzyme (e.g., nick repairing or nick repair reaction). In some embodiments, a nick repair reaction can be catalyzed by a nick repair polymerase such as Taq DNA polymerase, Bst DNA polymerase, Platinum® Pfx DNA polymerase (Invitrogen), Tfi Exo(−) DNA polymerase (Invitrogen) or Phusion® Hot Start High-Fidelity DNA polymerase (New England Biolabs). In some embodiments, the nick repair enzyme can be used to extend the nucleic acid strand from the site of the nick to the original termini of the adaptor sequence.

Nucleotides

In some embodiments, methods for generating a population of nucleic acid fragments can be conducted with one or more types of nucleotides. A nucleotide comprises any compound that can bind selectively to, or can be polymerized by, a polymerase. Typically, but not necessarily, selective binding of the nucleotide to the polymerase is followed by polymerization of the nucleotide into a nucleic acid strand by the polymerase; occasionally however the nucleotide may dissociate from the polymerase without becoming incorporated into the nucleic acid strand, an event referred to herein as a "non-productive" event. Such nucleotides include not only naturally occurring nucleotides but also any analogs, regardless of their structure, that can bind selectively to, or can be polymerized by, a polymerase. While naturally occurring nucleotides typically comprise base, sugar and phosphate moieties, the nucleotides of the present disclosure can include compounds lacking any one, some or all of such moieties. In some embodiments, the nucleotide can optionally include a chain of phosphorus atoms comprising three, four, five, six, seven, eight, nine, ten or more phosphorus atoms. In some embodiments, the phosphorus chain can be attached to any carbon of a sugar ring, such as the 5' carbon. The phosphorus chain can be linked to the sugar with an intervening O or S. In one embodiment, one or more phosphorus atoms in the chain can be part of a phosphate group having P and O. In another embodiment, the phosphorus atoms in the chain can be linked together with intervening O, NH, S, methylene, substituted methylene, ethylene, substituted ethylene, $CNH_2$, $C(O)$, $C(CH_2)$, $CH_2CH_2$, or $C(OH)CH_2R$ (where R can be a 4-pyridine or 1-imidazole). In one embodiment, the phosphorus atoms in the chain can have side groups having O, $BH_3$, or S. In the phosphorus chain, a phosphorus atom with a side group other than O can be a substituted phosphate group. In the phosphorus chain, phosphorus atoms with an intervening atom other than O can be a substituted phosphate group. Some examples of nucleotide analogs are described in Xu, U.S. Pat. No. 7,405,281.

Some examples of nucleotides that can be used in the disclosed methods and compositions include, but are not limited to, ribonucleotides, deoxyribonucleotides, modified ribonucleotides, modified deoxyribonucleotides, ribonucleotide polyphosphates, deoxyribonucleotide polyphosphates, modified ribonucleotide polyphosphates, modified deoxyribonucleotide polyphosphates, peptide nucleotides, modified peptide nucleotides, metallonucleosides, phosphonate nucleosides, and modified phosphate-sugar backbone nucleotides, analogs, derivatives, or variants of the foregoing compounds, and the like. In some embodiments, the nucleotide can comprise non-oxygen moieties such as, for example, thio- or borano-moieties, in place of the oxygen moiety bridging the alpha phosphate and the sugar of the nucleotide, or the alpha and beta phosphates of the nucleotide, or the beta and gamma phosphates of the nucleotide, or between any other two phosphates of the nucleotide, or any combination thereof.

In some embodiments, the nucleotide comprises a label and referred to herein as a "labeled nucleotide"; the label of the labeled nucleotide is referred to herein as a "nucleotide label". In some embodiments, the label can be in the form of a fluorescent dye attached to any portion of a nucleotide including a base, sugar or any intervening phosphate group or a terminal phosphate group, i.e., the phosphate group most distal from the sugar.

Labels

In some embodiments, a nucleotide (or analog thereof) can be attached to a label. In some embodiments, a label comprises a detectable moiety. In some embodiments, a label can generate, or cause to generate, a detectable signal. A detectable signal can be generated from a chemical or physical change (e.g., heat, light, electrical, pH, salt concentration, enzymatic activity, or proximity events). For example, a proximity event can include two reporter moieties approaching each other, or associating with each other, or binding each other. A detectable signal can be detected optically, electrically, chemically, enzymatically, thermally, or via mass spectroscopy or Raman spectroscopy. A label can include compounds that are luminescent, photoluminescent, electroluminescent, bioluminescent, chemiluminescent, fluorescent, phosphorescent or electrochemical. A label can include compounds that are fluorophores, chromophores, radioisotopes, haptens, affinity tags, atoms or enzymes. In some embodiments, the label comprises a moiety not typically present in naturally occurring nucleotides. For example, the label can include fluorescent, luminescent or radioactive moieties.

Nucleic Acid Binding Proteins

In some embodiments, the methods for generating a population of nucleic acid fragments can include binding a nucleic acid with a protein that binds nucleic acids (e.g., nucleic acid binding protein), or can lack this step. In some embodiments, the methods can include binding a nucleic acid with a nucleic acid binding protein at any step, which can be conducted once or can be repeated.

In some embodiments, the methods can include binding a nucleic acid with a nucleic acid binding protein before, during and/or after a nicking reaction. In some embodiments, the methods can include binding a nucleic acid with a nucleic acid binding protein before, during and/or after a nick translation reaction. For example, a nucleic acid can be subjected to a nicking reaction and/or a nick translation reaction in the presence of a nucleic acid binding protein. In some embodiments, a nucleic acid binding protein can be added after conducting nicking reaction and/or a nick translation reaction.

In some embodiments, a nucleic acid binding protein can be a protein or at least a portion thereof. In some embodiments, a nucleic acid binding protein can be a multimeric protein complex (e.g., dimers, trimers, tetramers or higher order multimers), that binds a nucleic acid. In some embodiments, a multimeric protein complex can be hetero-polymeric or homo-polymeric. In some embodiments, a nucleic acid binding protein can bind DNA, RNA, or any analog or derivative thereof. In some embodiments, a nucleic acid binding protein can bind single-stranded nucleic acids with higher affinity compared to binding double-stranded or triple-stranded nucleic acids. In some embodiments, a nucleic acid binding protein can be a single-stranded nucleic acid binding protein (Chase and Williams 1986 Ann. Rev. Biochem. 55:103-136). In some embodiments, a nucleic acid binding protein can bind a double strand and a single strand (e.g., recA can bind three nucleic acid strands). In some embodiments, a nucleic acid binding protein can bind a folded or non-folded nucleic acid. In some embodiments, a nucleic acid binding protein can exhibit little or no sequence specificity for binding nucleic acids. In some embodiments, one or more nucleic acid binding proteins can bind a nucleic acid strand. In some embodiments, multiple nucleic acid binding proteins can cooperatively bind a nucleic acid strand (Lohman and Ferrari 1994 Ann. Rev. Biochem. 63:527-570) or can bind non-cooperatively. In some embodiments, a nucleic acid binding protein can be wild-type, mutant or truncated. In some embodiments, at nucleic acid binding protein can be a naturally-occurring or can be a recombinant protein prepared using recombinant DNA methods (Haseltine 2002 Mol. Microbiol. 43:1505-1515).

In some embodiments, a nucleic acid binding protein can be a mesophilic or thermostable protein. A thermostable nucleic acid binding protein can be resistant to inactivation by heat, such as a temperature range of about 50-95° C. for about 15 seconds to 10 minutes or longer. For example, a thermostable nucleic acid binding protein can retain about 50-95% activity at a temperature range of about 50-95° C.

In some embodiments, a nucleic acid binding protein can be from any type of organism, including prokaryotic, eukaryotic, virus or phage. A nucleic acid binding protein can originate from any type of cell, tissue or cell culture. A nucleic acid binding protein from a eukaryotic organism can originate from any organelle, including nuclear, mitochondria, or chloroplast, or can originate from cytoplasm. A nucleic acid binding protein from a eukaryotic organism can originate from any organ, including thymus. A nucleic acid binding protein from a prokaryotic organism can be episomally-encoded.

In some embodiments, a nucleic acid binding protein can mediate in vivo and/or in vitro reactions, including: DNA replication, repair and/or recombination (Kowalczykowski 1994 Microbiol Rev. 58:401-465; Lohman and Ferrari 1994 Ann. Rev. Biochem. 63:527-570; Wold 1997 Annu. Rev. Biochem. 66:61-92; Chedin 1998 Trends Biochem. Sci. 23:273-277; Kelly 1998 Proc. Natl. Acad. Sci. USA 95:14634-14639; Iftody 1999 Crit. Rev. Biochem. Mol. Biol 34:141-180); helix destabilization; reduction of DNA secondary structures; renaturation of complementary sequences; protection of nucleic acids from nucleases; and/ or repair via homologous recombination (e.g., RecA, Zhumabayeva 1990 Biotechniques 27:834-845; LexA, Radman, 1974 "Phenomenology of an inducible mutagenic DNA repair pathway in *Escherichia coli*: SOS repair hypothesis" in Sherman(ed) in: Molecular and Environmental Aspects of Mutagenesis, Springfield, Ill., Charles C. Thomas publisher, pp. 128-142; and Bridges 2005, in: DNA Repair, (Amst) vol 4(6), pp. 725-739).

In some embodiments, a nucleic acid binding protein can include one or more OB folds or OB fold-like structures (oligonucleotide/oligosaccharide binding fold) having a five-stranded antiparallel beta-barrel terminating in an alpha-helix (Murzin 1993 EMBO J. 12:861-867; Philipova 1996 Genes Dev. 10:2222-2233).

In some embodiments, a nucleic acid binding protein can be a phage T4 gp 32 protein (Williams 1981 J. Biol. Chem. 256:1754-1762; Topal and Sinha 1983 J. Biol. Chem. 258: 12274-12279; GenBank accession BAG54790; FIG. 4), or a T7 gp 2.5 protein or phi29 protein p5 protein.

In some embodiments, a nucleic acid binding protein can be from *Sulfolobus solfataricus* (Sso SSB) (Haseltine and Kowalczykowski 2002 Mol. Microbiol. 43:1505-1515; FIG. 5).

In some embodiments, a nucleic acid binding protein can be from *E. coli* (Skyberg 2006 Infect. Immun. 74:6287-6292; Sigal 1972 Proc. Natl. Acad. Sci. USA 69:3537-3541; Weiner 1975 J. Biol. Chem. 250:1972-1980; GenBank accession ABC42252; FIG. 6).

In some embodiments, a nucleic acid binding protein can be from *Methanococcus jannaschii* (Mja SSB) (Kelly 1998 PNAS 95:14634-14639; GenBank accession NP_248153; FIG. 7).

In some embodiments, a nucleic acid binding protein can be a: phage T7 SSB; T4 gene 44/62 protein; coliphage N4 SSB; adenovirus DNA binding protein (Ad DBP or Ad SSB); calf thymus unwinding protein (UP1); episomal encoded SSB (Kolodkin 1983 Proc. Natl. Acad. Sci. USA 80:4422-4426); mitochondrial (rim-1); yeast (e.g., rpa-1, SSB I, SSB II, or SSB III); HeLa $A_1$ protein; *Bacillus subtilis* SSB; *Saccharomyces cerevisiae* RPA70 single-stranded DNA-binding region 1; eukaryotic replication protein A (RPA) (Smith 1997 J. Bacteriol. 179:7135-7155; Wold 1997 Annu. Rev. Biochem. 66:61-92); or from *Homo sapiens*.

In some embodiments, a nucleic acid binding protein can be a RecA or RecA-like protein including RecA (bacteria), Rad51 (eukaryotes), and RadA (archaeal) (Kowalczykowski 1994 Annu. Rev. Biochem. 63:991-1043; Kuzminov 1999 Microbiol. Mol. Biol. Rev. 63:751-813; Bianco 2005 in "RecA protein" John Wiley and Sons, Ltd. Chichester, UK).

In some embodiments, nucleic acid binding proteins can originate from thermophilic organisms, including *Methanococcus* (e.g., *Methanococcus jannachii*), *Methanobacterium* (e.g., *Methanobacterium thermoautrophicum*), *Archaeoglobus* (e.g., *Archaeoglobus fulgidus*), *Sulfolobus* (e.g., *Sulfolobus sulfataricus*), *Aeropyrum* (e.g., *Aeropyrum pernix*) (see e.g., Chedin, 1998 Trends Biochem. Sci. 23:273-277; Haseltine 2002 Mol. Microbiol. 43:1505-1515; Kelly 1998 Proc. Natl. Acad. Sci. USA 95:14634-14639; Klenk 1997 Nature 390:364-370; Smith 1997 J. Bacteriol. 179:7135-55; Wadsworth and White 2001 Nucl. Acids Res. 29:914-920).

For example, a thermostable nucleic acid binding protein can be a: *Thermus thermophilus* SSB (e.g., GenBank AJ564626); *Thermus aquaticus* SSB (e.g., GenBank AF276705); *Methanococcus thermoautrophicum* SSB; *Methanococcus jannaschii* RPA protein; *Aeropyrum pernix* (ApeSSB); *Archaeoglobus fulgidus* SSB; *Pyrococcus abyssii* SSB; or *Pyrococcus horikoshii* SSB.

In some embodiments, a single stranded binding protein can be any SSB found in Table 1 at pages 9-16 of published patent application No. U.S. 2007/0178491 (Park and Lee).

Suitable Conditions

In some embodiments, methods for generating a population of nucleic acid fragments can be conducted under conditions that are suitable for introducing one or more nicks on either strand of a double-stranded nucleic acid and/or suitable for moving the positions of the nicks to a new position along the double-stranded nucleic acid and/or suitable for binding nucleic acids to one or more nucleic acid binding proteins and/or suitable conditions for joining ends of nucleic acid fragments to oligonucleotide adaptors.

In some embodiments, methods for generating a population of nucleic acid fragments can be conducted under conditions that are suitable for nicking the first nucleic acid strand and/or suitable for nicking the second nucleic acid strand and/or suitable for moving the position of first nick and/or suitable for moving the position of the second nick and/or suitable for joining at least one end of a nucleic acid fragment to an oligonucleotide adaptor.

In some embodiments, suitable conditions include well known parameters, such as: time, temperature, pH, buffers, reagents, cations, salts, co-factors, nucleotides, nucleic acids, and enzymes. In some embodiments, a reagent or buffer can include a source of ions, such as KCl, K-acetate, $NH_4$-acetate, K-glutamate, $NH_4Cl$, or ammonium sulfate. In some embodiments, a reagent or buffer can include a source of divalent ions, such as $Mg^{2+}$ or $Mn^{2\pm}$, $MgCl_2$, $MnCl_2$, or Mg-acetate. In some embodiments, a reagent or buffer can include magnesium, manganese and/or calcium. In some embodiments, a buffer can include Tris, Tricine, HEPES, MOPS, ACES, MES, or inorganic buffers such as phosphate or acetate-based buffers which can provide a pH range of about 4-12. In some embodiments, a buffer can include chelating agents such as EDTA or EGTA. In some embodiments, a buffer can include dithiothreitol (DTT), glycerol, spermidine, and/or BSA (bovine serum albumin). In some embodiments, a buffer can include ATP.

In some embodiments, suitable conditions include conducting a nick translation reaction with an enzyme and one or more types of nucleotides. In some embodiments, suitable conditions include conducting a non-template-dependent terminal transferase reaction with an enzyme and one or more types of nucleotides. In some embodiments, a suitable condition includes joining at least one end of a nucleic acid fragment to an oligonucleotide adaptor with a ligase enzyme (e.g., T4 DNA ligase, Taq DNA ligase or a derivative thereof).

In some embodiments, suitable conditions include cyclical temperature changes, or isothermal temperature conditions, or a combination of both. In some embodiments, a reaction can be conducted at a temperature range of about 0-10° C., or about 10-20° C., or about 20-30° C., or about 30-40° C., or about 40-50° C., or about 50-60° C., or about 60-70° C., or about 70-80° C., or about 80-90° C., or about 90-100° C., or high temperatures.

In some embodiments, suitable conditions include conducting a reaction for a time, such as about 10-30 seconds, or about 30-60 seconds, or about 1-3 minutes, or about 3-5 minutes, or about 5-6 minutes, or about 6-7 minutes, or about 7-8 minutes, or about 8-9 minutes, or about 9-10 minutes, or about 10-11 minutes, or about 11-12 minutes, or about 12-13 minutes, or about 13-14 minutes, or about 14-15 minutes, or about 15-20 minutes, or about 20-30 minutes, or about 30-45 minutes, or about 45-60 minutes, or about 1-3 hours, or about 3-6 hours, or about 6-10 hours, or longer.

In some embodiments, suitable conditions include conducting a reaction in a volume of about 1-10 uL, or about 10-25 uL, or about 25-50 uL, or about 50-75 uL, or about 75-100 uL, or about 100-125 uL, or about 125-150 uL, or about 150-200 uL, or more.

In some embodiments, suitable conditions include conducting a reaction in a tube or well. In some embodiments, the well can be a part of a 96-well plate.

In some embodiments, the number of nicks introduced on either strand of a double-stranded nucleic acid and/or a nick translation reaction can be adjusted by varying any parameters, including varying: the time; temperature; pH; amount of template; enzyme concentration; nucleotide concentration; type of salts, cations and/or ions; amount of salts, cations, and/or ions; reaction volume; or any combination thereof.

Sequencing Methods

In some embodiments, one or more nucleic acid fragments produced according to the present teachings can be sequenced using methods that detect one or more byproducts of nucleotide incorporation. The detection of polymerase extension by detecting physicochemical byproducts of the extension reaction, can include pyrophosphate, hydrogen ion, charge transfer, heat, and the like, as disclosed, for example, in Pourmand et al, Proc. Natl. Acad. Sci., 103: 6466-6470 (2006); Purushothaman et al., IEEE ISCAS, IV-169-172; Rothberg et al, U.S. Patent Publication No. 2009/0026082; Anderson et al, Sensors and Actuators B Chem., 129: 79-86 (2008); Sakata et al., Angew. Chem. 118:2283-2286 (2006); Esfandyapour et al., U.S. Patent Publication No. 2008/01666727; and Sakurai et al., Anal. Chem. 64: 1996-1997 (1992).

Reactions involving the generation and detection of ions are widely performed. The use of direct ion detection methods to monitor the progress of such reactions can simplify many current biological assays. For example, template-dependent nucleic acid synthesis by a polymerase can be monitored by detecting hydrogen ions that are generated as natural byproducts of nucleotide incorporations catalyzed by the polymerase. Ion-sensitive sequencing (also referred to as "pH-based" or "ion-based" nucleic acid sequencing) exploits the direct detection of ionic byproducts, such as hydrogen ions, that are produced as a byproduct of nucleotide incorporation. In one exemplary system for ion-based sequencing, the nucleic acid to be sequenced can be captured in a microwell, and nucleotides can be floated across the well, one at a time, under nucleotide incorporation conditions. The polymerase incorporates the appropriate nucleotide into the growing strand, and the hydrogen ion that is released can change the pH in the solution, which can be detected by an ion sensor. This technique does not require labeling of the nucleotides or expensive optical components, and allows for far more rapid completion of sequencing runs. Examples of such ion-based nucleic acid sequencing methods and platforms include the Ion Torrent PGM™ or Proton™ sequencer (Ion Torrent™ Systems, Life Technologies Corporation).

In some embodiments, one or more nucleic acid fragments produced using the methods, systems and kits of the present teachings can be used as a substrate for a biological or chemical reaction that is detected and/or monitored by a sensor including a field-effect transistor (FET). In various embodiments the FET is a chemFET or an ISFET. A "chemFET" or chemical field-effect transistor, is a type of field effect transistor that acts as a chemical sensor. It is the structural analog of a MOSFET transistor, where the charge on the gate electrode is applied by a chemical process. An "ISFET" or ion-sensitive field-effect transistor, is used for measuring ion concentrations in solution; when the ion concentration (such as H+) changes, the current through the transistor will change accordingly. A detailed theory of operation of an ISFET is given in "Thirty years of ISFETOLOGY: what happened in the past 30 years and what may happen in the next 30 years," P. Bergveld, Sens. Actuators, 88 (2003), pp. 1-20.

In some embodiments, the FET may be a FET array. As used herein, an "array" is a planar arrangement of elements such as sensors or wells. The array may be one or two dimensional. A one dimensional array can be an array having one column (or row) of elements in the first dimension and a plurality of columns (or rows) in the second dimension. The number of columns (or rows) in the first and second dimensions may or may not be the same. The FET or array can comprise 102, 103, 104, 105, 106, 107 or more FETs.

In some embodiments, one or more microfluidic structures can be fabricated above the FET sensor array to provide for containment and/or confinement of a biological or chemical reaction. For example, in one implementation, the microfluidic structure(s) can be configured as one or more wells (or microwells, or reaction chambers, or reaction wells, as the terms are used interchangeably herein) disposed above one or more sensors of the array, such that the one or more sensors over which a given well is disposed detect and measure analyte presence, level, and/or concentration in the given well. In some embodiments, there can be a 1:1 correspondence of FET sensors and reaction wells.

Microwells or reaction chambers are typically hollows or wells having well-defined shapes and volumes which can be manufactured into a substrate and can be fabricated using conventional microfabrication techniques, e.g. as disclosed in the following references: Doering and Nishi, Editors, Handbook of Semiconductor Manufacturing Technology, Second Edition (CRC Press, 2007); Saliterman, Fundamentals of BioMEMS and Medical Microdevices (SPIE Publications, 2006); Elwenspoek et al, Silicon Micromachining (Cambridge University Press, 2004); and the like. Examples of configurations (e.g. spacing, shape and volumes) of microwells or reaction chambers are disclosed in Rothberg et al, U.S. patent publication 2009/0127589; Rothberg et al, U.K. patent application GB24611127.

In some embodiments, the biological or chemical reaction can be performed in a solution or a reaction chamber that is in contact with or capacitively coupled to a FET such as a chemFET or an ISFET. The FET (or chemFET or ISFET) and/or reaction chamber can be an array of FETs or reaction chambers, respectively.

In some embodiments, a biological or chemical reaction can be carried out in a two-dimensional array of reaction chambers, wherein each reaction chamber can be coupled to a FET, and each reaction chamber is no greater than 10 μm³ (i.e., 1 pL) in volume. In some embodiments each reaction chamber is no greater than 0.34 pL, 0.096 pL or even 0.012 pL in volume. A reaction chamber can optionally be 22, 32, 42, 52, 62, 72, 82, 92, or 102 square microns in cross-sectional area at the top. Preferably, the array has at least 102, 103, 104, 105, 106, 107, 108, 109, or more reaction chambers. In some embodiments, the reaction chambers can be capacitively coupled to the FETs.

FET arrays as used in various embodiments according to the disclosure can be fabricated according to conventional CMOS fabrications techniques, as well as modified CMOS fabrication techniques and other semiconductor fabrication techniques beyond those conventionally employed in CMOS fabrication. Additionally, various lithography techniques can be employed as part of an array fabrication process.

Exemplary FET arrays suitable for use in the disclosed methods, as well as microwells and attendant fluidics, and methods for manufacturing them, are disclosed, for example, in U.S. Patent Publication No. 20100301398; U.S. Patent Publication No. 20100300895; U.S. Patent Publication No. 20100300559; U.S. Patent Publication No. 20100197507, U.S. Patent Publication No. 20100137143; U.S. Patent Publication No. 20090127589; and U.S. Patent Publication No. 20090026082, which are incorporated by reference in their entireties.

In one aspect, the disclosed methods, compositions, systems, apparatuses and kits can be used for carrying out label-free nucleic acid sequencing, and in particular, ion-based nucleic acid sequencing. The concept of label-free detection of nucleotide incorporation has been described in the literature, including the following references that are incorporated by reference: Rothberg et al, U.S. patent publication 2009/0026082; Anderson et al, Sensors and Actuators B Chem., 129: 79-86 (2008); and Pourmand et al, Proc. Natl. Acad. Sci., 103: 6466-6470 (2006). Briefly, in nucleic acid sequencing applications, nucleotide incorporations are determined by measuring natural byproducts of polymerase-catalyzed extension reactions, including hydrogen ions, polyphosphates, PPi, and Pi (e.g., in the presence of pyrophosphatase). Examples of such ion-based nucleic acid sequencing methods and platforms include the Ion Torrent PGM™ or Proton™ sequencer (Ion Torrent™ Systems, Life Technologies Corporation).

In some embodiments, the disclosure relates generally to methods for sequencing a nucleic acid using the nucleic acid fragment library produced by the teachings provided herein. In some embodiments, the nucleic acid fragment library can be used to generate a template library and the template library can be used to obtain sequence information. In one exemplary embodiment, the disclosure relates generally to a method for obtaining sequence information from a nucleic acid template, comprising:

(a) fragmenting a nucleic acid molecule into two or more fragments;

(b) performing template-dependent nucleic acid synthesis using at least one of the fragments produced during step (a) as a template.

In some embodiments, the fragmenting can include: (a) introducing one or more nicks on either strand of a double-stranded nucleic acid; and (b) moving the position of at least two of the nicks into alignment along the double-stranded nucleic acid. Alignment of nicks can result in double-stranded breaks or fragmentation points.

In some embodiments, the introducing can include introducing a nick on either strand of the double-stranded nucleic acid using an endonuclease. In some embodiments, the moving can include moving the positions of a nick to a new position along the double-stranded nucleic acid using one or more nick translating enzymes. In some embodiments, the fragmenting can further include enzymatically adding a 3' tail to a nick at a new position. In some embodiments, the fragmenting can further include joining an oligonucleotide adaptor to the fragmented nucleic acid, denaturing the adaptor and nick repairing the fragmented nucleic acid strand.

In some embodiments, the template-dependent synthesis includes incorporating one or more nucleotides in a template-dependent fashion into a newly synthesized nucleic acid strand.

Optionally, the methods can further include producing one or more ionic byproducts of such nucleotide incorporation.

In some embodiments, the methods can further include detecting the incorporation of the one or more nucleotides into the sequencing primer. Optionally, the detecting can include detecting the release of hydrogen ions.

In another embodiment, the disclosure relates generally to a method for sequencing a nucleic acid, comprising: (a) producing a plurality of nucleic acid fragments by fragmenting a nucleic acid molecule according to the methods disclosed herein; (b) disposing a plurality of nucleic acid fragments into a plurality of reaction chambers, wherein one or more of the reaction chambers are in contact with a field effect transistor (FET). Optionally, the method further includes contacting at least one of the nucleic acid fragments disposed into one of the reaction chambers with a polymerase, thereby synthesizing a new nucleic acid strand by sequentially incorporating one or more nucleotides into a nucleic acid molecule. Optionally, the method further includes generating one or more hydrogen ions as a byproduct of such nucleotide incorporation. Optionally, the method further includes detecting the incorporation of the one or more nucleotides by detecting the generation of the one or more hydrogen ions using the FET.

In some embodiments, the detecting includes detecting a change in voltage and/or current at the at least one FET within the array in response to the generation of the one or more hydrogen ions.

In some embodiments, the FET can be selected from the group consisting of: ion-sensitive FET (isFET) and chemically-sensitive FET (chemFET).

One exemplary system involving sequencing via detection of ionic byproducts of nucleotide incorporation is the Ion Torrent PGM™ or Proton™ sequencer (Life Technologies), which is an ion-based sequencing system that sequences nucleic acid templates by detecting hydrogen ions produced as a byproduct of nucleotide incorporation. Typically, hydrogen ions are released as byproducts of nucleotide incorporations occurring during template-dependent nucleic acid synthesis by a polymerase. The Ion Torrent PGM™ or Proton™ sequencer detects the nucleotide incorporations by detecting the hydrogen ion byproducts of the nucleotide incorporations. The Ion Torrent PGM™ or Proton™ sequencer can include a plurality of nucleic acid templates to be sequenced, each template disposed within a respective sequencing reaction well in an array. The wells of the array can each be coupled to at least one ion sensor that can detect the release of $H^+$ ions or changes in solution pH produced as a byproduct of nucleotide incorporation. The ion sensor comprises a field effect transistor (FET) coupled to an ion-sensitive detection layer that can sense the presence of $H^+$ ions or changes in solution pH. The ion sensor can provide output signals indicative of nucleotide incorporation which can be represented as voltage changes whose magnitude correlates with the $H^+$ ion concentration in a respective well or reaction chamber. Different nucleotide types can be flowed serially into the reaction chamber, and can be incorporated by the polymerase into an extending primer (or polymerization site) in an order determined by the sequence of the template. Each nucleotide incorporation can be accompanied by the release of $H^+$ ions in the reaction well, along with a concomitant change in the localized pH. The release of $H^+$ ions can be registered by the FET of the sensor, which produces signals indicating the occurrence of the nucleotide incorporation. Nucleotides that are not incorporated during a particular nucleotide flow may not produce signals. The amplitude of the signals from the FET can also be correlated with the number of nucleotides of a particular type incorporated into the extending nucleic acid molecule thereby permitting homopolymer regions to be resolved. Thus, during a run of the sequencer multiple nucleotide flows into the reaction chamber along with incorporation monitoring across a multiplicity of wells or reaction chambers can permit the instrument to resolve the sequence of many nucleic acid templates simultaneously. Further details regarding the compositions, design and operation of the Ion Torrent PGM™ or Proton™ sequencer can be found, for example, in U.S. patent application Ser. No. 12/002,781, now published as U.S. Patent Publication No. 2009/0026082; U.S. patent application Ser. No. 12/474,897, now published as U.S. Patent Publication No. 2010/0137143; and U.S. patent application Ser. No. 12/492,844, now published as U.S. Patent Publication No. 2010/0282617, all of which applications are incorporated by reference herein in their entireties.

In some embodiments, the disclosure relates generally to use of nucleic acid fragments produced using any of the methods, systems and kits of the present disclosure in methods of ion-based sequencing. Use of such nucleic acid fragments in ion-based sequencing reactions can be advantageous because the fragmenting methods of the disclosure permit isolation of fragments of a desired size that can be selected to match the read length capacity of the ion-based sequencing system.

In a typical embodiment of ion-based nucleic acid sequencing, nucleotide incorporations can be detected by detecting the presence and/or concentration of hydrogen ions generated by polymerase-catalyzed extension reactions. In one embodiment, templates each having a primer and polymerase operably bound can be loaded into reaction chambers (such as the microwells disclosed in Rothberg et al, cited herein), after which repeated cycles of nucleotide addition and washing can be carried out. In some embodiments, such templates can be attached as clonal populations to a solid support, such as particles, bead, or the like, and said clonal populations are loaded into reaction chambers. As used herein, "operably bound" means that a primer is annealed to a template so that the primer's 3' end may be extended by a polymerase and that a polymerase is bound to such primer-template duplex, or in close proximity thereof so that binding and/or extension takes place whenever nucleotides are added.

In each addition step of the cycle, the polymerase can extend the primer by incorporating added nucleotide only if the next base in the template is the complement of the added nucleotide. If there is one complementary base, there is one incorporation, if two, there are two incorporations, if three, there are three incorporations, and so on. With each such incorporation there is a hydrogen ion released, and collectively a population of templates releasing hydrogen ions changes the local pH of the reaction chamber. The production of hydrogen ions is monotonically related to the number of contiguous complementary bases in the template (as well as the total number of template molecules with primer and polymerase that participate in an extension reaction). Thus, when there are a number of contiguous identical complementary bases in the template (i.e. a homopolymer region), the number of hydrogen ions generated, and therefore the magnitude of the local pH change, can be proportional to the number of contiguous identical complementary bases. If the next base in the template is not complementary to the added nucleotide, then no incorporation occurs and no hydrogen ion is released. In some embodiments, after each step of adding a nucleotide, an additional step can be performed, in which an unbuffered wash solution at a predetermined pH is used to remove the nucleotide of the previous step in order to prevent misincorporations in later cycles. In some embodiments, the after each step of adding a nucleotide, an additional step can be performed wherein the reaction chambers are treated with a nucleotide-destroying agent, such as apyrase, to eliminate any residual nucleotides remaining in the chamber, which may result in spurious extensions in subsequent cycles.

In one exemplary embodiment, different kinds of nucleotides are added sequentially to the reaction chambers, so that each reaction can be exposed to the different nucleotides one at a time. For example, nucleotides can be added in the following sequence: dATP, dCTP, dGTP, dTTP, dATP, dCTP, dGTP, dTTP, and so on; with each exposure followed by a wash step. The cycles may be repeated for 50 times, 100 times, 200 times, 300 times, 400 times, 500 times, 750 times, or more, depending on the length of sequence information desired.

In some embodiments, sequencing can be performed according to the user protocols supplied with the PGM™ or Proton™ sequencer. Example 3 provides one exemplary protocol for ion-based sequencing using the Ion Torrent PGM™ sequencer (Ion Torrent™ Systems, Life Technologies, CA).

Systems

In some embodiments, the present teachings provide systems for generating a population of nucleic acid fragments, comprising: nucleic acids, one or more nicking enzymes, one or more nick translation enzymes and nucleotides. In some embodiments, systems for preparing fragmented nucleic acids can further comprise at least one nucleic acid binding protein (e.g., a single-stranded binding protein). In some embodiments, systems for preparing fragmented nucleic acids further comprise one or more tailing enzymes. In some embodiments, systems for preparing fragmented nucleic acids can further comprise at least one oligonucleotide adaptor. In some embodiments, systems for preparing fragmented nucleic acids further comprise any combination of: buffers; cations; size-selection reagents; one or more end-repairing enzyme(s); one or more repairing enzyme(s); one or more nick repair enzymes, one or more types of adaptor(s); one or more ligation enzyme(s); reagents for nucleic acid purification; reagents for nucleic acid amplification; endonuclease(s); polymerase(s); kinase(s); phosphatase(s); and/or nuclease(s).

Kits

In some embodiments, the present teachings provide kits for generating a population of nucleic acid fragments. In some embodiments, kits include any reagent that can be used to conduct nucleic acid fragmentation method. In some embodiments, kits include any combination of: buffers; cations; one or more nucleic acid nicking enzyme(s); one or more nick translation enzyme(s); one or more nucleotides; one or more nucleic acid tailing enzyme(s); size-selection reagents; one or more end-repairing enzyme(s); one or more repairing enzyme(s); one or more nick repair enzymes, one or more types of adaptor(s); one or more ligation enzyme(s); reagents for nucleic acid purification; and/or reagents for nucleic acid amplification. In some embodiments, kits include any combination of: endonuclease(s); polymerase(s); ligase(s); kinase(s); phosphatase(s); and/or nuclease(s).

EXAMPLES

Embodiments of the present teachings can be further understood in light of the following examples, which should not be construed as limiting the scope of the present teachings in any way.

Example 1

A. Enzymatic Nucleic Acid Fragmentation

Genomic DNA (0.5 ug) from DH10B, Rhodo or *Vibrio* was mixed with 5 uL of 10× Buffer with dNTP, 10 uL of enzyme mix from Nick Translation System (Invitrogen, catalog 18160-010), 40 mU DNase I, and water to make a total reaction volume of 50 uL.

The mixture was incubated at 37° C. for 15 minutes, and the reaction was stopped with 5 uL of Stop Buffer (0.5 M EDTA, pH 8). The fragmented DNA was purified with a SOLiD™ Library Micro Column Purification kit, using B2-S buffer and eluting with 20 uL of E1 buffer.

B. Library Preparation

The fragmented DNA from step (A) above (20 uL) was ligated to barcoded adaptors. The fragmented DNA was mixed in 10 uL of 5× Reaction buffer, barcoded adaptor P1 (50 uM stock), barcoded adaptor P2 (50 uM stock), 5 uL of 5 U/uL T4 DNA ligase, and water to make a total reaction volume of 50 uL.

The mixture was incubated at room temperature for 30 minutes. The DNA was purified with a SOLiD™ Library Micro Column Purification kit, using B2-S buffer and eluting with 20 uL of E1 buffer. The DNA was reacted in a nick translation reaction to get rid of the nick between the ligated barcoded adaptors and the DNA. The DNA was amplified with a Platinum™ PCR Amplification Mix in a total volume of 120 uL, and amplified in a thermocycler at 72° C. for 20 minute, 4° C. hold. The amplified DNA was purified with a SOLiD Library Micro Column Purification kit, using B2-S buffer and eluting with 20 uL of E1 buffer.

Example 2

A. Enzymatic Nucleic Acid Fragmentation

DNA (10 ng-1 ug) can be mixed in 1× iShear Buffer with dNTP, 1× iShear Enzyme Mix, in a total volume of 50 uL. The mixture can be incubated at 37° C. for 15 minutes, and the reaction can be stopped with 5 uL of Stop Buffer (0.5 M EDTA, pH 8). The fragmented DNA can be purified with AMPure XP beads (1.8×)(Agencourt), and the fragmented DNA can be retrieved with 22 uL of E1 buffer.

10× iShear Buffer can include: 500 mM Tris-HCl (pH 7.5), 3 mM dNTP and 55 mM MgCl$_2$ in water.

iShear Enzyme Mix can include: 50 mM Tris-HCl (pH 7.5), DNA polymerase I, DNase I, MgCl$_2$, 50% glycerol, and 100 ug/ml BSA.

B. Library Preparation

The fragmented DNA from step (A) above can be ligated to adaptors. The fragmented DNA can be mixed in 1× Reaction buffer, with adaptor P1, adaptor P2, 25 U T4 DNA ligase, 25 U Tfi (exo-) polymerase, 0.2 mM dNTPs, in a total volume of 50 uL. The mixture can be incubated in a thermocycler at 20° C. for 30 minutes, and 72° C. for 20 minutes. The DNA can be purified with AMPure XP beads (0.6×)(Agencourt) and washed with 200 uL of 70% ethanol three times. The next steps are optional. The DNA can be amplified with a Platinum™ PCR Amplification Mix using the library PCR primer 1 and 2 in a total volume of 125 uL, and amplified in a thermocycler at 95° C. for 5 minutes (95° C. for 15 seconds, 62° C. for 15 seconds, 70° C. for 1 minute)X # of cycles; 70° C. for 5 minutes, 4° C. hold. The amplified DNA can be purified with AMPure XP beads (1.5×)(Agencourt).

Example 3

Nucleic acid molecules were fragmented and ligated to adapters as described below and then amplified and sequenced in an Ion Torrent™ PGM™ sequencer (Ion Torrent™ Systems, Life Technologies) according to the manufacturer's supplied protocols.

Reagents

10× Shearing Buffer: 500 mM Tris HCl, pH 7.5; 55 mM MgCl$_2$; 3 mM dNTP in water.

Shearing Enzyme: 0.8 Units *E. coli* DNA Polymerase I; 0.0025 Units DNase I in storage buffer.

Stop Buffer: 0.5M EDTA (pH 8.0).

5× Ligase Buffer: 250 mM Tris-HCl, pH 7.6; 50 mM MgCl$_2$, 5 mM ATP, 5 mM DTT, 25% PEG-8000.

E1 Buffer: 10 mM Tris-HCl, pH 8.5.

Adapters: Ion Torrent Part No: 602-1067-01, available as part of the Ion Fragment Library Kit.

Fragmentation of Nucleic Acid Molecules; Purification of Nucleic Acid Fragments

The following reagents were combined in a 1.5 ml LoBind tube (Eppendorf #022431021):

| | |
|---|---|
| DNA to be fragmented: | 2 µg |
| 10X Shearing Buffer | 5 µL |
| Shearing Enzyme Mix | 10 µL |
| Deionized water | to final volume of 50 µL |

The contents of the LoBind tube were mixed and incubated at 37° C. for 15 minutes.

5 µL of Stop Buffer was added to the reaction, the mixture was vortexed and placed on ice.

The fragmented nucleic acid molecules were purified using the Agencourt™ AMPure™ XP kit (Beckman #A63880) according to the following protocol: 99 µl Agencourt® AMPure® beads (1.8 volumes) were added to the sample, which was then vortexed and pulse-spin. The mixture was incubated at room temperature (20-25° C.) for 5 minutes. The tube was placed in a DynaMag™-2 magnetic rack for at least 1 minute until the solution was clear of brown tint when viewed at an angle; then the supernatant was carefully removed and discarded. The beads were washed three times with 300 µL of 70% ethanol, then dried at room temperature for 5 minutes. The DNA was eluted from the beads using 50 µL E1 buffer (supplied with the AMPure Kit). The supernatant containing the eluted DNA was transferred to a new 1.5-mL LoBind tube.

Ligation of Adapters to Sheared DNA

In a 1.5 ml LoBind tube, add 5× reaction buffer, 50 uM adapters (Ion Torrent cat no: 602-1067-01), 5 U/ul T4 DNA ligase were combined to a final volume of 53 µL as follows:

| | |
|---|---|
| DNA | 50 ul |
| 5x Ligase buffer | 20 ul |
| 50 uM adapters | 20 ul |
| 5U/ul T4 DNA ligase | 10 ul |
| Total Volume | 100 ul |

The ligation mixture was incubated at room temperature for 30 minutes.

The ligated DNA was purified using the Agencourt™ AMPure™ XP kit (Beckman #A63880) according to the following protocol: 180 μL Agencourt® AMPure® beads (1.8 volumes) were added to the sample, which was then vortexed and pulse-spin. The mixture was incubated at room temperature (20-25° C.) for 5 minutes. The tube was placed in a DynaMag™-2 magnetic rack for at least 1 minute until the solution was clear of brown tint when viewed at an angle; then the supernatant was carefully removed and discarded. The beads were washed three times with 300 μL of 70% ethanol, then dried at room temperature for 5 minutes. The DNA was eluted from the beads using 30 μL E1 buffer (supplied with the AMPure Kit). The supernatant containing the eluted DNA was transferred to a new 1.5-mL LoBind tube.

The DNA was then size-selected using a Pippin Prep™ instrument (Sage Sciences) to achieve a size distribution of 50-80 bp, essentially according to the manufacturer's provided protocol.

The size-selected DNA was diluted to a total volume of 60 μL, and then purified using the Agencourt™ AMPure™ XP kit (Beckman #A63880) according to the following protocol: 108 μL Agencourt® AMPure® beads (1.8 volumes) were added to the sample, which was then vortexed and pulse-spin. The mixture was incubated at room temperature (20-25° C.) for 5 minutes. The tube was placed in a DynaMag™-2 magnetic rack for at least 1 minute until the solution was clear of brown tint when viewed at an angle; then the supernatant was carefully removed and discarded. The beads were washed twice with 500 μL of freshly prepared 70% ethanol, then dried at room temperature for 5 minutes. The DNA was eluted from the beads using 40 μL E1 buffer (supplied with the AMPure Kit). The supernatant containing the eluted DNA was transferred to a new 1.5-mL LoBind tube.

Nick Translation and Library Amplification

The following reaction mixture was prepared:

| | |
|---|---|
| Platinum PCR SuperMix High Fidelity | 200 μL |
| Primer Mix | 10 μL |
| Size selected DNA | 40 μL |
| Total | 250 |

The mixture was aliquoted in batches of 125 μL into each of two PCR tubes.

The PCR tubes were subjected to the following cycle:

| Stage | Step | Temp | Time |
|---|---|---|---|
| Holding | Nick translation | 72° C. | 20 min |
| Holding | Denature | 95° C. | 5 min |
| Cycling (4 cycles) | Denature | 95° C. | 15 sec |
| | Anneal | 58° C. | 15 sec |
| | Extend | 72° C. | 1 min |
| Holding | Extend | 72° C. | 3 min |
| Holding | — | 4° C. | ∞ |

The PCR samples were pooled into a new 1.5 ml LoBind tube.

The mixture was then purified using the Agencourt™ AMPure™ XP kit (Beckman #A63880) according to the following protocol: 375 μl Agencourt® AMPure® beads (1.5 volumes) were added to the sample, which was then vortexed. The mixture was incubated at room temperature (20-25° C.) for 10 minutes on a rotator. The tube was placed in a DynaMag™-2 magnetic rack for at least 1 minute until the solution was clear of brown tint when viewed at an angle; then the supernatant was carefully removed and discarded. The beads were washed three with 500 μL of freshly prepared 70% ethanol, then dried at room temperature for 5 minutes. The DNA was eluted from the beads using 50 μL E1 buffer (supplied with the AMPure Kit). The supernatant containing the eluted DNA was transferred to a new 1.5-mL LoBind tube.

The concentration of the eluted DNA was measured using the Agilent Bioanalyzer™ High Sensitivity DNA Kit (Agilent, Catalog No. 5067-4626), and also separately using the Invitrogen Qubit™ dsDNA HS Assay Kit (Invitrogen Part no. Q32851 or Q32854).

The purified, adapter-ligated and size selected DNA fragments were then amplified onto Ion Sphere™ particles (Ion Torrent Systems/Life Technologies, Part No. 602-1075-01) essentially according to the protocols provided in the Ion Xpress™ Template Kit User Guide (Ion Torrent Systems/Life Technologies, Part No. 4467389), hereby incorporated by reference in its entirety, and using the reagents provided in the Ion Template Preparation Kit (Ion Torrent Systems/Life Technologies, Part No. 4466461), the Ion Template Reagents Kit (Ion Torrent Systems/Life Technologies, Part No. 4466462) and the Ion Template Solutions Kit (Ion Torrent Systems/Life Technologies, Part No. 4466463). The amplified DNA was then sequenced on an Ion PGM™ sequencer (Ion Torrent Systems/Life Technologies, Part No. 4462917) essentially according to the protocols provided in the Ion Sequencing Kit User Guide (Ion Torrent Systems/Life Technologies, Part No. 4467391), hereby incorporated by reference in its entirety, using the reagents provided in the Ion Sequencing Kit (Ion Torrent Systems/Life Technologies, Part No. 4466456) and the Ion Chip Kit (Ion Torrent Systems/Life Technologies, Part No. 4462923). Ion Torrent Systems is a subsidiary of Life Technologies Corp., Carlsbad, Calif.).

Example 4

Nucleic acid molecules (Amplicon or genomic DNA) were fragmented and ligated to adapters as described below and sequenced using an Ion Torrent™ PGM™ sequencer (Ion Torrent™ Systems, Life Technologies) according to the manufacturers supplied protocols.

Reagents

10× Ion Shear™ Plus Reaction Buffer can include: 500 mM Tris-HCl (pH 7.5), 55 mM $MgCl_2$ and 3 mM dNTP in water.

Ion Shear™ Plus Enzyme Mix can include: DNA polymerase I, DNase I, 50 mM Tris-HCl (pH 7.5), $MgCl_2$, 0.75 mg/ml BSA and 50% glycerol.

Ion Shear™ Plus Stop Buffer can include: 0.5M EDTA (pH 8).

Nick Repair Enzyme can include: Taq DNA polymerase, Bst DNA polymerase, Platinum® Pfx DNA polymerase (Invitrogen), Tfi Exo(−) DNA polymerase (Invitrogen) or Phusion® Hot Start High-Fidelity DNA polymerase (New England Biolabs).

10 mM dNTP: 10 mM dNTPs in water.

DNA Ligase: Life Technologies Part. No. 602-1060-01.

10× Ligase Buffer can include: 250 mM Tris-HCl (pH 7.6), 50 mM MgCl$_2$, 5 mM ATP, 5 mM DTT and 25% PEG-8000 (Life Technologies Part. No. 602-1060-01).

Low TE can include: Tris-EDTA (Ion Torrent™ Part No: 602-1066-01, available as part of the Ion Fragment Library Kit (Part No. 4466464).

Adapters: Ion Torrent™ Part No: 602-1067-01, available as part of the Ion Fragment Library Kit (Part No. 4466464).

Fragmentation of Nucleic Acid Molecules

The following method fragments double stranded DNA into blunt-ended fragments in the 200-300 bp size range. The fragmented DNA is ready for adaptor ligation, followed by nick repair to complete linkage between adaptors and DNA. The adaptor-ligated fragments are then size-selected for optimum fragment length, for example using E-Gel Size Select 2% agarose gel or Pippin Prep™ instrument for automated size selection.

For inputs of 100 ng or greater, the resulting amplification free library is sufficient for most downstream processing, for example for use with Ion Sphere™ particles (Ion Torrent™, Life Technologies, Part No. 602-1075-01) essentially according to the protocols provided in the Ion Xpress™ Template Kit User Guide (Ion Torrent™, Life Technologies, Part No. 4467389), hereby incorporated by reference in its entirety, using the reagents provided in the Ion Template Preparation Kit (Ion Torrent™, Life Technologies, Part No. 4466461), the Ion Template Reagents Kit (Ion Torrent™, Life Technologies, Part No. 4466462) and the Ion Template Solutions Kit (Ion Torrent™, Life Technologies, Part No. 4466463). Template preparations can then be sequenced on an Ion PGM™ sequencer (Ion Torrent™, Life Technologies, Part No. 4462917) essentially according to the protocols provided in the Ion Sequencing Kit User Guide (Ion Torrent™ Life Technologies, Part No. 4467391), hereby incorporated by reference in its entirety.

In this example, the following reagents were combined in a 1.5 ml LoBind tube (Eppendorf, Cat. No. 022431021):

| | |
|---|---|
| Nucleic acids to be fragmented at 100 ng/μL | 1 μg |
| 10X Ion Shear™ Plus Reaction Buffer | 5 μL |
| Deionized water | 25 μL |

The contents of the tube were mixed vigorously by vortexing for 5 seconds, pulse-spin and the following amount of Ion Shear™ Plus Enzyme Mix added to the tube:

| | |
|---|---|
| Ion Shear™ Plus Enzyme Mix | 10 μL |

The contents of the LoBind tube were mixed and incubated at 37° C. for 15 minutes.

5 μL of Ion Shear™ Plus Stop Buffer was added to the reaction; the mixture was vortexed and placed on ice.

The fragmented nucleic acid molecules were purified using the Agencourt™ AMPure™ XP kit (Beckman Part. No. A63880) according to the following protocol:

99 μl Agencourt® AMPure® beads (1.8 volumes) were added to the sample, which was then vortexed and pulse-spin. The mixture was incubated at room temperature (20-25° C.) for 5 minutes. The tube was placed in a DynaMag™-2 magnetic rack for 3 minutes until the solution was clear of brown tint when viewed at an angle; then the supernatant was carefully removed and discarded. The beads were washed twice with 500 μL of 70% ethanol, then dried at room temperature for 5 minutes. The DNA was eluted from the beads using 25 μL Low TE, which was then vortexed and pulse-spin. The sample was placed in a DynaMag™-2 magnetic rack for at least one minute until the solution was clear. The supernatant containing the eluted DNA was transferred to a new 0.2 mL PCR tube.

Ligation of Adapters to DNA and Nick Repair

In a 0.2 ml PCR tube containing the eluted DNA (~1 μg), add 10× Ligase Buffer, Adapters (Ion Torrent™ Cat. no: 602-1067-01), dNTP mix, DNA ligase, and Nick repair enzyme were combined to a final volume of 100 μL as follows:

| | |
|---|---|
| DNA | 25 ul |
| 10x Ligase buffer | 10 ul |
| Adapters | 10 ul |
| dNTP Mix | 2 ul |
| DNA ligase | 2 ul |
| Nick repair enzyme | 8 ul |
| Nuclease-free water | 43 ul |
| Total Volume | 100 ul |

The ligation mixture was placed into a thermocycler programmed as follows:

25° C. for 15 minutes; and then 72° C. for 5 minutes; followed by holding at 4° C.

The adaptor-ligated and nick-repaired DNA was purified using the Agencourt™ AMPure™ XP kit (Beckman Part. No. A63880) according to the following protocol:

150 μl Agencourt® AMPure® beads (1.5 volumes) were added to the sample, which was then vortexed and pulse-spin. The mixture was incubated at room temperature (20-25° C.) for 5 minutes. The tube was placed in a DynaMag™-2 magnetic rack for 3 minutes until the solution was clear of brown tint when viewed at an angle; then the supernatant was carefully removed and discarded. The beads were washed twice with 500 μL of 70% ethanol, then dried at room temperature for 5 minutes. The DNA was eluted from the beads using 20 μL Low TE, which was then vortexed and pulse-spin. The sample was placed in a DynaMag™-2 magnetic rack for at least one minute until the solution was clear. The supernatant containing the eluted DNA was transferred to a new 1.5-mL LoBind tube.

Size Selection

The DNA was then size-selected using a E-Gel SizeSelect Agarose Gel (2%) (Life Technologies, G6610-02) to achieve 200 nucleotide sequencing reads, a DNA library with a peak size of ~330 bp was selected, essentially according to the manufacturer's provided protocol. The DNA solution (~40 μl) recovered from the SizeSelect Gel did not require additional purification for downstream processing (e.g., qPCR quantification or emulsion PCR). In an alternative method, a Pippin Prep™ instrument can be used to automate size-selection.

The concentration of the eluted DNA from the SizeSelect gel was measured using the Agilent Bioanalyzer™ High Sensitivity DNA Kit (Agilent, Catalog No. 5067-4626), and also separately using the Invitrogen Qubit™ dsDNA HS Assay Kit (Invitrogen Part no. Q32851 or Q32854).

The size selected DNA fragments were then amplified onto Ion Sphere™ particles (Ion Torrent™, Life Technologies, Part No. 602-1075-01) essentially according to the protocols provided in the Ion Xpress™ Template Kit User Guide (Ion Torrent™, Life Technologies, Part No. 4467389), hereby incorporated by reference in its entirety, and using the reagents provided in the Ion Template Preparation Kit (Ion Torrent™, Life Technologies, Part No. 4466461), the Ion Template Reagents Kit (Ion Torrent™, Life Technologies, Part No. 4466462) and the Ion Template Solutions Kit (Ion Torrent™, Life Technologies, Part No. 4466463). The amplified DNA was then sequenced on an Ion PGM™ sequencer (Ion Torrent™ Systems, Life Technologies, Part No. 4462917) essentially according to the protocols provided in the Ion Sequencing Kit User Guide (Ion Torrent™, Life Technologies, Part No. 4467391), hereby incorporated by reference in its entirety, and using the reagents provided in the Ion Sequencing Kit (Ion Torrent™, Life Technologies, Part No. 4466456) and the Ion Chip Kit (Ion Torrent™, Life Technologies, Part No. 4462923).

Example 5

Nucleic acid molecules (Amplicon or genomic DNA) were fragmented and ligated to adapters as described below and sequenced on an Ion Torrent™ PGM™ sequencer (Ion Torrent™ Systems, Life Technologies) according to the manufacturers supplied protocols.

Reagents

10× Ion Shear™ Plus Reaction Buffer can include: 500 mM Tris-HCl (pH 7.5), 55 mM MgCl$_2$ and 3 mM dNTP in water.

Ion Shear™ Plus Enzyme Mix can include: DNA polymerase I; DNase I; 50 mM Tris-HCl (pH 7.5), MgCl$_2$, 0.75 mg/ml BSA and 50% glycerol.

Ion Shear™ Plus Stop Buffer can include: 0.5M EDTA (pH 8.0).

Nick Repair Enzyme can include: Taq DNA polymerase, Bst DNA polymerase, Platinum® Pfx DNA polymerase (Invitrogen), Tfi Exo(−) DNA polymerase (Invitrogen) or Phusion® Hot Start High-Fidelity DNA polymerase (New England Biolabs).

10 mm dNTP: 10 mm dNTPs in water.

DNA Ligase: Life Technologies Part. No. 602-1060-01.

10× Ligase Buffer can include: 250 mM Tris-HCl (pH 7.6), 50 mM MgCl$_2$, 5 mM ATP, 5 mM DTT and 25% PEG-8000 (Life Technologies Part. No. 602-1060-01).

Low TE can include: Tris-EDTA (Ion Torrent™ Part No: 602-1066-01, available as part of the Ion Fragment Library Kit (Part No. 4466464).

Adapters: Ion Torrent™ Part No: 602-1067-01, available as part of the Ion Fragment Library Kit (Part No. 4466464).

Fragmentation of Nucleic Acid Molecules

The following reagents were combined in a 1.5 ml LoBind tube (Eppendorf, Cat. No. 022431021):

| | |
|---|---|
| Nucleic acids to be fragmented at 100 ng/µL | 1 µg |
| 10X Ion Shear™ Plus Reaction Buffer | 5 µL |
| Deionized water | 25 µL |

The contents of the tube were mixed vigorously by vortexing for 5 seconds, pulse-spin and the following amount of Ion Shear™ Plus Enzyme Mix added to the tube:

| | |
|---|---|
| Ion Shear™ Plus Enzyme Mix | 10 µL |

The contents of the LoBind tube were mixed and incubated at 37° C. for 15 minutes.

5 µL of Ion Shear™ Plus Stop Buffer was added to the reaction; the mixture was vortexed and placed on ice.

The fragmented nucleic acid molecules were purified using the Agencourt™ AMPure™ XP kit (Beckman Part. No. A63880) according to the following protocol to produce double stranded DNA fragments in the range of 180-250 bp:

99 µl Agencourt® AMPure® beads (1.8 volumes) were added to the sample, which was then vortexed and pulse-spin. The mixture was incubated at room temperature (20-25° C.) for 5 minutes. The tube was placed in a DynaMag™-2 magnetic rack for 3 minutes until the solution was clear of brown tint when viewed at an angle; then the supernatant was carefully removed and discarded. The beads were washed twice with 500 µL of 70% ethanol, then dried at room temperature for 5 minutes. The DNA was eluted from the beads using 25 µL Low TE, which was then vortexed and pulse-spin. The sample was placed in a DynaMag™-2 magnetic rack for at least one minute until the solution was clear. The supernatant containing the eluted DNA was transferred to a new 1.5-mL LoBind tube.

AMPure™ XP Beads 49.5 µl Agencourt® AMPure® beads (0.9 volume) were added to the sample, which was then vortexed and pulse-spin. The mixture was incubated at room temperature (20-25° C.) for 5 minutes. The tube was placed in a DynaMag™-2 magnetic rack for 3 minutes until the solution was clear of brown tint when viewed at an angle; then the supernatant was carefully removed to a new 1.5-mL LoBind tube. To the supernatant, 11 µl of Agencourt® AMPure® beads (0.2× original sample volume) were added to the sample, which was then vortexed and pulse-spin. The mixture was incubated at room temperature (20-25° C.) for 5 minutes. The tube was placed in a DynaMag™-2 magnetic rack for 3 minutes until the solution was clear of brown tint when viewed at an angle; then the supernatant was carefully removed and discarded. The beads were washed twice with 500 µL of 70% ethanol, then dried at room temperature for 5 minutes. The DNA was eluted from the beads using 25 µL Low TE, which was then vortexed and pulse-spin. The sample was placed in a DynaMag™-2 magnetic rack for at least one minute until the solution was clear. The supernatant containing the eluted DNA was transferred to a new 0.2-mL PCR tube.

Ligation of Adapters to DNA and Nick Repair

To the 0.2-mL PCR tube containing the eluted DNA (~1 µg), add 10× Ligase Buffer, Adapters (Ion Torrent™ Cat. no: 602-1067-01), dNTP mix, DNA ligase, and Nick Repair Enzyme were combined to a final volume of 100 µL as follows:

| | |
|---|---|
| DNA | 25 ul |
| 10x Ligase buffer | 10 ul |
| Adapters | 10 ul |
| dNTP Mix | 2 ul |
| DNA ligase | 2 ul |
| Nick Repair Enzyme | 8 ul |
| Nuclease-free water | 43 ul |
| Total Volume | 100 ul |

The mixture was placed into a thermocycler programmed as follows: 25° C. for 15 minutes; and then 72° C. for 5 minutes; followed by holding at 4° C.

The adaptor-ligated and nick-repaired DNA was purified using the Agencourt™ AMPure™ XP kit (Beckman Part. No. A63880) according to the following protocol:

140 µl Agencourt® AMPure® beads (1.4 volumes) were added to the sample, which was then vortexed and pulse-spin. The mixture was incubated at room temperature (20-25° C.) for 5 minutes. The tube was placed in a DynaMag™-2 magnetic rack for 3 minutes until the solution was clear of brown tint when viewed at an angle; then the supernatant was carefully removed and discarded. The beads were washed twice with 500 µL of 70% ethanol, then dried at room temperature for 5 minutes. The DNA was eluted from the beads using 20 µL Low TE, which was then vortexed and pulse-spin. The sample was placed in a DynaMag™-2 magnetic rack for at least one minute until the solution was clear. The supernatant containing the eluted DNA was transferred to a new 1.5-mL LoBind tube.

The DNA solution (~20 µl) recovered did not require additional purification for downstream processing (e.g., qPCR quantification or emulsion PCR) and generated library with a mean size of 280-310 bp.

The concentration of the eluted DNA was measured using the Agilent Bioanalyzer™ High Sensitivity DNA Kit (Agilent, Catalog No. 5067-4626), and also separately using the Invitrogen Qubit™ dsDNA HS Assay Kit (Invitrogen Part no. Q32851 or Q32854).

The size selected DNA fragments were then amplified onto Ion Sphere™ particles (Ion Torrent™, Life Technologies, Part No. 602-1075-01) essentially according to the protocols provided in the Ion Xpress™ Template Kit User Guide (Ion Torrent™, Life Technologies, Part No. 4467389), hereby incorporated by reference in its entirety, and using the reagents provided in the Ion Template Preparation Kit (Ion Torrent™, Life Technologies, Part No. 4466461), the Ion Template Reagents Kit (Ion Torrent™, Life Technologies, Part No. 4466462) and the Ion Template Solutions Kit (Ion Torrent™, Life Technologies, Part No. 4466463). The amplified DNA was then sequenced on an Ion PGM™ sequencer (Ion Torrent™, Life Technologies, Part No. 4462917) essentially according to the protocols provided in the Ion Sequencing Kit User Guide (Ion Torrent™, Life Technologies, Part No. 4467391), hereby incorporated by reference in its entirety, and using the reagents provided in the Ion Sequencing Kit (Ion Torrent™, Life Technologies, Part No. 4466456) and the Ion Chip Kit (Ion Torrent™, Life Technologies, Part No. 4462923).

Example 6

Nucleic acids (gDNA or Amplicons) were fragmented and ligated to adapters as described in Examples 4 and 5. In some instances, DNA input is less than required for downstream template preparation, and as such the fragmented nucleic acid library (from Examples 4 and 5) can be optionally amplified as described below to generate a library ready for downstream Template preparation, for example for use in the Ion Xpress™ Template Kit (Ion Torrent™, Life Technologies, Part No. 4467389). The DNA can then be sequenced on an Ion PGM™ sequencer (Ion Torrent™, Life Technologies, Part No. 4462917) essentially according to the protocols provided in the Ion Sequencing Kit User Guide (Ion Torrent™, Life Technologies, Part No. 4467391), hereby incorporated by reference in its entirety, using the reagents provided in the Ion Sequencing Kit (Ion Torrent™, Life Technologies, Part No. 4466456) and the Ion Chip Kit (Ion Torrent™, Life Technologies, Part No. 4462923).

Library Amplification

The following reaction mixture was prepared in a PCR tube containing 100 ng genomic DNA or amplicon prepared as described in Examples 4 and 5:

| Platinum PCR SuperMix High Fidelity | 100 µL |
| Primer Mix | 5 µL |
| Size-selected amplification-free DNA | 25 µL |
| Total | 130 |

The PCR tube was placed into a thermal cycler and run the following PCR cycling program:

| Stage | Step | Temp | Time |
| --- | --- | --- | --- |
| Holding | Denature | 95° C. | 5 min |
| Cycling (5-9 cycles) | Denature | 95° C. | 15 sec |
|  | Anneal | 58° C. | 15 sec |
|  | Extend | 70° C. | 1 min |
| Holding | — | 4° C. | ∞ |

The mixture was then purified using the Agencourt™ AMPure™ XP kit (Beckman Cat. No. A63880) according to the following protocol: 195 µl Agencourt® AMPure® beads (1.5 volumes) were added to the sample, which was then vortexed. The mixture was incubated at room temperature (20-25° C.) for 5 minutes. The tube was placed in a DynaMag™-2 magnetic rack for at least 3 minutes until the solution was clear of brown tint when viewed at an angle; then the supernatant was carefully removed and discarded. The beads were washed twice with 500 µL of freshly prepared 70% ethanol, then dried at room temperature for 5 minutes. The DNA was eluted from the beads using 20 µL Low TE. The supernatant containing the eluted DNA was transferred to a new 1.5-mL LoBind tube.

The concentration of the eluted DNA was measured using the Agilent Bioanalyzer™ High Sensitivity DNA Kit (Agilent, Catalog No. 5067-4626), and also separately using the Invitrogen Qubit™ dsDNA HS Assay Kit (Invitrogen Part no. Q32851 or Q32854).

The size selected DNA fragments were then amplified onto Ion Sphere™ particles (Ion Torrent™, Life Technologies, Part No. 602-1075-01) essentially according to the protocols provided in the Ion Xpress™ Template Kit User Guide (Ion Torrent™, Life Technologies, Part No. 4467389), hereby incorporated by reference in its entirety, and using the reagents provided in the Ion Template Preparation Kit (Ion Torrent™, Life Technologies, Part No. 4466461), the Ion Template Reagents Kit (Ion Torrent™, Life Technologies, Part No. 4466462) and the Ion Template Solutions Kit (Ion Torrent™, Life Technologies, Part No. 4466463). The amplified DNA was then sequenced on an Ion PGM™ sequencer (Ion Torrent™, Life Technologies, Part No. 4462917) essentially according to the protocols provided in the Ion Sequencing Kit User Guide (Ion Torrent™, Life Technologies, Part No. 4467391), hereby incorporated by reference in its entirety, and using the reagents provided in the Ion Sequencing Kit (Ion Torrent™, Life Technologies, Part No. 4466456) and the Ion Chip Kit (Ion Torrent™, Life Technologies, Part No. 4462923).

Example 7

Nucleic acid fragmentation reactions were conducted in a LoBind tube: 1 ug DNA (e.g., genomic or amplicon) was mixed with 5 uL of 10× Ion Shear Plus Reaction buffer, 10 uL of Ion Shear Plus Enzyme Mix, between about 5-50 ug of gp 32 protein (e.g., 40 ug of gp32 protein), and water to a final volume of 50 uL. The reaction was incubated at 37° C. for 15 minutes, and 5 uL of Stop buffer was added. The reaction was vortexed and placed on ice.

The fragmented nucleic acid molecules were purified using the Agencourt™ AMPure™ XP kit (Beckman Part. No. A63880) according to the following protocol: 99 µl Agencourt® AMPure® beads (1.8 volumes) were added to the sample, which was then vortexed and pulse-spin. The mixture was incubated at room temperature (20-25° C.) for 5 minutes. The tube was placed in a DynaMag™-2 magnetic rack for 3 minutes until the solution was clear of brown tint when viewed at an angle; then the supernatant was carefully removed and discarded. The beads were washed twice with 500 µL of 70% ethanol, then dried at room temperature for 5 minutes. The DNA was eluted from the beads using 25 µL Low TE, which was then vortexed and pulse-spin. The sample was placed in a DynaMag™-2 magnetic rack for at least one minute until the solution was clear. The supernatant containing the eluted DNA was transferred to a new 1.5-mL LoBind tube.

DNA fragmented in the presence of gp32 protein was ligated to adapters as described in Examples 4 and 5 above. In some instances, DNA input is less than required for downstream template preparation, and as such the fragmented nucleic acid library can be optionally amplified as described in Example 6 above to generate a library ready for downstream Template preparation, for example for use in the Ion Xpress™ Template Kit (Ion Torrent™, Life Technologies, Part No. 4467389). The DNA can then be sequenced on an Ion PGM™ sequencer (Ion Torrent™, Life Technologies, Part No. 4462917) essentially according to the protocols provided in the Ion Sequencing Kit User Guide (Ion Torrent™, Life Technologies, Part No. 4467391), hereby incorporated by reference in its entirety, using the reagents provided in the Ion Sequencing Kit (Ion Torrent™, Life Technologies, Part No. 4466456) and the Ion Chip Kit (Ion Torrent™, Life Technologies, Part No. 4462923).

While the principles of the present teachings have been described in connection with specific embodiments, it should be understood clearly that these descriptions are made only by way of example and are not intended to limit the scope of the present teachings or claims. What has been disclosed herein has been provided for the purposes of illustration and description. It is not intended to be exhaustive or to limit what is disclosed to the precise forms described. Many modifications and variations will be apparent to the practitioner skilled in the art. What is disclosed was chosen and described in order to best explain the principles and practical application of the disclosed embodiments of the art described, thereby enabling others skilled in the art to understand the various embodiments and various modifications that are suited to the particular use contemplated. It is intended that the scope of what is disclosed be defined by the following claims and their equivalents.

What is claimed:

1. A method for fragmenting a double stranded nucleic acid to generate at least two nucleic acid fragments of the double stranded nucleic acid, comprising:
   (a) exposing the double stranded nucleic acid to nicking conditions in which, for each strand of the double stranded nucleic acid, at least one linkage between adjacent nucleotides is disrupted at any random location to create a nick while the corresponding nucleotides opposite the nick in the opposing strand of the nucleic acid remain linked wherein the opposing strands remain attached through base pairing interactions, thereby generating a nicked nucleic acid; and
   (b) nick translating at least one nick in each strand of the nicked nucleic acid whereby the nick is positioned in sufficiently close proximity to a nick in the opposing strand to generate at least one double-stranded break in the nicked nucleic acid, thereby producing a plurality of nucleic acid fragments of the double stranded nucleic acid, wherein the nicking and/or the nick translating is conducted in the presence of at least one single-strand nucleic acid binding protein.

2. The method of claim 1, wherein the nick translating comprises a 5' to 3' DNA polymerization/degradation reaction or a 5' to 3' DNA polymerization/strand displacement reaction.

3. The method of claim 1, wherein the nick translating includes polymerizing one or more unlabeled nucleotides onto the 3' end of at least one nick.

4. The method of claim 1, wherein at least one of the nucleic acid fragments is not labeled.

5. The method of claim 1, wherein substantially all of the nucleic acid fragments are not labeled.

6. The method of claim 1, further comprising adjusting the average size of the nucleic acid fragments by modulating the reaction conditions for the nicking conditions.

7. A method for nucleic acid fragmentation, comprising:
   (a) providing a solution including a plurality of double stranded nucleic acid molecules which includes a first and a second double stranded nucleic acid molecule; and
   (b) subjecting at least two different nucleic acid molecules of the plurality to the method of claim 1.

8. The method of claim 7, further including fragmenting the at least two different nucleic acid molecules of the plurality in the same reaction mixture.

9. The method of claim 1, wherein the nicking conditions include the presence of DNase I.

10. The method of claim 9, wherein the nicking conditions further include the presence of magnesium.

11. The method of claim 9, wherein the nicking conditions do not include the presence of manganese.

12. The method of claim 1, wherein the at least one single-strand nucleic acid binding protein comprises T4 gp32 protein.

* * * * *